US012751665B2

(12) United States Patent
Kaplan et al.

(10) Patent No.: US 12,751,665 B2
(45) **Date of Patent: *Oct. 6, 2026**

(54) REMOTE MONITORING BASED WEARABLE APPARATUS AND RELATED METHOD FOR OPIOID OVERDOSE DETECTION AND ANTIDOTE DELIVERY

(71) Applicants: Irving D. Kaplan, Dedham, MA (US); Edward J. Holupka, Medway, MA (US)

(72) Inventors: Irving D. Kaplan, Dedham, MA (US); Edward J. Holupka, Medway, MA (US)

(73) Assignee: Ezer Enterprises LLC, Dedham, MA (US)

( * ) Notice: Subject to any disclaimer, the term of this patent is extended or adjusted under 35 U.S.C. 154(b) by 153 days.

This patent is subject to a terminal disclaimer.

(21) Appl. No.: 18/820,824

(22) Filed: Aug. 30, 2024

(65) Prior Publication Data

US 2026/0060611 A1 Mar. 5, 2026

(51) Int. Cl.
*A61B 5/00* (2006.01)
*A61B 5/0205* (2006.01)
(Continued)

(52) U.S. Cl.
CPC .......... *A61B 5/4839* (2013.01); *A61B 5/0002* (2013.01); *A61B 5/0205* (2013.01);
(Continued)

(58) Field of Classification Search
CPC ................ A61B 5/4839; A61B 5/0002; A61B 5/0205; A61B 5/0816; A61B 5/6802;
(Continued)

(56) References Cited

U.S. PATENT DOCUMENTS 10,874,358 B2 12/2020 Insler
10,932,729 B2 3/2021 Kiani
(Continued)

FOREIGN PATENT DOCUMENTS

CA 3105627 A1 7/2022
WO 2021/252971 A2 12/2021
(Continued)

OTHER PUBLICATIONS

Chan et al., "Closed-Loop Wearable Naloxone Injector System", Scientific Reports, 11:22663, 2021.
(Continued)

*Primary Examiner* — Jack Yip
(74) *Attorney, Agent, or Firm* — Zaretsky Group PC; Howard Zaretsky

(57) ABSTRACT

A novel and useful respiratory monitoring system and related methods that can interact with an opioid user and initiate a lifesaving drug injection process to mitigate opioid induced respiratory depression in an opioid user when opioid induced respiratory depression is detected. The system and methods include a wearable device that acquires physiological and other information from an opioid user during an opioid use session, analyzes the information to detect the presence of opioid induced respiratory depression in the opioid user, and initiates a lifesaving drug injection process when the presence of opioid induced respiratory depression is detected. Several methods are disclosed including self-monitoring and remote monitoring schemes that present a challenge to the opioid user with post injection stimulation of the opioid user and notification of caregivers and medical personnel.

20 Claims, 24 Drawing Sheets

(51) Int. Cl.
*A61B 5/08* (2006.01)
*G16H 10/60* (2018.01)

(52) U.S. Cl.
CPC .......... *A61B 5/0816* (2013.01); *A61B 5/6802* (2013.01); *A61B 5/746* (2013.01); *G16H 10/60* (2018.01)

(58) Field of Classification Search
CPC ..... A61B 5/746; A61B 5/0022; A61B 5/1118; A61B 5/4845; A61B 5/681; G16H 10/60; G16H 20/17; G16H 40/63; G16H 40/67; G16H 50/20; G16H 50/30
See application file for complete search history.

(56) References Cited

U.S. PATENT DOCUMENTS

| | | | | |
|---|---|---|---|---|
| 11,367,519 | B1 * | 6/2022 | Heldman | G16H 40/63 |
| 11,854,680 | B1 * | 12/2023 | Gershoni | A61J 1/035 |
| 2007/0032891 | A1 * | 2/2007 | Choi | G16H 20/17<br>700/65 |
| 2016/0063838 | A1 * | 3/2016 | Lee | G08B 21/18<br>340/539.13 |
| 2017/0239418 | A1 * | 8/2017 | Levine | A61B 5/00 |
| 2018/0110923 | A1 * | 4/2018 | Kaplan | A61M 5/20 |
| 2018/0126075 | A1 * | 5/2018 | Kaplan | A61K 31/44 |
| 2020/0101225 | A1 | 4/2020 | O'Connor | |
| 2020/0402651 | A1 * | 12/2020 | Nesterenko | G16H 40/20 |
| 2021/0121096 | A1 | 4/2021 | Gollakota | |
| 2021/0154410 | A1 | 5/2021 | Olivas | |
| 2021/0290184 | A1 * | 9/2021 | Ahmed | A61B 5/0008 |
| 2021/0319872 | A1 * | 10/2021 | Valentine | G16H 40/67 |
| 2021/0402083 | A1 | 12/2021 | Gibson | |
| 2022/0027018 | A1 * | 1/2022 | Tan | A61M 5/16877 |
| 2022/0062542 | A1 | 3/2022 | Nazzaro | |
| 2022/0080121 | A1 * | 3/2022 | Rosinko | A61M 5/142 |
| 2022/0203023 | A1 | 6/2022 | O'Connor | |
| 2022/0305202 | A1 * | 9/2022 | Rosinko | G06Q 30/0633 |
| 2023/0138098 | A1 | 5/2023 | Telfort | |
| 2023/0248614 | A1 * | 8/2023 | Aon | A61J 7/0418<br>700/242 |
| 2023/0372610 | A1 * | 11/2023 | Coyne, III | A61M 39/286 |
| 2024/0074701 | A1 * | 3/2024 | Hite | A61B 5/6805 |
| 2024/0245354 | A1 * | 7/2024 | Davoudi | A61B 5/0006 |
| 2024/0285206 | A1 * | 8/2024 | Chung | A61B 5/165 |
| 2024/0428918 | A1 * | 12/2024 | Theodorou | C12Y 304/24069 |

FOREIGN PATENT DOCUMENTS

| | | | |
|---|---|---|---|
| WO | 2023/028585 | A2 | 3/2023 |
| WO | 2023/212000 | A1 | 11/2023 |

OTHER PUBLICATIONS

Dhowan et al., "Simple Minimally-Invasive Automatic Antidote Delivery Device (A2D2) Towards Closed-Loop Reversal of Opioid Overdose", Nat. Lib. Of Medicine, 2019.

Lingamoorthy et al., "Dove: Shoulder-Based Opioid Overdose Detection and Reversal Device", 2025.

Nikkonen et al., "Artificial neural network analysis of the oxygen saturation signal enables accurate diagnostics of sleep apnea", https://www.nature.com/articles/s41598-019-49330-7, Scientific Reports, Sep. 2019.

Renesas Application Note, Pulse Oximeter Algorithm for SpO2, Heart Rate, and Respiration Rate, OB 1203, R36AN0001EU0301, Apr. 2022.

Yetisen et al., "Wearables in Medicine", Advanced Materials, 2018.

* cited by examiner

REMOTE MONITORING BASED WEARABLE APPARATUS AND RELATED METHOD FOR OPIOID OVERDOSE DETECTION AND ANTIDOTE DELIVERY

FIELD OF THE DISCLOSURE

The present system relates to a respiratory monitoring system that can interact with an opioid user and initiate a life-saving drug-injection process to mitigate opioid induced respiratory depression (OIRD) in an opioid user when OIRD is detected and, more particularly, to a wearable system that acquires information from an opioid user during an opioid use session, analyzes the information to detect the presence of OIRD in the opioid user, and initiates a lifesaving drug injection process when the presence of OIRD is detected, and a method of operation thereof.

BACKGROUND OF THE INVENTION

Opioids have many medical uses such as pain relief, anesthesia, and control of diarrhea as well as non-medical uses such as recreation in that they may produce a desired euphoric effect. Opioids have many adverse reactions chief of which is respiratory depression, e.g., opioid-induced respiratory depression (OIRD), which can lead to severe injury or death especially if a user suffers from comorbidities. Unfortunately, opioids can be addictive, with long term use often leading to increased tolerance and physical addiction, the latter being extremely difficult to cure because of many undesirable withdrawal effects. When opioids (which as used herein may include opiates, synthetic, and/or semi-synthetic opioids and/or the like) are used simultaneously with other drugs, the adverse effects of opioids can be greatly exacerbated. For example, when opioids are taken simultaneously with XylazineTM mixed with fentanyl (aka "Tranq"), the risk of OIRD increases significantly.

Further, individuals may often use opioids in a mobile, private, remote, or inconspicuous location in which others cannot observe the user. Thus, if the user suffers an adverse reaction to the opioid such as OIRD, it can be difficult to detect and render timely aid to the user. Thus, identifying the onset of OIRD can be challenging and, if not caught in time, can increase the chance of an undesirable outcome such as severe injury or death. Further, even when alerted of an opioid user in OIRD who requires immediate emergency services, it may be difficult to find this opioid user if an exact address and/or location is unknown such as may occur when opioid user is located in a remote location (e.g., off-the-grid) and/or in a large urban area where there may be many people at a single location and/or there may be multiple dwellings at a single address. Accordingly, embodiments of the present system overcome these and other disadvantages in the prior art and can initiate a life-saving drug injection process to prevent and/or to mitigate effects of the OIRD and contact emergency responders to provide assistance to the opioid user when time is of the essence.

Accordingly, there is a need to monitor an opioid user to diagnose the early onset of OIRD and respond accordingly to provide lifesaving aid to an opioid user. Further, there is a need to monitor an opioid user in a remote location that may be off the grid in which cellular communication and internet services may be unavailable and to render lifesaving aid to prevent or reduce the effects of OIRD in a timely manner. It should also be appreciated that monitoring of an opioid user may be performed without being present in a supervised injection site (SIS) or drug consumption room (DCR) while benefiting from the same similar harm prevention.

SUMMARY OF THE INVENTION

The present invention is a novel and useful wearable device system and related methods for diagnosing the early onset of opioid-induced respiratory depression (OIRD) and responding accordingly to provide lifesaving aid to an opioid user. The system(s), device(s), method(s), arrangements(s), interface(s), computer program(s), processes, etc., (hereinafter each of which will be referred to as system, unless the context indicates otherwise), described herein address problems in prior art systems.

The present invention can interact with an opioid user and initiate a lifesaving drug injection process to mitigate opioid induced respiratory depression in an opioid user when opioid induced respiratory depression is detected. The system and methods include a wearable device that acquires physiological and other information from an opioid user during an opioid use session, analyzes the information to detect the presence of opioid induced respiratory depression in the opioid user, and initiates a lifesaving drug injection process when the presence of opioid induced respiratory depression is detected. Several methods are disclosed including self-monitoring and remote monitoring schemes that present a challenge to the opioid user with post injection stimulation of the opioid user and notification of caregivers and medical personnel.

There is thus provided in accordance with the invention, a method of detecting and treating an opioid overdose in an opioid user for use in a wearable, the method comprising receiving and analyzing data from at least one physiological sensor to detect respiratory distress in the opioid user indicating a possible opioid overdose, notifying a monitor caregiver of the possible opioid overdose based on the data analysis, in response to a command from the monitor caregiver, injecting the opioid user with an opioid antidote via the wearable, and providing a periodic external stimulus to the opioid user after injection of the opioid antidote, the stimulus cancellable thereby.

There is also provided in accordance with the invention, a method of detecting and treating an opioid overdose in an opioid user for use in a wearable, the method comprising monitoring the opioid user for respiratory depression utilizing at least one sensor, if the level of respiratory depression exceeds a threshold, notifying a monitor caregiver of a possible opioid overdose and periodically presenting the opioid user with a challenge, upon failure of the challenge, notifying the monitor caregiver of an overdose of the opioid user, and in response to a command from the monitor caregiver, injecting an opioid antidote into the opioid user.

There is further provided in accordance with the invention, a method of detecting and treating an opioid overdose in an opioid user for use in a wearable, the method comprising periodically presenting a challenge to the opioid user after initiating use of an opioid, upon failure of the challenge, notifying a monitor caregiver of a possible overdose of the opioid user, in response to a command from the monitor caregiver, injecting an opioid antidote into the opioid user, and providing a periodic external stimulus to the opioid user after injection of the opioid antidote, the stimulus cancellable thereby.

BRIEF DESCRIPTION OF THE DRAWINGS

The present invention is explained in further detail in the following exemplary embodiments and with reference to the figures, where identical or similar elements may be partly indicated by the same or similar reference numerals, and the features of various exemplary embodiments being combinable. It should be expressly understood that the drawings are included for illustrative purposes and do not represent the scope of the present system. It is to be understood that the figures may not be drawn to scale. Further, the relation between objects in a figure may not be to scale and may have a reverse relationship as to size. The figures are intended to bring understanding and clarity to the structure of each object shown, and thus, some features may be exaggerated in order to illustrate a specific feature of a structure. In the accompanying drawings, like reference numbers in different drawings may designate identical or similar elements, portions of similar elements and/or elements with similar functionality. The present system is explained in further detail, and by way of example, with reference to the accompanying drawings which show features of various exemplary embodiments that may be combinable and/or severable wherein.

DETAILED DESCRIPTION

Figure 1:
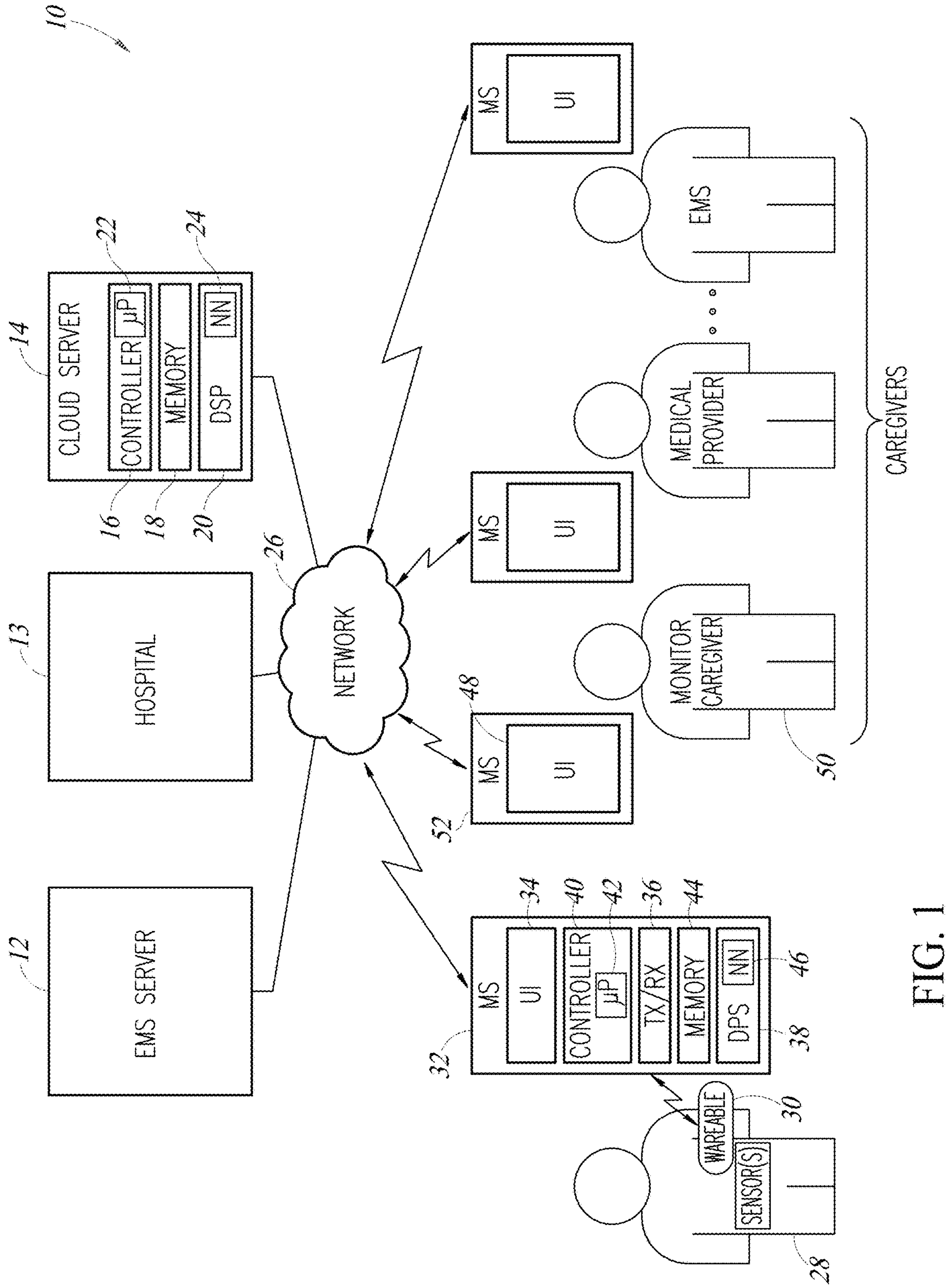
FIG. 1 is a block diagram illustrating a first embodiment of an opioid user monitoring system constructed in accordance with the present invention.

In the following detailed description, numerous specific details are set forth in order to provide a thorough understanding of the invention. It will be understood by those skilled in the art, however, that the present invention may be practiced without these specific details. In other instances, well-known methods, procedures, and components have not been described in detail so as not to obscure the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary, for the understanding and appreciation of the underlying concepts of the present invention and in order not to obfuscate or distract from the teachings of the present invention.

Any reference in the specification to a method should be applied mutatis mutandis to a system capable of executing the method. Any reference in the specification to a system should be applied mutatis mutandis to a method that may be executed by the system.

Throughout the specification and claims, the following terms take the meanings explicitly associated herein, unless the context clearly dictates otherwise. The phrases "in one embodiment," "in an example embodiment," and "in some embodiments" as used herein do not necessarily refer to the same embodiment(s), though it may. Furthermore, the phrases "in another embodiment," "in an alternative embodiment," and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

The following definitions apply throughout this document.

The terms caregiver (CG), caregivers (CGs), and/or formatives thereof, may include an operator such as a monitor or a professional such as a doctor, a clinician, an technician, an expert, a first responder (e.g., emergency medical services (EMS)), a medical specialist, a technician, a technologist, and/or the like, who may interact with and may review information related to the opioid user (OU), information stored by the system, information generated by the system, information received by the system, and/or information accessed by the system such as electronic health records (EHRs), unless the context indicates otherwise. The CGs may be considered third-party monitors and, without limitation, may be considered to be remotely located unless the context indicates otherwise. In the present embodiments, the CGs may be considered to be remotely located relative to the OU for the sake of clarity. It should be understood, however, that the geophysical location of one or more of the CGs such as the EMS CGs and MP CGs may change relative to the OU when responding to an OD event.

The terms opioid user (OU), opioid users (OUs), and/or formatives thereof, may include any subject, individual or individuals who may receive any type of opioid use monitoring or assessment using systems, machines, processes, and/or methods operating in accordance with embodiments of the present invention unless the context indicates otherwise. In some embodiments, the OUs may form a group and/or subgroup of OUs. For the sake of clarity, it is assumed that the OU may receive substance monitoring and assessment in accordance with embodiments of the present system.

As used herein, the term overdose (OD) may refer to an opioid overdose event (ODE) or the like in which the OU may experience respiratory depression or the like.

A block diagram illustrating a first example of a portion of an opioid user monitoring system (hereinafter the system) is shown in FIG. 1. The system, generally referenced 10, includes an opioid user (OU) 28, and N caregivers (generally CGs 50) such as a monitor, a medical provider (MP), and an emergency medical services (EMS), in accordance with embodiments of the present system. The system 10 may include one or more of an emergency medical service (EMS) server 12, a cloud server (CS) 14, a network 26, mobile stations (MSs) such as a user mobile station 32 (UMS) and caregiver MSs (CGMSs) 52, and a wearable unit 30 (which may be referred to as a wearable for the sake of clarity), one or more of which may communicate with the other using any suitable communication method or methods such as wired, wireless, and/or optical communication methods over the network 26. For the sake of clarity, and without limitation, each of the CGs 50 may be assigned a corresponding MS such as CGMS 52. It should be understood, however, that each of the CGs may be assigned more than one MS if desired.

Similarly, for the sake of clarity, and without limitation, the OU is assigned a single MS. It should be understood, however, that the OU may be assigned a plurality of MSs if desired. Any additional MSs may be similar to the corresponding one of the MSs 32, 52.

The network 26 may include any suitable network or networks such as a body area network (BAN), e.g., a medical BAN (MBAN), a near field communication (NFC) network, a personal area network (PAN), a near me area network, a local area network (LAN), a wide area network (WAN), a telephony network, a cellular network, e.g., 3G, 4G, 5G, etc.), a controller area network (CAN), a network, etc. Without limitation, it is envisioned that networks employed by embodiments of the present systems may operate under any suitable technologies, network protocols and/or standards such as Wi-Fi, Zigbee, Z-wave, Bluetooth, mobile phone standards, etc. It is envisioned, however, that embodiments of the present system may also be operative with any other suitable type or types of network technologies, protocols, and/or standards.

The CS 14 may include one or more of a controller 16, memory 18, and digital signal processor (DSP) 20. The controller 16 may control the overall operation of the CS and may include one or more logic devices such as a microprocessor 22 and/or the like which may be local and/or distributed throughout the system 10. Accordingly, it is envisioned that any controller of the system may control the overall operation of the system if desired. The controller 16 may be operationally coupled to the memory 18, the DSP 20, the EMS server 12, the network 26, and the MSs 32, 52. The controller may include digital and/or analog circuitry and may be configured to execute instructions as may be stored the memory or other suitable memory of the system. The microprocessor 22 may include one or more logic devices such as a microprocessor(s), integrated circuit(s), such as application specific integrated circuit (ASICs), programmable logic device(s), and/or the like, and may control the overall operation of at least the CS and/or other portions of the system. The controller may be configured to access one or more memories of the system to obtain desired information therefrom such as, for example, system setting information (SSI), electronic health records (EHRs), sensor information (SI), operating instructions, etc.

In some embodiments, the controller may include one or more controllers and/or the like which may employ machine learning (ML) and/or artificial intelligence (AI) engines configured to process information generated by the system such as the sensor information (SI) in accordance with an optional corresponding model(s) and may store results in a memory of the system for later use and/or may update the mathematical models which may be employed by the system. The ML and/or AI engines may employ one or more models stored in a memory of the system when processing the information generated by the system. Further, the ML and/or AI engines may create, edit, and/or modify the models and store these models in a memory of the system for later use. Models may be selected based upon a profile information of the OU.

The DSP 20 may include one or more neural networks (NNs) 24 such as a convolutional neural network (CNN) operative under the control of the controller and which may receive information generated by the system such as sensor information (SI) from one or more sensors of the system, perform analysis of this information, and output results of the analysis which may then be rendered by a rendering device of the system for the convenience of one or more users of the system such as the OU and/or CGs, or may be stored in a memory of the system such as the memory 18 for later use and/or further analysis in accordance with embodiments of the present system. For example, the controller 16 may forward the output results of the analysis, e.g., overdose (OD) detected, OD suspected conduct further tests, no OD, etc., to one or more of the CGs in accordance with embodiments of the present system.

The memory 18 may include any suitable memory and may store information used and/or generated by the system such as, without limitation, system settings, e.g., system setting information (SSI), etc., operating parameters, system parameters, user information such as opioid user identification (OUID), opioid user setting information (OUSI), caregiver setting information (CGSI), opioid use event information (OIEI), models, weights, electronic health records (EHRs), and/or combinations thereof.

The EMS server 12 may be operative to control an emergency services system that may respond to a request for aid (RFA) generated by embodiments of the present system such as by the server 14 or other portions of the system such as the MSs 32, 52. The RFA may include information related to the opioid user such as opioid user identification (OUID), user location, e.g., geophysical location, physical address (e.g., 123 Any Street, Anywhere, Any State, USA), apartment number (e.g., 41B), suite number (e.g., suite 41), EHRs, and current SI which may include, for example, physiological information such as vitals, etc., as may be transmitted by the MS 32 to one or more of the EMS servers 12, the CS, and/or one or more of the MSs 52 in accordance with the SSI. The physiological information may include information such as one or more of peripheral oxygen saturation (SpO2) (pulse oximetry), end tidal CO2, chest wall muscle monitoring, capnography, contactless respiratory rate monitoring using ECG, radar, optical, or thermal sensors, body temperature, heart rate (e.g., pulse), respiratory rate, and blood pressure as may be provided by one or more sensors of the system. The peripheral oxygen saturation (SpO2) may be obtained by a pulse oximeter of the present system. The body temperature may be obtained by one or more temperature sensors of the system such as an infrared sensor of the system which may form corresponding infrared sensor information and provide this information to a controller of the system for further processing.

Regarding end-tidal carbon dioxide ($ETCO_2$) monitoring measures the level of carbon dioxide that is released at the end of an exhaled breath. $ETCO_2$ levels reflect the adequacy with which carbon dioxide ($CO_2$) is carried in the blood back to the lungs and exhaled. Capnography adds objective data to physical exam findings, which helps determine the severity of respiratory distress. CO2 is a byproduct of cellular metabolism, which gets transported in the blood to the lungs for elimination. The amount of CO2 at the end of exhalation, or end-tidal CO2 (ETCO2) is normally 35-45 mm HG.

In severe cases of respiratory distress, increased effort to breathe does not effectively eliminate CO2. This causes CO2 to accumulate in the lungs and more of it to be excreted with each breath (hypercapnea), which would cause the ETCO2 level to rise. Increased work of breathing and CO2 retention may eventually lead to respiratory arrest. Respiratory failure from fatigue may occur even when patients inhale enough oxygen, thus having a normal pulse oximetry reading. High ETCO2 helps predict respiratory arrest before a change in mentation and decompensation occur.

Contactless respiratory rate monitoring, entails radar, optical, or thermal sensors can be used in the wearable device. These monitoring methods are useful for users whose contact-based monitoring is technically difficult, uncomfortable, or considered cumbersome and associated with poor compliance. These methods estimate respiratory rate by measuring respiratory sounds, carbon dioxide levels in exhaled gases, respiratory gas flow, or changes in blood oxygen saturation ($SpO_2$). In the latter case, pulse oximetry evaluates the $SpO_2$ levels using photoplethymography, quantifying changes in the optical absorption properties of hemoglobin with oscillations in blood flow. The pulsatile photophlethysmogram captured with these sensors has been used to extract respiratory and pulse rate in addition to hemoglobin oxygen saturation. Multiple sensor bands may be used that are spread across the chest, to quantify rib cage and abdominal movement. The bands incorporate electrical wires, which are excited by low amplitude, high frequency alternating current. Other contact based methods employ fiber optics, flowmeters, acoustics or thermal sensors.

ECG derived respiratory rate measurement is another contact based monitoring technique. This method estimates respiratory rate using algorithms that model and quantify modulations in ECG voltage waveform morphology that are induced by chest movements during breathing. Algorithms are based on modeling the oscillations in QRS waveforms obtained from ECG signals gathered from sensors arrayed over the user's chest or by using these signals to estimate deviations in the axis of the heart caused by respiration.

Operation of the EMS server 12 may vary by geographic location (e.g., city-to-city, state-to-state, etc.) and may be selected (e.g., by the cloud server) based upon a current location of the OU as may be determined by the system. The OUID may be employed to identify the corresponding OU 1001 and/or location of the OU.

The MSs 32, 52 may include any suitable mobile station(s) such as a smartphone (e.g., iPhone™, Galaxy™, etc.), a personal digital assistant (PDA), a smart watch (e.g., Apple™ watch, Galaxy™ watch, etc.), a tablet (e.g., an iPad, etc.), a laptop computer, a vehicle telematics system (VTS), and/or the like, and may include one or more of a user interface (UI) 34, at least one controller 40, transceiver (Tx/Rx) 36, memory 44, and a DSP 38.

The transceiver 36 may be configured to communicate with the network 26 via any suitable connection such as a wired, optical, and/or wireless connections.

The MS 32 may be assumed to be registered to the opioid user and may include SSI for one or more OUs. The MSs 52 may be referred to as care giver MSs (CGMSs) that may be assigned to a corresponding CG of the CGs 50 such as the monitor, the medical provider, and the EMS.

The MSs 32, 52 may access only applications, information (e.g., EHRs, etc.), and/or sites which they are authorized to use as may be set forth by system setting information (SSI) and may be controlled by an authenticator of the system. In the present examples, it is assumed that the MS 52 of the monitor 50 may not access EHR of the OU while the MS of the medical provider may access the EHR of the OU. In this regard, it will be assumed that in the present embodiments, each of the registered caregivers, via their correspondingly registered MSs, may receive the same or different information related to OU and opioid use event information (OUEIs) as may be set forth in the caregiver setting information (CGSI) of the SSI. For example, the MS registered to the monitor (who is assumed not be a medical provider of the OU in the present embodiments) may receive certain information related to the OU such as physiological information (in real time such as vitals), event alarm information (EAI), OUID, OU location, OU contact information, but may not be able to access EHR of the OU. In contrast, the MS registered to the medical provider may access the information accessible to the MS registered to the monitor as well as EHRs of the OU. The MS registered to the EMS may access similar information as accessible by the MS for the sake of clarity.

The MS 32 may receive an input from the OU indicative of the start of an opioid use event (OUE) and, in response, the system may start a opioid use event process (OUEP) in which SI related to the QUE as well as inputs from the OU (e.g., in response to a challenge) may be acquired and processed in accordance with embodiments of the present system.

The MSs 32, 52, and/or the wearable 30 may be standalone units with their own power supply. The MSs and/or the wearable may each include at least one optional port such as a USB-C port and/or the like through which power and/or information may be exchanged with a coupled device. In some embodiments, one or more of the MSs, and/or the wearable may include a wireless charger and/or a solar charger configure to provide for wireless and/or solar charging and/or the like.

Each of the MSs may include a user interface (UI) 34 with which a user may interact with the corresponding MS. For example, the UIs of each of the corresponding MSs may provide one or more interfaces with which a corresponding user may interact with the system and may include, one or more of touch screen displays, hard and/or soft keys, optical sensors such as a cameras or the like, proximity sensors, infrared (IR) sensors, light detection and ranging (LIDAR) sensors, haptic devices, microphones, accelerometers, gyroscopes, and/or gravity sensors. Other user interfaces, however, may also be envisioned. For example, in accordance with some embodiments, the OU may interact with the system via the UI using, for example, touch inputs or gestures the latter of which may be sensed by one or more accelerometers, gyroscopes, and/or gravity sensors of the MS 1012 and/or the wearable 1016 while the former may be sensed by touch-screen displays and/or hard or soft keys of the MS 1012 and/or the wearable 1016. The MSs 1012, 1014-*n* may render information that is entered, stored, and/or generated by the system 1000 on the one of the interfaces of the system 1001 such as on the UIs 1030 of the MSs 1012 and/or the 1014-*n* and may await a response from a corresponding user. This response may then be processed in accordance with embodiments of the present system. Text-to-speech and/or speech-to-text converters may be employed to perform corresponding translations. Accordingly, a user may enter information such as a command using, for example, a voice input if desired.

In some embodiments, the system may select a UI for rendering information in accordance with a type of information to be rendered. For example, graphical information may be rendered on a UI including a display, audible information may be rendered on a UI including a speaker, and haptic information may be rendered on a UI including a haptic device such as a vibrator which may include a motor driving an eccentric rotating mass, a piezoelectric transducer, an electrode, etc. depending upon system configuration. In some embodiments, it is envisioned that a plurality of the one or more UIs may be employed to render information. For example, an alarm may be rendered on UIs including a display, a haptic device, and/or a speaker of the system. It is envisioned that the SSI may set forth rules for rendering information.

The operation of the MS will now be described in more detail. It is appreciated, however, that the MSs 32, 52 may be similar. Accordingly, reference will now be made to MS 32 wherein at least one controller 40 may include one or more logic devices, such as a microprocessor (μP), and may control the overall operation of the MS in accordance with embodiments of the present system. A Tx/Rx 36 may be controlled by the at least one controller 40 and may be operative to communicate with other portions of the system such as the EMS server, the CS, and the MSs 52 via the network to receive information therefrom and/or to transmit information thereto. The Tx/Rx may receive information such as sensor information (SI) from one or more sensors 42 of the system and provide the received sensor information (SI) to the controller for further processing and/or analysis.

The memory 44 may be similar to the memory 18 and may store information used, generated, acquired, and/or updated by the system and may be local and/or distributed throughout the system.

The DSP 38 may include a signal processing block that may employ one or more neural networks (NNs) 46 operative under the control of the controller and which may receive information generated by the system such as sensor information (SI) from one or more sensors of the system, perform an analysis of this information, and output results of the analysis which may then be rendered by a rendering device of the system for the convenience of one or more users of the system such as the OU and/or CGs, or may be stored in a memory of the system such as the memory 44 and/or 18 for later use and/or further analysis in accordance with embodiments of the present system. For example, the controller 40 may forward the output results of the analysis to one or more of the CGs in accordance with embodiments of the present system. The DSP 38 may be similar to the DSP 20. In accordance with some embodiments, the NNs may access models and/or weights from a memory of the system and may process information input thereto in accordance with one or more of the models and/or weights as may be set forth in the SSI. It is also envisioned that in some embodiments the NNs may include convolutional neural networks (CNNs).

The wearable may include at least one or more of a controller, a memory, a user interface (UI), a stimulator, an injector, and at least one sensor, one or more of which may be local and/or distributed relative to each other. The memory, the UI, the stimulator, the injector, and the least one sensor may be operative under the control of the controller.

The controller may communicate with one or more of the memory, the UI, the stimulator, the injector, and the injector. The controller may control the overall operation of the wearable and may include one or more processors such as a microprocessor.

The memory may store information used and/or generated by the system. The memory may further store operating instructions for the wearable and may be local and/or distributed throughout the system.

The UI 34 may include one or more of a display (e.g., a touchscreen display, etc.), hard or soft keys, a speaker, a display, a haptic device, configured to render information for the convenience of the user and/or receive an input from the OU.

The wearable may also include a stimulator comprising any suitable device configured to stimulate the OU using, for example, electrical, mechanical, and/or chemical stimulation. In some embodiments, it will be assumed that the stimulator may render a high voltage electrical signal or the like (e.g., provided by a high voltage generator such as a high voltage coil, a switching power supply, etc.) and apply this signal to the skin of the OU 1001 via one or more electrodes coupled to the high voltage generator.

The injector may include any suitable injector for administering a desired medication(s) which may include, at least in part, an opioid receptor antagonist or opioid antagonist (which may be commonly referred to as an opioid antidote) and/or combinations thereof, which may be configured to counter the effects of the opioid taken by the OU during a current OUE. Suitable opioid antidotes may include Naloxone™, Naltrexone™, Narcan™, Nalmefene™, Buprenorphine™, and/or mixtures thereof.

The opioid antidote may be auto injected when the system determines that the opioid receptor antagonist should be administered in accordance with embodiments of the present system. In some embodiments the opioid antidote may include any suitable life savings medication or medications to counter the effects of an opioid overdose. For the sake of clarity, the term opioid antidote may refer to any medication or combinations of medications which may include, at least in part, an opioid receptor antagonist configured to reverse the effects of an opioid overdose in the OU. Accordingly, it is assumed that the opioid antidote may include an opioid receptor antagonist configured to temporarily reverse respiratory depression caused by the opioid that may be present in the OU. In some embodiments, the wearable may include an key (e.g., hard or soft) and/or a button which may be selected to activate an injection process.

The injector may include any suitable injector type such as active type injectors, passive type injectors, and/or combinations thereof. During an injection process, at least one actuator may provide a force sufficient to cause a needle to extend a fixed or adjustable amount (e.g., 18 mm, etc.) relative to a periphery of the body of the injector. When the needle is fully or substantially extended, the at least one actuator may provide a force sufficient to pump a dose of the opioid antidote through the needle. In some embodiments the at least one actuator may include a single actuator.

In passive type injectors, the at least one actuator may include a spring or high pressure gas cylinder which, when triggered or otherwise released may provide a biasing force sufficient to extend the needle and pump a desired dose of the opioid antidote through the needle. The at least one actuator may further include an actuator configured to cause the at least one actuator to fire. At least another actuator such as a spring or the like may be provided to retract the extended needle and/or to extend a sheath over the extended needle.

With regard to active type injectors the at least one actuator may include an actuator such as a linear actuator (e.g., powered by any suitable motor or motors) configured to extend the needle at a desired speed and/or to retract the extended needle. The same or another actuator may pump a desired dose of the opioid antidote through the needle.

With regard to passive injectors, these injectors may include at least one biasing member (e.g., compressed gas and/or spring, etc.) that when fired (e.g., released from a cocked position) may be configured to provide a force sufficient to advance a needle (e.g., relative to the body of the injector) and/or a plunger during an injection process to inject the opioid antidote through the needle once the needle is advanced. Accordingly, the plunger may pump the opioid antidote through the needle after it has been substantially advanced relative to a body of the injector. An actuator may be configured to provide a force sufficient to fire the at least one biasing member to initiate an injection. In some embodiments, auto-injectors may include at least one dose of the opioid antidote.

The sensor suite may include at least one sensor such as at least one optical sensor such as a pulse oximetry type sensor, an electrode type sensor, a temperature sensor, a pressure sensors, an ultrasound sensor, etc. which may sense corresponding physiological parameters of the OU and may generate corresponding sensor information (SI). Example sensors include a pulse oximeter sensor, end tidal CO2 sensor, chest wall muscle monitor, capnography, contactless respiratory rate monitor, body temperature monitor, infrared sensor, heart rate monitor, blood pressure monitor, motion sensor, radar based sensor, optical based sensor, acoustic sensor, thermal based sensor, a respiration monitor belt, and a respiratory sensor.

The pulse oximetry sensor may include at least one optical emitter and receiver pair which may be configured in one or more of transmissive and reflective pulse oximetry configurations to obtain corresponding sensor information which may be processed to determine peripheral oxygen saturation (SpO2) and/or to generate at least one photoplethysmogram (PPG) that may be transmitted to a controller of the system for further analysis and/or stored in a memory of the system for later use. The pulse oximetry sensor may be positioned on any suitable location on the OU such as located on an extremity (e.g., finger, etc.) of the OU, on a chest strap, etc.

Pulse Oximetry

The PPG may be acquired by the system at one or more times such at the start of an OUE and/or after a threshold time has passed after the QUE such as at intervals of 30 seconds, etc., as may be set forth in the SSI. The PPG may be processed by a digital signal processor (DSP) such as a neural network (NN) processor of the system such as the NN 46 for further analysis. For example, the NN processor may analyze the PPG and generate a confidence score (CS) which may be normalized to vary between 0 and 1. The CS may then be compared to a respiratory threshold value (RTV) to determine whether it is likely that the OU is suffering from respiratory depression. Accordingly, if it is determined that the CS is less than the RTV the OU is not likely to be in respiratory depression; and if it is determined that the CS is greater than, or equal to, the RTV the OU is likely to be in respiratory depression.

Challenge Generator

In accordance with embodiments of the present system, the controller may render one or more challenges (on a rendering device of the system) at threshold challenge times such as every thirty seconds (e.g., although other times are also envisioned which may be periodic or nonperiodic) after the start of an QUE for duration of the QUE (e.g., ten minutes, etc.) or as may be set forth in the SSI. After each time the one or more challenges are rendered, the controller may then await a response from the OU for a threshold response time. The controller may then await a response from the OU. If it is determined that a response is received from the OU within the threshold response time, the controller may once again render the one or more challenges on the rendering device and await a response from the OU. If it is determined, however, that the response has not been received from the user within the threshold response time, the system may generate an OD alarm and may enter an OD alert mode (ODA). In some embodiments, the system may generate and transmit an alert to one users such as a monitor CG, EMS CG, and/or MP CGs depending upon system settings and/or configuration and may await a response therefrom. In some embodiments, in the OD alert mode, the system may trigger an injection of the opioid antidote depending upon system settings and/or configuration.

In some embodiments, during the OD alert mode, the system may continue to render the challenge and await a response from the OU and may render information indicating that stimulation (e.g., electric shock) and/or injection may begin in a threshold ODA time (e.g., 10 seconds, etc. as may be set in the SSI) unless a response to the challenge is received within the threshold ODA time (e.g., 10 seconds). The controller may then await a response from the OU during this threshold ODA time. If it is determined that a response is received from the user within the threshold ODA time, the controller may once again render the one or more challenges on the rendering device and await a response from the OU. If it is determined that a response has not been received from the user within the threshold ODA time, the system may enter an OD alert mode (ODA). During the ODA, the system may perform one or more actions to interact with the OU and/or to administer a ORA to the OU as may be set forth in the SSI. For example, the system may activate the stimulator to shock the OU in an attempt to wake the OU from sleep or unconsciousness, and may activate the injector to administer an opioid receptor antagonist (ORA) to the OU.

Although a single wearable is shown, more than one wearable may be employed each being the same or different from each other. For example, with regard to wearables having different functionality, in some embodiments it is envisioned that a first wearable may include one or more sensors and/or the stimulator and the second wearable may include the injector.

Figure 2:
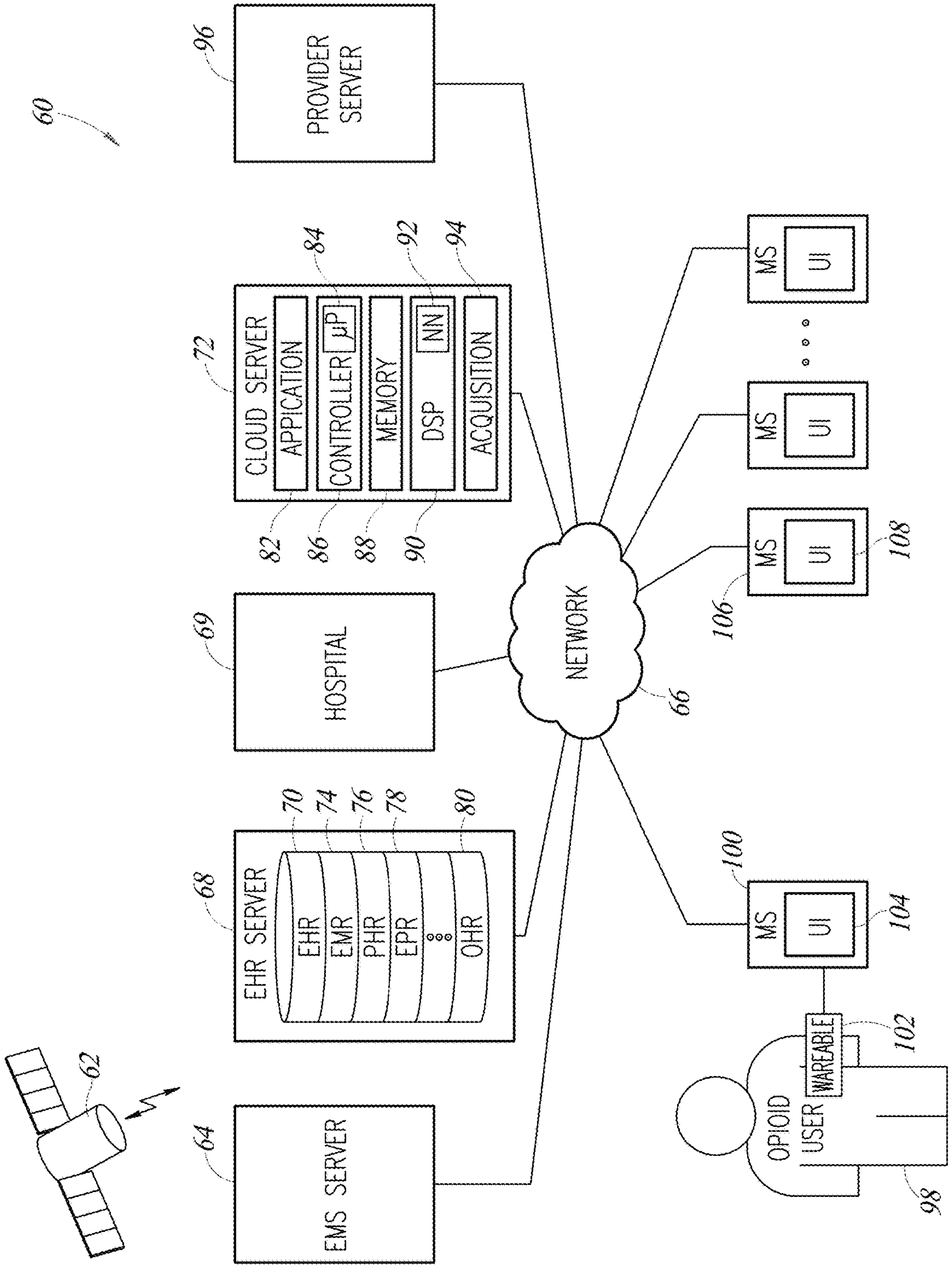
FIG. 2 is a block diagram illustrating a second embodiment of an opioid user monitoring system constructed in accordance with the present invention.

A block diagram illustrating a second example of an opioid user monitoring system is shown in FIG. 2. The system, generally referenced 60, may be similar to the system 10 (FIG. 1) and may include one or more of the EMS server 64, an electronic health record (EHR) server 68, the CS 72, a provider server 96, an application 82, an acquisition module (AM) 94, network 66, mobile stations 100 and 106, a location system 62, and wearable 102, one or more of which may communicate with the other using any suitable communication method or methods such as wired, wireless, and/or optical communication methods over the network.

The EHR server 68 may include any suitable storage, memory, database, etc. which may store information such as one or more records relating to a plurality of corresponding individuals such as electronic health records (EHRs) 70, electronic medical records (EMRs) 74, personal health records (PHRs) 76, electronic patient records (EPRs) 78; opioid use records (OURs) 80; proprietary records, and/or other records relating to corresponding individual such as a patient, the OU, etc. These individuals may form a population of individuals such as patients and/or OUs. For the sake of clarity, it will be assumed that the EHRs may include one or more of the EMRs, PHRs, EPRs, OURs, and/or the like. Each of the one or more of the EMRs, PHRs, EPRs, OURs may record information related to a corresponding interaction (e.g., a physiological interaction, etc.) with a corresponding individual such as a patient, the OU, etc.

For example, an EMR may be created to record an interaction (e.g., a physiological interaction) with a corresponding patient, and an OUR may be created to record a interaction with an OU (who may or may not be patient) during an OUE and may include corresponding OUEI. The created records (e.g., the EMR and/or the OUR) may then be stored in a memory of the system such as in the EHR of the EHR server. Thus, for the sake of clarity, it will be assumed that in the present embodiments each OUR for a OU may be stored in that OU's EHR in the EHR server. Accordingly, each QUE may be recorded as an OUR and may be stored in the EHR of the EHR server or in some other memory as may be set by the SSI. The PHRs may include information entered by an individual (e.g., the patient and/or OU) that may be controlled by the individual.

In some embodiments, it is envisioned that the OURs for a corresponding OU may be stored in a memory independent of the EHR if desired as may be set in the SSI. This may be desirable in cases where the OURs may not correspond with record acquisition and/or storage, and/or collection requirements set forth for EHR records by one or more regulatory bodies and/or standards. It is also envisioned that certain users of the system may not desire to store their OURs in the EHR, may not have an established EHRs such as guests, undocumented individuals, OUs outside of a certain location (e.g., in a foreign country, etc.), etc. Accordingly, in some embodiments, users (e.g., the OU, CGs, etc.) may be provided with one or more options to select a type and/or location of memory to store a corresponding OU's OURs such as in the EHR server, in a local memory (e.g., on the OU's MS, etc.), a CG's MS, etc. The user's settings may then be stored in the SSI for later use.

It is also envisioned that embodiments of the present system may set various system settings and/or parameters based upon the OUs location (e.g., country) and/or locations of portions of the system (e.g., storage devices such as databases, etc.) such that operation of embodiments of the system may conform with any applicable rules, requirements, regulations, and/or the like based upon location of the OU and/or portions of the present system such as memories, processors, etc. For example, it is envisioned that EHRs may correspond with formats set forth by the one or more governing bodies depending upon location of the corresponding EHR.

In the present embodiments, it will be assumed that each OUR may include OUEI information (OUEI) related to a corresponding OUE for the corresponding OU such as UID, and one or more of: start and stop times (e.g., of each OUE), information generated during the OUE by the system such as the SI, video, audio, calculations, determinations (e.g., OD detected, OD suspected, no OD detected, respiratory depression (RD) detected, RD not detected, RD suspected, etc.), graphs, user entries (e.g., from OU, CGs, etc.), etc. as may be set forth in the SSI. The SI may include detected physiological information such as blood pressure, heart rate, SpO2, PPGs, respiratory rate (e.g., breaths/minute), drugs delivered, alarms, etc. Information contained in the OUEI may be fixed and/or as set forth in the SSI.

The EHR server may include an anonymizer configured to anonymize and/or pseudonymize one or more selected EHRs and/or portions thereof (e.g., EMRs, PHRs, EPRs, OURs, etc.), for retrieval, analysis, storage, transmission, etc., depending upon system settings as may be set forth in the SSI.

The EHR server may be queried to acquire EHRs for one or more individuals such as the OU and/or groups of individuals such as groups of OUs, and/or a certain cohort, etc. For example, EHRs may be acquired for a group of OUs or subgroup such as OUs between the ages of 25-45 years-of-age, having certain medical conditions, comorbidities, etc., as may be selected by a user and/or the system.

The EHR server may include an aggregator configured to communicate with one or more portions of the system such as the EMS server, EHR server, CS, PS, AM, network, mobile stations, location system, and wearable to acquire information related to OUEs for each corresponding OU such as OURs and/or portions thereof (e.g., OUEI, SI, etc.) and may form and/or update a corresponding OUR which may be stored in the EHR of the EHR server depending upon system settings as may be set forth in the SSI.

The provider server 96 may include a server of an organization or the like which may provide opioid based services to the OU such as a hospital, an addiction clinic, a social services agency, a rehab clinic, a safe injection site, a safe injection facility, a self-injection facility, an overdose prevention center, a religious organization, and/or the like. The provider server may be configured to provide an interface with which the MS of the OU and/or the MS of the CGs may interact with the system to, for example, setup accounts, authorizations, login, acquire and/or change passwords, change account settings, etc. During an OUE, the provider server may be notified by the MS of the OU and may communicate in real time with one or more of the MSs depending upon system settings as may be set forth in the SSI. The provider server may be controlled by at least one controller of the system.

During an QUE, the location system 62 may determine location of the MS of the OU using any suitable method or methods such as, inter alia, global positioning system (GPS) methods, assisted GPS (AGPS) methods (e.g., using radio navigation methods), network based methods, handset based methods, triangulation methods, Wi-Fi methods, and/or the like. For example, the MS may determine its position using GPGs methods when available and transmit location information identifying the determined location to one or more portions of the system 60 such as to the cloud server 72, the EMS server 64, one or more of the MSs, etc., in accordance with the SSI. Accordingly, the location of the MS 100 may be transmitted to one or more first responders via their corresponding MS 106 for assistance when an OD is detected during an OUE. In some embodiments, if the location of the MS cannot be determined (such as when the MS is offgrid such as when in a location in which it cannot communicate with portions of the network 66 such as a cellular or mobile network, the Internet, etc.), the MS may render information of such for the convenience and safety of the OU on a rendering device such as on the UI 104 of the MS 100 and/or may render a request that the OU input a valid address on the UI. The MS may then await a response from the OU including information relating to the current location of the OU. The location of the MS of the OU may be updated in real time. In some embodiments, the MS of the OU may receive location signals such as GPS signals and/or the like from which it may determine a location of the MS when on or off grid.

The acquisition module (AM) 94 may be configured to communicate with one or more portions of the system to acquire information therefrom and/or to transmit information thereto. For example, in accordance with some embodiments, the AM may communicate with the EHR server to acquire desired information such as records relating to an OU, a group or subgroup of individuals as may defined by a cohort, etc. For example, the AM may obtain records such as one or more of EHR, EMR, PHR, EPR, OUR, the like, and/or portions thereof, for a particular time period, group or subgroup of individuals such as a cohort of opioid users of a certain age range, opioid dependence duration (e.g., starting opioid use, using opioids for one month, etc.), medication use (on, etc., or for a particular user of the system such as the OU.

In some embodiments, the cohorts may be matched to characteristics of the OU. Cohorts may be defined in the SSI and/or requested by a user such as one of the CGs and/or other authorized provider(s) which may, for example, request a thirty day time period. For example, in accordance with some embodiments, upon starting the application 82, the AM may be controlled to form a query for EMR and OUR for the OU for a desired time period such as the last thirty days, transmit this query to the EHR server, and may receive information corresponding to the query such as the requested EMRs and OUR for the OU for the past thirty days.

The received information may then be processed by one or more portions of the system such as the controller 86, the DSP 90, etc., in accordance with embodiments of the present system. In some embodiments, the AM may communicate with one or more MSs of the system, such as an MS, to acquire information therefrom related to the current OU such as such as OUID, SSI for the OU, the OUEI, OUR(s), etc., and may provide the acquired information to the controller for further processing and/or for storage in a memory of the system such as in the memory 88 and/or the EHR server. The AM may form the queries in any suitable format as may be employed by the system. The CS and/or the EHR server may include one or more anonymization engines configured to anonymize information that is to be transmitted and/or received (such as one or more of the EHR, EMR, PHR, EPR, OUR, etc.) in accordance with accordance with anonymization rules and/or settings of the system. In some embodiments, the SSI may set forth at least some of these settings.

The application 82 may be configured to run one or more processes, methods, routines, and/or the like of the system in accordance with embodiments of the present system. In accordance with some embodiments, when executing, the application may control the acquisition module to communicate with the MS of the OU to acquire SI therefrom which may then be processed to form processed information and may thereafter be provided to corresponding inputs of the NN 92 for processing in accordance with one or more optional models, algorithms, and/or weights provided by the application from a memory of the system such as the memory 88 and output a predicted overdose (OD) confidence value epsilon (E) which may be a normalized to have a value that is between 0 and 1 and may be referred to as a risk level. Higher levels of ε (e.g., higher risk levels) may indicate a higher confidence of the occurrence of an OD of the OU and lower levels of ε may indicate a lower confidence of the occurrence of OD of the OU. The process may then compare the value of ε with one or more confidence threshold values (CTVs) as may be set in the SSI. The values of the one or more confidence threshold values (CTVs) may be set by the system and/or a user (e.g., a CG) and may be stored in the SSI. The risk level may be adapted to indicate that respiratory depression of the opioid user is imminent.

In accordance with one embodiment, a single confidence threshold value CTV may be employed and may be set equal to 0.5. The process may then determine whether ε is greater than or equal to CTV. If it is determined that & is greater than or equal to CTV, the process may determine that an OD is likely. If it is determined that ε is not greater than or equal to than to CTV, the process may determine that an OD is not likely.

In accordance with yet another embodiment, the system may include first and second confidence threshold values CTV1 and CTV2, respectively, which may be given values of 0.33 and 0.66, respectively. Accordingly, the process may compare the value of ε with CTV1 and CTV2 to determine if ε is less than or equal to CTV1. Accordingly, if it is determined that ε is less than or equal to CTV1, the process may determine that an OD is not likely. Otherwise, the processes may determine whether ε is greater than CTV1 and less than or equal to CTV2. Accordingly, if it is determined that ε is greater than CTV1 and less than or equal to CTV2, the process may determine that an OD is likely (e.g., the process may determine that there is a high likelihood of an OD). Finally, if ε is greater than CTV2, the process may determine that there is a high likelihood of OD. Values for CTV, CTV1, CTV2, etc. may be obtained from a memory of the system and may be floating point numbers with a value between 0 and 1 and may be stored in the SSI. Values for CTV, CTV1, and CTV2 may be set to characterize levels of OD likelihood such as high level, medium level, or low level likelihood in the present embodiments. Once the likelihood of an OD is determined, results may be reported to the OU and/or CGs and may be stored in a memory of the system for later use and/or analysis.

Figure 3:
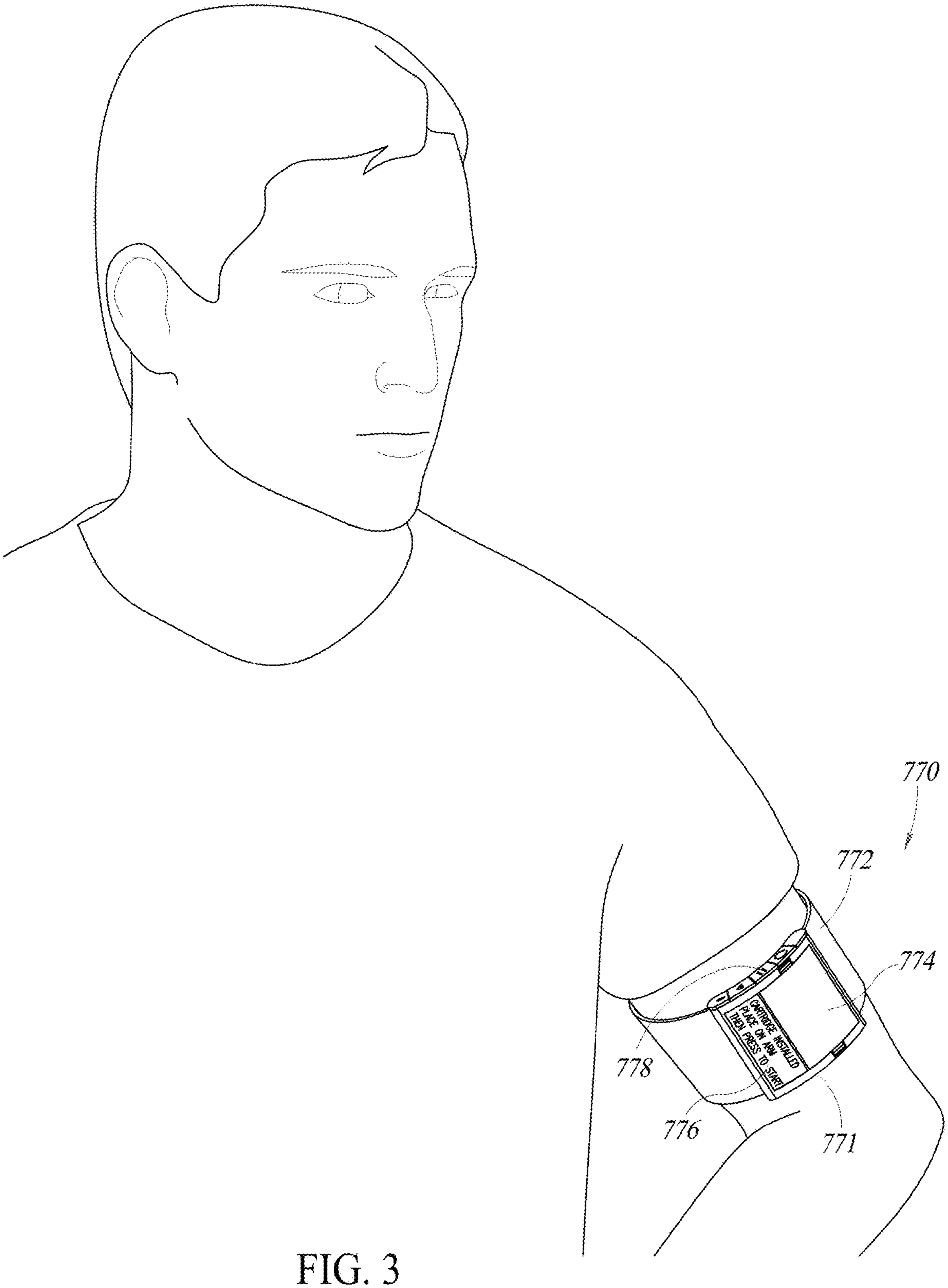
FIG. 3 is a diagram illustrating an example wearable device positioned on the arm of an opioid user.

A diagram illustrating an example wearable device positioned on the arm of an opioid user is shown in FIG. 3. The wearable, generally referenced 770, comprises a housing 771, adjustable band 772, replaceable drug cartridge 774, display 776, and a plurality of buttons, keys, keypads, etc. 778. The wearable is shown positioned on a user's arm similar to where a blood pressure cuff is typically placed. Alternatively, the wearable may be adapted to be worn on other positions on a user's body such as the wrist, forearm, leg, etc.

Figure 4:
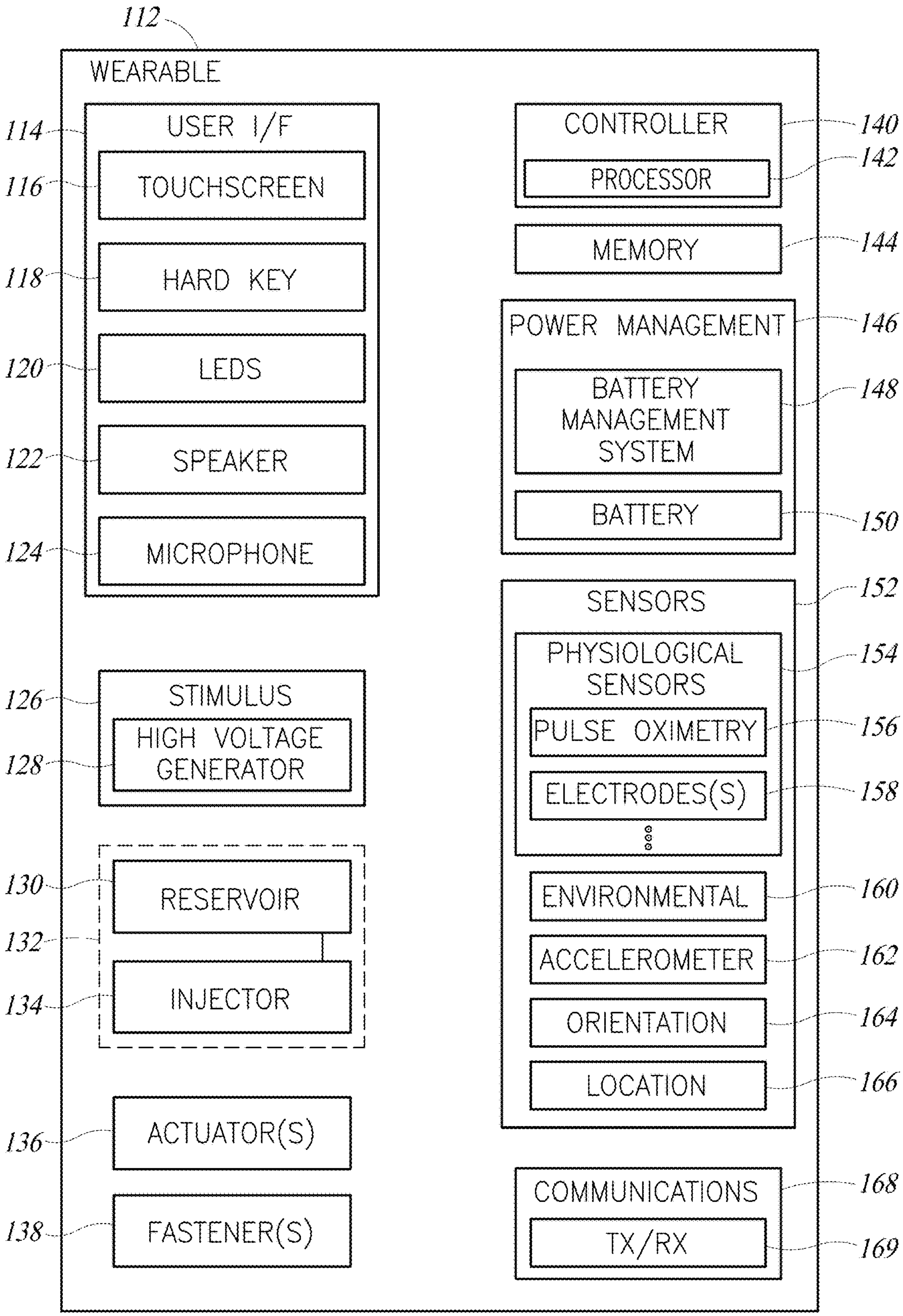
FIG. 4 is a block diagram illustrating an example wearable of an opioid user monitoring system.

A block diagram illustrating an example wearable is shown in FIG. 4. The wearable, generally referenced 112, is a key component of an opioid user monitoring system in accordance with embodiments of the present system. The wearable 112 may be similar to the wearable 30 (FIG. 1) and may include one or more of a user interface (I/F) 114, stimulus unit or shocker 126, injector 134, reservoir 130, controller 140, memory 144, power management unit 146, sensors 152, fasteners 138, actuators 136, and communications block 168, one or more of which may communicate with the other using any suitable communication method or methods such as wired (e.g., using a local bus, etc.), wireless, and/or optical communication methods over the network 26 (FIG. 1) and may be coupled to at least one of a body or housing 771 of the wearable.

The body may define at least a portion of at least one cavity configured to receive one or more of the stimulus unit, injector, reservoir, controller, memory, power management unit, sensors, the fasteners, and communications block. The body may be secured to a desired area of the OU by the fastener(s) which may be passive and/or active. The fastener may include a band that may be formed integrally with or separately from the body. The fastener may include a motor (e.g., linear or rotary controlled by the controller), buckle, rubber band, elastomeric band, hook and loop fastener (e.g., Velcro™, etc.), threaded coupling, snap fit coupling, and/or any suitable coupler. The fastener may include a sensor to sense when it is secured to the OU, form a signal indicating such, and transmit this signal to the controller for further analysis such as to determine when the fastener is sufficiently secured to the OU.

The body may include one or more openings extending therethrough and configured to receive one or more of the injector and the reservoir. A coupler may be provided to releasably couple one or more of the injector and the reservoir to the body. In some embodiments, an injection cartridge (IC) 132 may include a body including the injector and the reservoir and may be releasably coupled to the body of the wearable using any suitable coupler such as a threaded fastener, a latch, a snap fit joint, a bayonet-type fastener, an interference fit, etc. The IC may be coupled to one or more of the actuators to control an injection of the opioid antidote under the control of the controller.

The fastener may be coupled to the body and may be configured to position the body relative to the OU during use. The fastener may include an adjuster such as a hook and loop fastener (e.g., VELCRO™ or the like) configured to adjust a length and/or tension of the fastener. The fastener may include an adhesive strip or gel may be applied to an underside of the body which may be configured to releasably couple the body of the wearable to the OU. This gel may include a conductive medical grade gel and may be coupled to at least one electrode.

The memory may include any suitable memory or memories that may store operating instructions, algorithms, models, SSI, UI ID, health records (e.g., EHRs, EMRs, OURs, or portions thereof), SI, and/or information generated by the wearable for later use. The memory 144 may be similar to the memory 18 and/or 44 (FIG. 1) and may store information used, generated, acquired, and/or updated by the wearable and may be local and/or distributed throughout the system.

The controller may be control the overall operation of the wearable and may include one or more logic devices such as a microprocessor 142 and/or the like which may be local and/or distributed throughout the wearable. The controller may be configured to execute instructions such as operating instructions which may be stored in a memory of the system such as the memory or other suitable memory and may perform arithmetic operations in accordance with embodiments of the present system and may include digital and/or analog circuitry. The microprocessor may control the overall operation of the controller and may include one or more of arithmetic, logic, and/or control circuitry configured to perform one or more functions of a central processing unit (CPU). The microprocessor may include one or more processors such as a general purpose processor including a plurality of functions at least one of which may be operative in accordance with embodiments of the present system. In some embodiments, the microprocessor may include a graphics processing unit (GPU), a digital signal processor, a neural processing unit (NPU), and/or the like.

The power management portion may include one or more of a battery management system (BMS) 148 and a power source such as a battery 150 (or capacitor or other power storage device) and may be configured to provide power to one or more portions of the wearable such that the wearable may be operative as a standalone unit with its own power. For the sake of clarity, the power source will be assumed to include only the battery in the present embodiments although other energy storage devices such as capacitors are also envisioned. It is also envisioned that the battery may include a plurality of batteries that may be local or distributed relative to each other. In some embodiments, the power management portion may manage power to one or more portions of the wearable in accordance with an operating mode. For example, the wearable may have on, off, asleep, low power, and operating modes in which power may be provided to portions of the system in accordance with system settings. In the low power mode power may be provided only to select portions of the system as may be set forth in system settings. In the off mode power may be completely off or may be provided to certain portions of the system such as an on/off switch (if required) and/or one or more sensors as may be set forth in system settings.

The power management portion may include a charging port configured to receive power from an external source suitable for charging the battery. The charging port may include any suitable type of port such as a USB port (e.g., USB-C, micro USB, etc.), Lightning port, Thunderbolt port, wireless port, magnetic charging port (e.g., MagSafe or other inductive charger), and/or proprietary port and may be located at or near a periphery of the body.

The power management portion may include one more sensors configured to monitor one or more of voltage, current, and temperature (Tbatt) of the battery, form corresponding information, and provide this information to the controller and/or BMS. The BMS may be configured to monitor health, state of charge, number of cycles, voltage, current, charge, and balance, of the battery and may be configured control power to and/or from the battery accordingly. In some embodiments, a heater may be provided to warm the battery to operating temperatures. For example, the controller may determine whether Tbatt is less than a threshold operating temperature (Top). If it is determined that Tbatt is less than Top, the controller may be operative to turn on the heater to warm the battery. If it is determined that Tbatt is not less than Top, the controller may be operative to turn off the heater. This may be beneficial when operating in outdoor or other environments where power storage of the battery may be adversely affected below certain temperatures. The controller may render an indication of battery temperature for the convenience of the OU and may provide an interface with which to adjust battery heater settings (e.g., on, off, etc.) which settings may be stored in the SSI. In some embodiments, portions of one or more processes may not start until temperatures of one or more temperature monitored portions of the system are within an operating temperature range or ranges. Heaters may be provided to warm certain portions of the system when it is determined that a corresponding portion of the system is below a threshold temperature.

The BMS may provide information relating to charge of the battery to the controller for further analysis and/or for rendering on a rendering device of the system such as on a touchscreen 116, light emitting diodes (LEDs) 120 of the user I/F and/or on a display of the MS of the OU. The controller may be configured to render information relating to charge using one or more colors to indicate an available power level such as green for fully charged, yellow for charge soon, and red for insufficient charge (must be charge now). The controller may provide a user interface with which the OU may interact to view, set, and/or reset power settings and may initiate a power saving mode to reduce a load on the battery when it is determined that the charge of the battery is below a threshold value that has been determined assure proper operation of the system. The touchscreen may include one or more displays one or more of which may be located for viewing and interaction with the OU during use if desired.

In some embodiments, the battery may be removed from the body for replacement and/or charging in which case portions of the BMS may be separated from the body. A coupler may be provided to couple the battery to the body.

The wearable may include a communication port configured to enable communication with other portions of the system and may be combined with, or separate from, the charging port. In the present embodiments, however, it is assumed that the communication and charging ports are integrated. For example, a USB-C port, or the like, may be provided for both communication and charging via a wired connection or the like.

The communication block 168 may include a Tx/Rx circuit 169 which may be controlled by the at least one controller and may be operative to communicate with other portions of the system such as the MS of the OU to receive information therefrom and/or transmit information thereto. The Tx/Rx may be configured to transmit and/or receive information from to one or more portions of the system such as the MS of the OU and/or wireless sensors. This information may include, for example, SI, SSI, operating instructions, operating status, etc. for operating in accordance with embodiments of the present system. The Tx/Rx may be configured to provide information that it receives to the controller for further processing and/or storage and may receive information from the controller for transmission to a desired receiver such as the wireless sensors and/or MS of the OU to conserve battery power. In some embodiments, the Tx/Rx may include a low power wireless transceiver or the like and may be configured to pair to one or more portions of the system to transmit and/or receive information therefrom. The Tx/Rx may transmit in real time or may transmit in transmission bursts to conserve power. Digital signal processing of the SI may be performed locally or remotely from the wearable.

The sensors 152 may include one or more sensors such as one or more physiological sensors 154, accelerometer 162, a position (i.e. orientation) sensor 164, location sensor 166, and environmental sensor 160, each of which may sense a corresponding parameter, form corresponding sensor information (SI), and provide this sensor information (SI) to the controller for further processing and/or storage. The one or more sensors may sense information on a periodic or non-periodic intervals under the control of the controller. In some embodiments, the controller may query a sensor of the one or more sensors to provide corresponding sensor information (SI). At least one signal conditioner may be provided to condition the sensor information (SI) prior to it being received by the controller with the conditioning being dependent upon a type of sensor information (SI) being conditioned. The one or more physiological sensors 154 may include one or more pulse oximetry sensors 156, one or more electrodes 158, respiration monitor belt (i.e. a chest belt), a respiratory sensor, and a microphone. Although other sensors are also envisioned as described supra. The one or more physiological sensors may be configured to sense corresponding physiological parameters of the OU, form corresponding sensor information (SI), and/or may provide this SI to the controller for further processing and/or storage. For example, the one or more electrodes 158 may couple to the skin of the OU and may sense electrical currents at the skin of the OU, form corresponding sensor information (SI) which may then be conditioned (e.g., by filtering, amplifying, rectifying, etc. as may be desired) and may then be provided to the controller for further processing. In some embodiments, the electrodes may be configured to couple to a snap type adhesive electrode such as a single use snap electrode or the like which may be employed for detecting signals on the skin of the OU such as EMG or ECG electrodes of the like. The snap electrode may include an adhesive layer and a conductive layer wherein the adhesive layer may be configured to adhere to the skin of the OU and the conductive layer may be configured to sense electrical currents on the skin of the OU where the electrode is attached. These electrical currents may then be conditioned (e.g., filtered, amplified, etc., by a signal conditioner) and thereafter provided to the controller for further processing. It is envisioned that the adhesive layer may secure the body of the wearable to the skin of the OU.

In some embodiments, the plurality of sensors may be situated apart from one another to prevent operational interference between the plurality of sensors and to assure proper operation of the sensors. In some embodiments and isolation switch may be provided to separate transmit and receive circuitry from each other to prevent interference between transmit (e.g., high voltage signals from the stimulus unit, etc.) and receive (e.g., senses surface signals such as ECG, EMG, and/or the like) from each other. Receivers such as signal processing circuitry and the like coupled to the electrodes to receive signals therefrom may be disabled to protect these receivers from damage when the stimulus unit is activated and transmits a high voltage signal waveform to the electrode(s). Accordingly, the system may be configured to shock the OU by applying a high voltage signal to the OU via the electrode(s).

The pulse oximetry sensor (pulse-ox sensor) may include at least one emitter and receiver pair which may be arranged in at least one of a transmissive or reflective pulse oximetry configurations configured to generate corresponding sensor information (e.g., pulse oximetry information) which may be processed to determine peripheral oxygen saturation (SpO2) of the OU and/or generate at least one photoplethysmogram (PPG) that may be transmitted to a controller of the system for further analysis and/or stored in a memory of the system for later use. The PPG may be in any suitable format such as an image format, a graph format, a streaming numerical format, etc. as may be set forth in the SSI. The controller may control the pulse oximetry sensor to sample at a sampling rate (e.g., 50 samples per second although other rates are envisioned) as may be set forth in the SSI to obtain pulse oximetry information sufficient to form the PPG at a desired time intervals as may be set forth in the SSI. For example, PPGs may be formed at the start of a OUE and thereafter every 5 seconds (although other latency times are also envisioned as may be set forth in the SSI).

In some embodiments, the one or more sensors may detect the presence and/or absence of one or more of the injector 134, reservoir 130, and injection cartridge (IC) 132, form corresponding sensor information and provide this sensor information to the controller for further processing such as to determine whether the one or more of the injector, reservoir, and injection cartridge (IC), are present and secured.

The accelerometer may detect acceleration of the wearable (or a corresponding portion thereof) along one, or about, one or more axes and form corresponding acceleration sensor information and provide this information to the controller for further processing.

The respiration monitor belt may measure movement of the chest and/or abdominal wall of the OU, form corresponding SI and provide this SI to the controller for further processing. The controller may then measure pulmonary ventilation of the OU based upon this SI using any suitable method such as respiratory inductance plethysmography (RIP) or the like.

The orientation sensor 164 may detect orientation (e.g., relative to a magnetic field such as the Earth's magnetic field), may form corresponding orientation sensor information, and may provide this information to the controller for further processing. In some embodiments, the orientation sensor may include a magnetic field sensor such as a magnetometer or the like.

The location sensor may employ any suitable method to determine location of the wearable such as GPS, A-GPS, triangulation, etc., may form corresponding location sensor information, and/or may provide the location sensor information to the controller for further processing such as to determine a location of the wearable and/or MS of the OU. In some embodiments (e.g., those employing A-GPS and the like) location of the wearable 3016 may, at least in part, be determined remotely from the wearable and transmitted to the wearable. It is further envisioned that in some embodiments, when location information may be unavailable such as in remote and/or shielded locations, the system may estimate a current location of the wearable and/or MS of the OU based upon acceleration and/or orientation information and a known past location of the wearable and/or MS of the OU. This may be useful shielded areas (e.g., large buildings, hospitals, etc.) and/or remote locations. In some embodiments the wearable and/or MS of the OU may provide an interface with which the OU may interact to enter a current location of the wearable and/or MS of the OU and the system may use this location as a current address.

In some embodiments, the controller upon receiving one or more of the acceleration sensor information, the orientation sensor information, and/or the location sensor information may analyze the corresponding sensor information and determine acceleration, orientation, and/or location, of the wearable, respectively, or may transmit the corresponding sensor information to the MS of the OU for further processing. This information may be useful to locate the wearable during on OUE especially when an OD is suspected, and/or to determine whether the wearable and thus OU is moving (e.g., walking, etc.).

In some embodiments, acceleration information may be mapped to one or more inputs of the system. For example, certain motions of the wearable and/or MS of the OU may be mapped to certain keys and/or commands such as a command to start an OU session, respond to an OU request (e.g., "OK"), etc. In some embodiments of the present system, the system may determine that the OU is not in respiratory depression when walking motion is detected through an analysis of the acceleration information from the wearable and/or MS of the OU. This mapping may be stored in the SSI. Thus, the system may monitor for movement of the wearable during an QUE and may determine that the OU is not suffering from an OD if, for example, the OU is walking, running, jogging, or otherwise engaging in physical activity, etc. as may be determined through analysis of one or more of the location, acceleration, and/or orientation sensor information.

A user interface (UI) may be provided for a user such as the OU and/or CG and/or system to map movements (e.g., walking, running, etc.) and/or actions (e.g., a chopping action, etc.) to corresponding inputs and the system may store this information in the SSI for later use.

UI 114 may be similar to UI 34 (FIG. 1) and may include one or more of a display such as a touchscreen 116, one or more hard keys 118 3033, speaker 122, microphone 124 and/or at least one LED 120 (such as solid, blinking, and/or multi-color LEDs) or other illumination source(s) with which the OU may interact with the wearable. For example, the touchscreen, hard key switch, microphone, speaker, and LEDs may be configured to render information generated by the system for the convenience of the OU under the control of the controller and the OU may enter information (e.g., commands, etc.) to the system via one or more of the touchscreen, hard key, LEDs, and/or microphone (e.g., using voice commands, etc.).

In some embodiments it is envisioned that the hard key may be combined with a corresponding LED to form a hard key that may be illuminated by the controller using one or more colors, etc. For example, the hard key may be illuminated by a corresponding one of the LED under the control of the controller when it is desired to inform the OU to respond and press the hard key. In some embodiments, the hard key may be mapped to a soft key which may be illuminated on the touchscreen concurrently with the hard key or in place of either key. Thus, the hard key may have a corresponding soft key or vice versa.

The reservoir may include any suitable container or assembly for containing the opioid antidote configured to counter the effect of an opioid taken by the OU. Accordingly, the opioid receptor antagonist may temporarily reverse respiratory depression caused by the opioid. The reservoir may be coupled directly, via a tube or hose, and/or a fastener (such as a Luer type fitting) to a hollow needle such as a hypodermic needle (hereinafter both of which may be referred to as a hypodermic needle unless the context indicates otherwise) configured to receive the opioid antidote. In some embodiments, the reservoir may be formed at least in part by a syringe and/or may include a coupled to a syringe. In some embodiments, the reservoir may include a prefilled syringe (PFS) having a cavity including at least one opioid antidote such as an opioid receptor antagonist. A stopper may seal the opioid antidote into the cavity at one end and the hypodermic needle may include a cover seal that may be configured to seal the opioid antidote from passing through the hypodermic needle until pierced by the hypodermic needle. In some embodiments, a cannula may be employed in place of hypodermic needle. In some embodiments, a heater operative under the control of the controller may be provide to heat the reservoir to a desired temperature range if desired.

The actuators 136 may be configured to trigger an injector to initiate an injection when using passive injectors and to control extension and/or retraction of a hypodermic needle and/or pumping of a opioid antidote when using active injectors. In some embodiments, couplers may be provided configured to couple the actuators to a portion of the injection cartridge to trigger the injection cartridge to inject the opioid antidote into the opioid user.

The injector may be configured to administer at least one dose of the opioid antidote from the reservoir via the hypodermic needle and may include an injection cartridge which may be disposable after use. In some embodiments depth of penetration of the hypodermic needle may be fixed or passively or actively adjustable for providing one or more of intramuscular and/or subcutaneous injection of the at least one dose of the opioid antidote from the reservoir. The injector may include one or more actuators configured to perform an injection process which may include acts of: advancing the hypodermic needle to a dispensing position (the cover seal may be pierced by the hypodermic needle at this point); administering a dose of the opioid antidote contained in the reservoir through the hypodermic needle when the hypodermic needle is in the dispensing position; and/or optionally retracting the hypodermic needle or activating a shield (e.g., a sheath) to cover the hypodermic needle after administering the dose of the opioid antidote through the hypodermic needle.

It is envisioned that the injection process may be passive or active. In some embodiments a plurality of injector such as passive and/or active injectors may be provided and may be of a single use disposable type in which one or more portions thereof may be of a single use type and disposable. In the present embodiments will be assumed to include a PFS including at least one dose of the opioid antidote and a hypodermic needle coupled thereto.

Passive injectors may perform the injection process automatically when triggered by the actuator (e.g., a triggering actuator) operative under the controller. The passive injectors may include one or more preloaded actuators such as springs, pneumatic cylinders and/or combinations thereof, which when triggered may be configured to advance the hypodermic needle to a dispensing position, pump a dose of the opioid antidote through the hypodermic needle, and withdraw the hypodermic needle or extend a sheath over the hypodermic needle. The actuators may be configured to trigger the desired injector.

The active injectors may include one or more actuators (e.g., including linear and/or rotary actuators and/or pumps) operating under the control of the controller and configured to advance the hypodermic needle to the dispensing position, administer the dose of the desired meditation when the hypodermic needle is determined to be in the dispensing position, and retract the hypodermic needle after administering the dose of the opioid antidote. Sensors may provide feedback to the controller via sensor information (SI) transmitted thereto continuously or at discrete points. For example, location of the hypodermic needle may be provided to the controller to indicate when the hollow needle is in a storage position and/or in the dispensing position (which may include a desired position or range of positions. The SI may be provided the controller as feedback information and controller may analyze the SI and control one or more actuators accordingly. The actuators may include linear and/or rotary actuators and/or motors such as linear or rotary motors such as DC motors, stepper motors, piezoelectric motors, and/or the like. The position of portions of the injector such as the hypodermic needle may be determined using any suitable sensor(s) such as linear encoders, rotary encoders, mechanical switches (such as micro switches or the like), audio sensors, ultrasonic sensors, and/or the like. the like.

In some embodiments, the injector may include an injection cartridge that may be disposable. In some embodiments, the wearable may include a plurality of injection cartridges each configured to administer one does of the opioid antidote. In some embodiments, the injection cartridges may include one or more actuators which may be passive and/or active and may be disposable after use.

The stimulus unit 126 when activated may provide a chemical, mechanical, and/or electrical shock to the OU under the control of the controller. The chemical shock may be administered by an injector or an atomizer configured to dispense a dose of a chemical stimulant to the OU. The injector may be configured to be operative to inject the OU with a desired chemical stimulant.

With regard to the electrical shock, when activated, the high voltage generator 128 of the stimulus unit may generate a series of high voltage signals, each having a desired waveform and amplitude, and which may be applied to the skin of the OU via a pair of electrodes to stimulate the OU via electric shock. The series of high voltage signals may have a duration (Thv=2 seconds, etc.) and may have a dwell time therebetween (Tdwell=5 seconds, etc.) during which the high voltage signal may be paused, as may set by the SSI and/or processes of the present system. Each of the series of high voltage signals may have a waveform type, such as a sine, square, sawtooth, and triangle, with an amplitude, frequency, and duty cycle (if applicable), which may be set in accordance with the SSI and/or processes of the present system. In some embodiments, the waveform may be changed each time it is repeated or in time. For example, in some embodiments, the amplitude and/or frequency of the waveform may be increased by a threshold amount (e.g., 10 volts, 5 Hz, respectively) each time the series of high voltage signals is repeated as may be set forth in the SSI and/or processes of the present system. This may increase the stimulation provided to the OU each time the electric shock is repeated. In some embodiments, the system may cycle through waveform types (e.g., from sine to square to sawtooth, etc.) each time the series of high voltage signals is repeated as may be set forth in the SSI and/or by embodiments of the present system. The voltage, waveform, and/or duty cycle may be selected to awaken the OU during an ODE.

When the stimulus unit is activated, the OU may render a selection item on the UI which when selected may be operative to stop the electrical shock (or chemical shock depending upon embodiments) applied to the OU via the electrodes. In some embodiments a button or key may be provided which may stop the electric shock when pressed.

In some embodiments, one or more of electrodes may be shared by two or more circuits in which case an isolator may be applied and activated to isolate the two or more circuits when the high voltage signals are generated to protect sensitive circuitry from damage due to high voltage being applied thereto. The isolator may be controlled by the controller and may be activated (e.g., toggled on) slightly before the high voltage signal is generated and deactivated (e.g., toggled off) slightly after the high voltage signal is no longer generated. It is also envisioned that acquisition and/or processing of SI may be suspended when the high voltage signal is applied to prevent erroneous date from being collected and processed by the system.

It is envisioned that the electrical shock provided to the OU may stimulate the OU to, for example, awaken the OU when asleep and/or experiencing an OD prior to the opioid antidote taking effectively countering respiratory depression caused by the opioid taken by the OU. For example, Naloxone may require several minutes to effectively counter the effects of the opioid taken by the OU.

The fastener may be configured to hold the wearable, or portions thereof, in position during operation. The fastener may be formed integrally with or separately from, the body of the wearable. The fastener may include a buckle or other suitable fastener to open, close, and/or remove the wearable such as a hook and loop fastener (e.g., VELCRO™, etc.), a snap fit fastener, a magnetic fastener, an interference fit, an elastic band, etc., which may enable quick and effortless coupling. In some embodiments, the fastener may be active of passive. It is envisioned that the fastener may be passive or may be active.

With regard to the active fastener, this fastener may include an actuator (e.g., a linear or rotary actuator) operative under the control of the controller to tension the fastener to a desired tension as may be set forth in the SSI. Sensors may be provided to sense the tension, generate corresponding SI and may provide this information to the controller for further processing such as to determine whether the fastener is closed, ready for operation, etc., and may render an indication of such on the UI for the convenience of the OU (e.g., "fastener closed," "close fastener," "more tension needed," "adjust fastener," etc.). The controller may render at least one selection item on the UI that may be selected (e.g., by the OU) to toggle the fastener open or closed (e.g., by varying tension accordingly). For example, in accordance with some embodiments as set forth in the SSI, the fastener may include one or more sensors which may sense when it is fastened securely (e.g., about the OU) and may form a corresponding fastened sensor information and provide this information to the controller. The controller may then determine whether the fastener is fastened. The controller may activate the wearable 3016 when it is determined that the fastener is fastened. If the controller determines that the fastener is not securely fastened, the controller may deactivate the wearable to conserve power and may render indication of such on the UI for the convenience of the OU. In some embodiments, the wearable may be activated at any time by depressing a power button which may transmit a corresponding signal to the controller which, in response, may activate the wearable.

Figure 5:
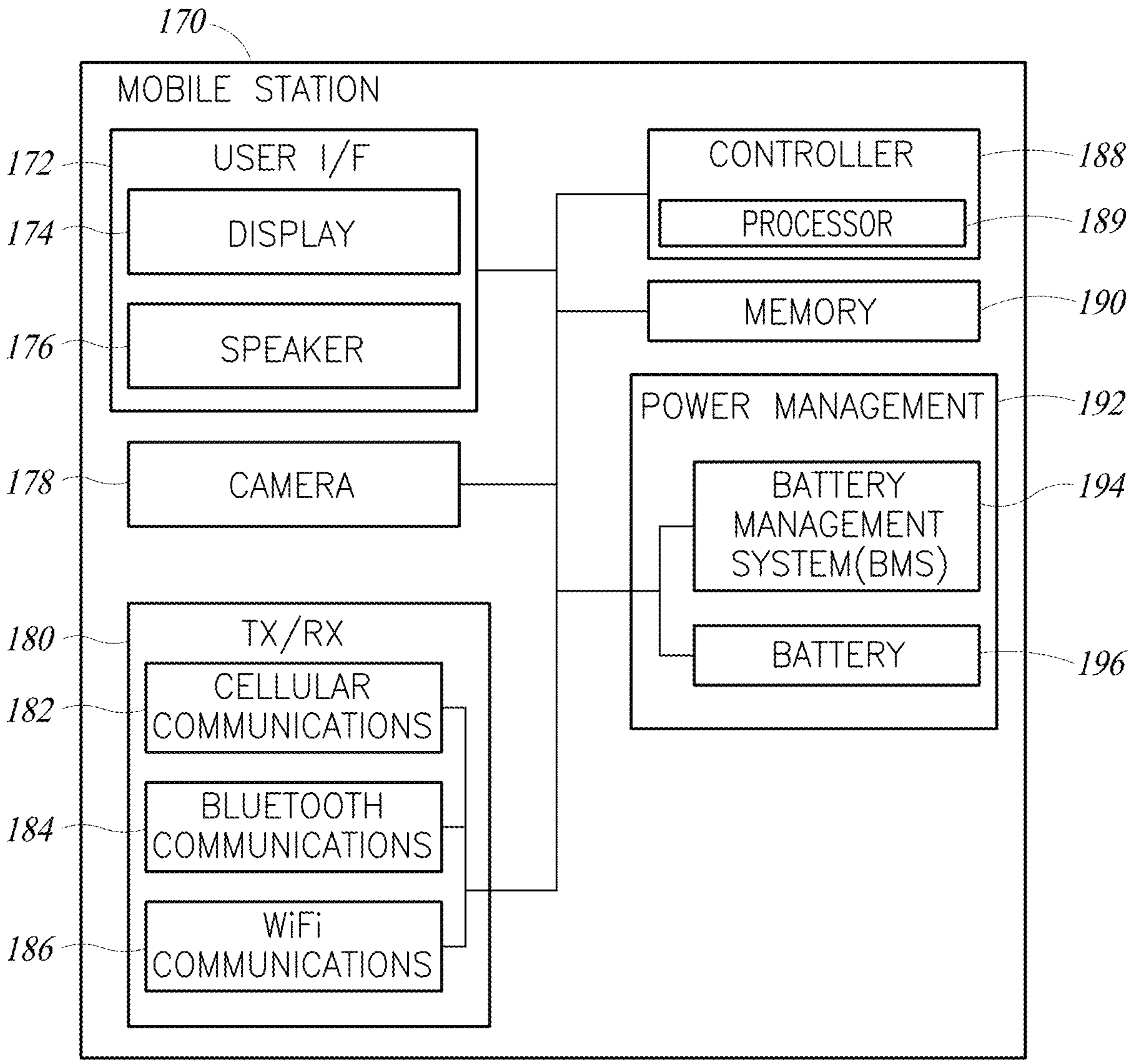
FIG. 5 is a block diagram illustrating an example mobile station (MS) of an opioid user monitoring system.

A block diagram illustrating an example mobile station (MS) in accordance with embodiments of the present system is shown in FIG. 5. The MS, generally referenced 170, may include one or more controllers 188, memory 190, image capture device such as a camera 178, power management block 192, UI 172, and transceiver (Tx/Rx) 180 one or more of which may communicate with each other using wired and/or wireless communication methods. For the sake of clarity, it may be assumed that the MS 170 may be similar to the MSs 52, 106 described with respect to FIGS. 1 and 2, respectively.

The power management block 192 may be similar to the power management block 146 (FIG. 4) of the wearable and may manage power throughout the MS. The power management block may include one or more power sources such as a capacitor and/or battery 194 configured to power the MS. A battery management system (BMS) 196 may be configured to manage charging and power draw of the battery. The may monitor and/or charge the battery and/or individual cells therein. The BMS 196 may communicate with the BMS 148 (FIG. 4) of the wearable to obtain information related to the battery of the wearable such as health, charge, etc. and may provide this information to the at least one controller 188 for rendering on the UI 172 for the convenience of the user. For example, the UI may render the information on a display 174 and/or a speaker 176. In some embodiments, BMS 196 and 148 may arrange for the transfer power therebetween so that a charge may be transferred between the batteries 194 and 150 in either direction using wired and/or wireless power transfer method(s) when desired. Accordingly charging may be performed away without the need of mains power.

The UI may include at least one of the display and the speaker each of which may be configured to render information under the control of the at least one controller. The display may include a touchscreen display configured to interact with the user (e.g., the OU) via a touch interface. The speaker may be configured to render audio information under the control of the at least one controller.

The camera 178 may be operative under the control of the at least one controller and may be configured to capture an image, for corresponding image information, and transmit this image information to the at least one controller for further processing, transmission via the Tx/Rx, rendering on the display, and/or storage in a memory of the system such as the memory for later use.

The Tx/Rx and may include one or more of a cellular communications portion 182, Bluetooth communications portion 184, and Wi-Fi communications portion 186 which may be configured to communicate with other portions of the system using cellular, Bluetooth, and Wi-Fi communication protocols, respectively, via network 26 (FIG. 1).

Wireless communication methods may vary by device. For example, in some embodiments, the MS may communicate with the cloud server 14 (FIG. 1) using Wi-Fi, may communicate with the MSs of CGs using cellular communications, may communicate with the wearable using Bluetooth. In accordance with some embodiments, the Tx/Rx may optionally include one or more of upconverters, downconverters, coder/decoders (CODECs), etc. Network protocols for transmission may be selected users (e.g., the OU), by the system in accordance with available networks, and/or in accordance with the SSI.

Figure 6:
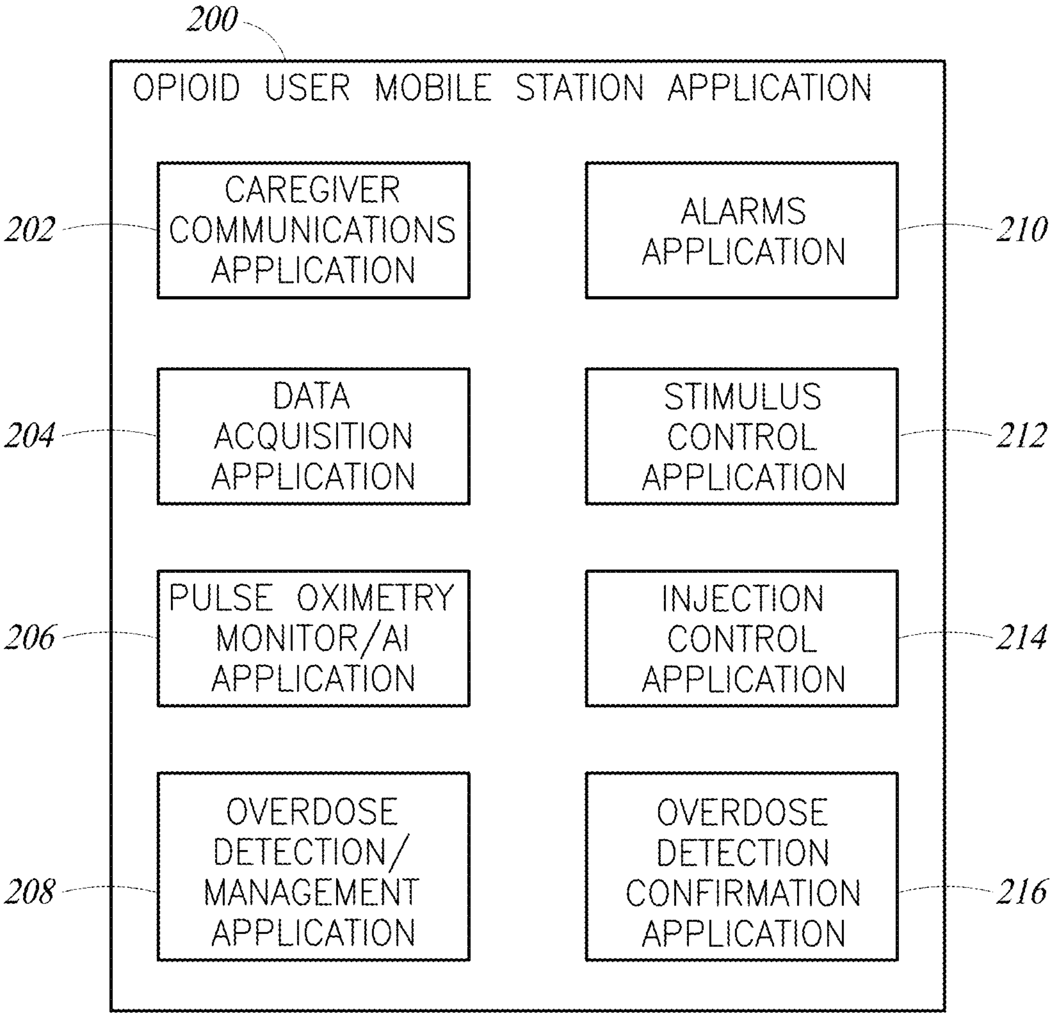
FIG. 6 is a block diagram illustrating the opioid user mobile station in more detail including example applications executing thereon.

A block diagram illustrating example applications running on the mobile station of the OU in accordance with embodiments of the present system is shown in FIG. 6. The applications, generally referenced 200 may include CG communications 202, shock control 212, data acquisition 204, injection control 214, pulse oximetry monitor/AI 206, OD detection confirmation 208, OD detection/management 216, and alarms 210 one or more of which may communicate and/or be combined with the other, and may be loaded, configured, and/or run by a controller of the system such as a controller of the MS of the OU.

In some embodiments, the MS may determine whether the start of an OUE is requested (e.g., by the OU via the UI) and at least one controller of the MS may load and/or run one or more of the applications upon determining that start of the OUE is requested. In some embodiments, one or more of the applications may be run during an initial setup prior to the start of an QUE and/or after the end of an QUE to, for example, to update system information and/or to store information in a memory of the system for later retrieval and/or use.

CG communications 202 may be configured to establish and/or control communications between MSs of one or more of the CGs and the OU for establishing and communicating an QUE and/or providing for medical assistance when an OD is detected. For example, prior to establishing an OUE or when an OUE is requested, the CG communications application may be configured to generate and render a user interface on the MS of the OU with which the OU may view a plurality of CGs and select at least one of the CGs to be selected CG for the QUE, and may establish communication with the selected CG for the QUE via any selected communication method(s) as may be selected by the OU and/or SSI such as voice call, video call, email, text messaging, social account (e.g., Facebook™, etc.), etc. It is envisioned that the CG communications application may be configured to establish communication with the EMS and/or medical provider, and/or other contacts such as a parent, a spouse, etc., of the OU, when an OD is detected as may be set forth the SSI. The CG communications application may be configured to provide communications and/or status of the OU to one or more of the CGs in real time during the QUE in accordance with the SSI. Similarly, the status of one or more CGs may be provided for selection by the OU for an OUE. CGs may grouped and/or sub-grouped and a rendering of such may be rendered on a UI of the MS of the OU for selection by the OU for a QUE. For example, the CGs may be selected from a group or subgroup of CGs that may be available for selection by the OU for an OUE and may be currently available or may be available at a future time (e.g., via scheduled) and may be selected by the OU, the system, and/or SSI for communication with the OU during an OUE and may establish communication with the OU and/or other CGs during an QUE.

In some embodiments, the CG communications application may communicate with the CS to establish communication with one or more of the CGs registered to, or selected by, the OU via their respective MSs 52 (FIG. 1). In some embodiments, the CG communications application of a CS server may establish communication directly with the one or more of the CGs registered to, or selected by, the OU via their respective MSs via a network of the system such as a cellular network, etc., as may be set by the SSI and/or OU.

The data acquisition application 204 may obtain sensor information (SI) from one or more sensors of the system such as such as pulse oximeter sensor information (SI) from a pulse oximeter sensor in contact with the skin of the OU. Data acquisition may provide the acquired sensor information (SI), to the pulse oximetry monitor/AI 206 for further processing. Data acquisition may communicate with one or more available sensors and/or with sensors set forth by the SSI to acquire SI therefrom. The SSI may set forth information indicative of sensors to acquire the SI from for a current OUE. The sensors may be selected by availability and/or in accordance with the SSI for a current QUE. In some embodiments, the data acquisition application may form queries and transmit these queries to one or more sensor of the one or more sensors to obtain sensor information therefrom. In some embodiments, the data acquisition application may receive SI at periodic or non-periodic intervals. The SI may be pushed, pulled, etc.

The pulse oximetry monitor/AI application 206 may receive the sensor information (SI), such as the PPGs, from the data acquisition application and may process the acquired sensor information (SI) to form processed information, and may feed the processed information to an AI engine including an NN processor such as a CNN process, that it controls for further analysis in accordance with one or more AI models and/or algorithms obtained from a memory of the system. The AI engine may then output a prediction which represents an overdose (OD) confidence value epsilon(s) which may be a normalized, by a normalization engine, to a value that is between 0 and 1 and provide this value to the OD detection/management application 208 for further analysis.

The OD detection/management application may determine an OD prediction in accordance with a value of a for the current ODE. The OD predication may include a discrete variable having one of J levels, where J is an integer and in the present embodiments may be set to 3 (although J may be set to other values) such that there may be J1, J2, and J3 levels of OD predictions which may correspond with a low likelihood of OD, high likelihood of OD and an undetermined likelihood of OD, respectively. Each of these J=3 levels of OD may be set to have a corresponding threshold value or range of values (as shown in the present embodiments) associated therewith such that J1=0.00-0.33, J2=0.44-0.66, and J3=0.67-1.00, as may be set forth in the SSI. The OD detection/management application may then compare the (OD) confidence value s compared to the values of each of J1, J2 and J3 and determine whether the (OD) confidence value & corresponds with the range of J1, J2 or J3. Accordingly, if it is determined that the (OD) confidence value s corresponds with the range of J1, it may be determined that there is a high likelihood of OD and may set an OD flag=1 (ODF=1). If it is determined that the (OD) confidence value e corresponds with the range of J2, it may be determined that there is a low likelihood of OD and may set an OD flag=2 (ODF=2). If it is determined that the (OD) confidence value a corresponds with the range of J3, it may be determined that there is an unknown likelihood of OD and may set an OD flag=3 (ODF=3). Thus, each OD flag may represent one or more discrete levels as may be determined by the system. The results of the analysis which may include an OD prediction may include, for example, the ODF(s) and/or information associated therewith, may then be provided to the OD confirmation application for further analysis.

In some embodiments the discrete confidence ranges may be determined based upon a comparison of the confidence value ε with one or more threshold values. For example, assuming two discrete confidence ranges such as a high confidence range and a low confidence range separated by a confidence threshold value such as 0.50. The system may then determine whether the confidence value ε is less than or equal to the confidence threshold value. If it is determined that the confidence value ε is less than or equal to the confidence threshold value, the system may determine that there is a high confidence that the OU having an OD and may set the ODF=1 to indicate that there is a high likelihood of an OD. If it is determined that the confidence value ε is not less than or equal to the confidence threshold value (e.g., is greater than), the system may determine that there is a low confidence that the OU having an OD and may set the ODF=2 to indicate that there is a low likelihood of an OD. In some embodiments, the OD prediction may include the confidence value ε.

The OD detection confirmation application 216 may receive the OD predication from the OD detection/management application 208, may render a challenge to interact with the OU in response thereto, and may determine whether the OU is experiencing an OD based upon a timely response to the challenge from the OU within a first threshold time period. If it is determined that a response to the challenge is not received within the first threshold time period, it may be determined that the OU is suffering from an OD and in indication of such may be generated, e.g., an OD confirmation (ODC) signal, and may be provided to the shock controller 212, injector control 214, and/or alarm management application 210 for further analysis. If it is determined that a response to the challenge is received within the first threshold time period (i.e. is timely), the first threshold time period may be reset to its initial value, the challenge may be rendered once again, and the system may wait for a response to the challenge within the first threshold time period once again. This process may be repeated until a second time threshold is determined to have elapsed at which time the current QUE may be ended and information associated with the QUE may be stored in a memory of the system for later use and/or analysis.

With regard to the challenge and the first and second time thresholds, in some embodiments, these may be selected, adjusted, and/or set/reset in accordance with the OD prediction. For example, the challenge may be selected from a plurality of challenges and/or one or more of the time thresholds (e.g., the first and second time thresholds) may be set in accordance with the OD predication. For example, if there is a high likelihood of an OD (as indicated by an OD prediction) the first threshold time period may be shorter than if there was a low likelihood of an OD. This may provide for a more immediate response to a possible OD of the OU when time is of the essence. Similarly, the second time threshold may be set to longer value as the likelihood of an OD increases. This may provide more time for monitoring the OU during an OUE when the likelihood of an OD is higher.

Lastly, with regard to challenges, these may be assigned a likelihood of OD. For example, there may be challenges that may be assigned to a low likelihood of an OD and others that may be assigned to a high likelihood of an OD. In some embodiments, the challenges and/or the time thresholds may be selected in accordance with the challenge while in other embodiments, the challenges and/or time thresholds may be preset and stored in a memory of the system such as the SSI for later selection and/or use.

The shock control application may be configured to shock the OU using any suitable form of stimulation such as chemical, mechanical or electrical (e.g., electric shock) upon receiving the ODC signal from the OD detection confirmation application. Accordingly, the shock control application may receive at least one signal from the OD detection confirmation application and determine whether this input signal includes an ODC signal. If it is determined that the input signal does not include an ODC signal, the shock control application may continue to monitor the input signals. If it is determined the input signal includes the ODC signal, the shock control application may control a high voltage electronic generator (e.g., a high voltage coil, etc.) to generate a high-voltage signal which may be applied to the skin of the OU via a pair of electrodes coupled to the high voltage electronic generator and in contact with the skin of the OU. The high voltage signal may have a duration corresponding with a shock threshold time as may be set by the SSI and when applied to the skin of the OU may shock the OU to awaken and/or gain the attention of the OU.

The high voltage signal (or other form of shock) may have any desired duration (e.g., 2 seconds, etc.), waveform shape (sine, step, ramp, etc.), amplitude, and/or frequency and may be repeated at periodic and/or nonperiodic intervals (e.g., a response threshold time such as every 20 seconds, etc.) as may be set in the SSI until a response is received via UI of the MS of the OU and/or the wearable as may be set forth in the SSI. If a response is not received within a response threshold time (e.g., 20 seconds, etc.) the shock may be repeated, etc. In some embodiments, the shock may be applied at the start of an ODE.

With regard to the pair of electrodes configured to receive the high voltage signal and may include an adhesive coating configured to adhere to the skin of the OU and may include a conductive layer such as a gel to transfer the electrical signal to the skin of the OU. The pair of electrodes may be independent of other electrodes or may be shared with other electrodes of the system such as the at least one electrode in which case an isolator may be provided to isolate sensitive circuitry from the high voltage signals. The isolators may be passive or active and controlled by a controller of the system to active slightly before and after the high voltage signals are generated and applied to the corresponding electrodes. In some embodiments sufficient distance may be maintained between electrodes to prevent crosstalk and/or undesirable noise transmission between electrodes and/or other circuitry.

The injection control application 214 may be configured to an injector to provide at least one dose of a opioid antidote to the OU when an OD is confirmed. Accordingly, the injection control application may receive at least one signal from the OD detection/management application and may analyze this signal to determine whether the ODC signal (which is a signal indictive of an OD confirmation) is present. If it is determined the ODC signal is not present, the injection control application may continue to monitor signals received from the OD detection/management application. If it is determined that the ODC signal is present, the injection control application may be configured to initiate an injection process to administer at least one dose of at least one opioid antidote, such as an opioid antagonist (e.g., Narcan, Naloxone, and/or the like), to the OU. This injection routine may vary based upon a type of injector(s) employed by the system which may include passive and active type injectors.

With regard to the passive type injector(s), an injection process may control at least one actuator configured to trigger the start of a corresponding injection process and may be powered by one or more of hydraulic, pneumatic, mechanical (e.g., springs), and/or electronic actuators. In some embodiments, an actuator may be controlled to control a depth of penetration of a hypodermic needle such that it may penetrate to a desired depth which may prevent the needle from striking a bone of the OU in that area of penetration.

The active type injector(s) may include the injection routine may control one or more actuators to control position, direction, and/or speed (the latter being velocity) of the hypodermic needle and/or flow rate of a pump configured to pump the opioid antidote from a reservoir to the OU via the hypodermic needle to administer medication in accordance with SSI. One or more sensors may obtain SI which may be provided to a controller of the system for further analysis such as to determine one or more of direction and speed the hypodermic needle and/or flow rate of the pump and/or total volume of fluid displaced (e.g., of the opioid antidote ml). The controller may then control the actuators in accordance with embodiments of the present system.

After the desired dose of the desire medication is administered (e.g., the total volume is equal to the desired dose volume) and/or upon receiving an abort signal during the injection process, the pump may be stopped and the hypodermic needle may be reversed to withdraw it from the skin of the OU and/or place it in a parked position. The speed of the hypodermic needle and/or dose pump as well as dose may vary in accordance with system settings as may be set forth in the SSI. The injection process may be aborted at any time by the OU and/or a CG.

Injection status may be monitored by the injection control application and may be rendered on a rendering device of the system such as a display of the wearable and/or MS of the OU, and/or MS of the CG. Injection status may include information related to an injection such as "Injection in process" "Injection completed at (3:00 pm), 4 mg Narcan administered," "Injection Stopped," etc.

When initiated, the injection routine may control one or more actuators based upon a type of injector employed by the system such as an passive injector in which an injection process may be triggered and thereafter may run automatically, or an active injector in which hypodermic needle and/or medication pump displacement (speed and/or position) may be controlled in accordance feedback information (e.g., obtained from SI) and/or system settings as may be set forth in the SI and/or SSI. The one or more actuators may include one or more of linear or rotary actuators, linear or rotary motors, pneumatic actuators, spring actuators, etc., depending upon embodiments.

An abort option may be rendered on a rendering device such as the wearable and/or MS of the OU and, when selected (as may be determined by the system) the injection process may be stopped (e.g., pumps stopped, hypodermic needle withdrawn and parked) and an indication of such may be rendered on the rendering device for the convenience of the OU. Accordingly, the injector control application may determine whether the abort selection item has been selected by the OU, and if it is determined that the abort selection item has been selected, the injector control application may be configured to stop the injection from occurring or to abort an injection in process (e.g., by stopping a pump and/or withdrawing the hypodermic needle from the OU. Feedback SI may be provided to a controller of the system and information relating thereto may be rendered for the convenience of a user such as "Hypodermic Needle Withdrawn, Safe to Remove, 0.5 mg dose of administered" on a rendering device of the system such as on the display of the wearable or MS of the OU and/or CGs such as the monitor, EMS. Indication of OU status such as "OU alert," "OU unconscious," etc. may also be rendered.

The alarm control application may be configured to render one or more alarms such as an OU and CG alarms upon receiving the ODC signal from the OD detection confirmation application. Accordingly, the alarm control application may receive at least one signal from the OD detection confirmation application and may determine whether this input signal includes the ODC signal. If it is determined the input signal includes the ODC signal, the alarm control application may generate, transmit, and/or render one or more alarms such as the OU and CG alarms to inform the OU and the CGs of the ODE, respectively, depending upon system settings as may be set forth in the SSI.

The types of alarms rendered, devices which may render these alarms (e.g., wearable, MS, etc.) and/or CGs whom the alarms are transmitted to (e.g., monitor, EMS, MP, etc.), etc., may correspond with settings for the current OUE and/or SSI depending upon system settings. For example, in some embodiments, the SSI may override OU settings or vice versa as may be desired. If it is determined that the input signal does not include the ODC signal, the alarm control application may continue to monitor the input signals from the OD detection confirmation application.

With regard to the alarms to inform the OU, the alarm control application may generate and render one or more alarms which may be rendered on one or more rendering devices of the MS of the OU and/or the wearable such as on a display, a speaker, a haptic device (e.g., a vibrator, etc.), an electrical stimulator, etc., to gain the OUs attention and/or to awake the OU from sleep, to render instructions for the OU to follow if possible, and/or to respond to a request for input such as "press here to respond." Inputs from the OU may then be relayed to a controller of the system for further analysis such as to determine whether the OU is experiencing an OD, awake, etc. In some embodiments, prior to generating an electrical shock, the alarm control application may provide an electrical stimulation via the pair of electrodes employed by the shock control application.

With regard to the alarms to inform the CGs, one or more of the CGs for the current QUE may be alerted via their MSs and/or contact information. Alerts may be updated in real time and be the same or customized for each CG or may be the same as may be defined in the SSI. In the present embodiments it will be assumed that each CG may receive the same information related to the OU and/or current OUE such as one or more of OU ID, OD status ("currently experiencing an OD"), location, start time of the current QUE (OD detected 12:04 pm, 3 minutes ago, etc.), monitor CG contact information, SI including vitals, physiological information, current status (e.g., Naloxone administered, breathing restored, etc.), etc., as may be set forth in the SSI for the convenience of one or more of the CGs such as the monitor, MP, and/or EMS depending upon system settings as may be set forth in the SSI. Once an OD is detected, the current QUE may remain open until closed by one of the CGs with authority as may be set forth in the SSI.

For the sake of clarity, it will be assumed that communication with the CGs may be established. It should be understood, however, that in some embodiments the OU may be out of communication with the CGs in which case the stimulus unit and/or other settings may be set in accordance with no communication (hereinafter no-com) settings. For example, no-com settings may set forth higher shock levels, increased doses of the opioid antidote, etc., and may be set forth in the SSI.

Figure 7:
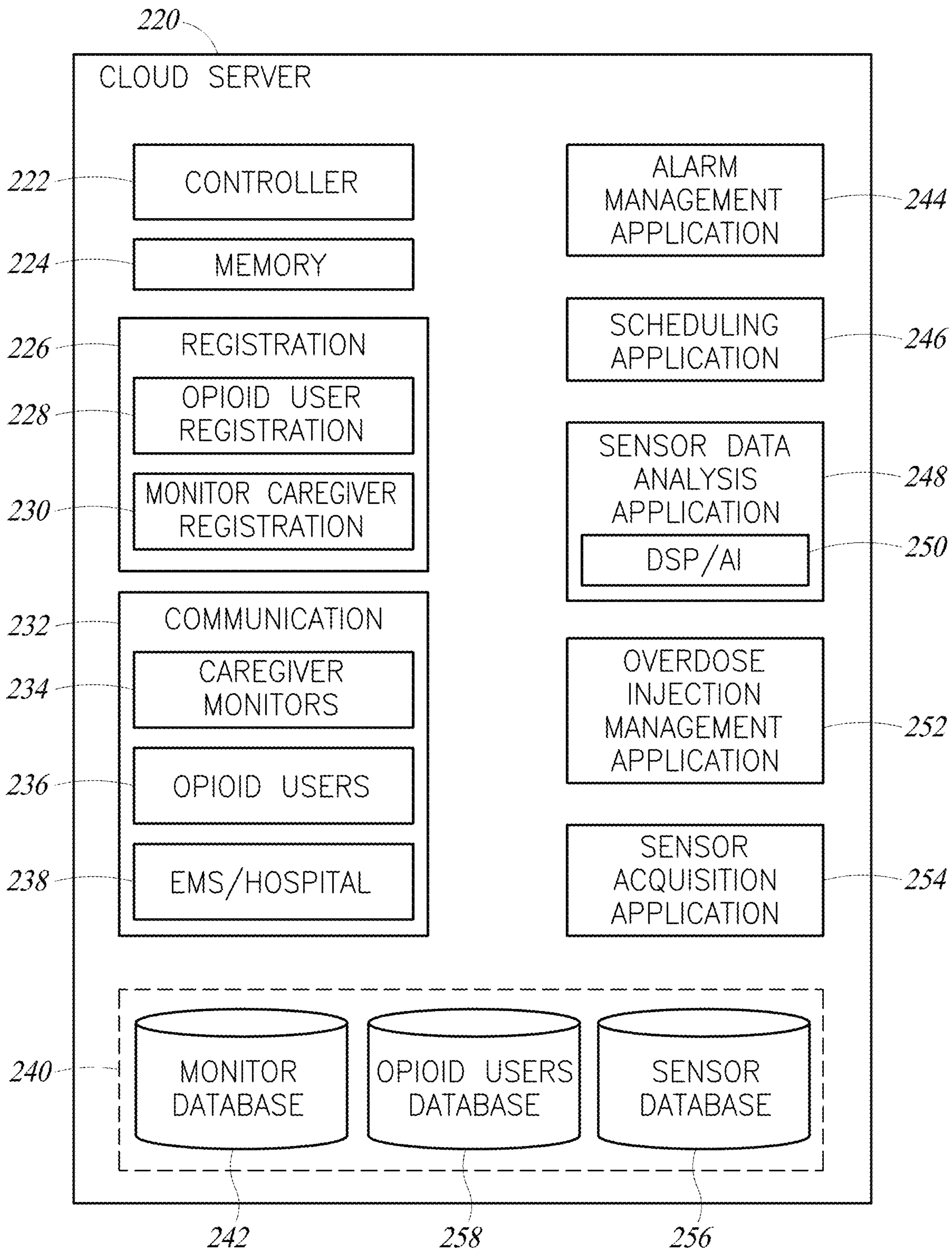
FIG. 7 is a block diagram illustrating the cloud server in more detail including example applications executing thereon and databases maintained therein.

A block diagram illustrating the cloud server (CS) in more detail including example applications executing thereon and databases maintained therein in accordance with embodiments of the present system is shown in FIG. 7. The CS, generally referenced 220, may be similar to the CS 14 (FIG. 1) and may include one or more of a controller 222, memory 224, communications application 232, registration application 226, sensor acquisition application 254, alarm management application 244, scheduling application 246, sensor data analysis application 248, OD injection management application 252, monitor database 242, opioid user database 258, and sensor database 256, one or more of which may communicate with each other via optical, wired, and/or wireless communication methods.

The monitor database, opioid user database, and sensor database may generally be referred to as databases (DBs) and may be part of an operational DB 240 of the CS 220. For the sake of clarity, the following description may be made to with reference to a single OU and the OUs respective MS and wearable unless the context indicates otherwise. It should be understood, however, that embodiments of the present system may be operative with a plurality of OUs and respective MSs and wearables.

The controller may control the overall operation of the CS and may be similar to the controller 16 of FIG. 1 and may load and/or run one or more applications such as one or more of the communications application, sensor acquisition application, alarm management application, scheduling application, sensor data analysis application, registration application, and OD injection management application. The controller may obtain operating instructions from a memory of the system, such as the memory 224 which may be similar to the memory 18 (FIG. 1), and may include any suitable memory which may be local to the CS and/or may distributed throughout the system. The controller may be configured to provide a UI with which one or more users of the system such as the OU, the CGs, etc. may interact with the system.

The communications application 232 may control communications of the CS and may be configured to enable communication between, or with, one or more users of the system such as the OUs and/or their respective CGs via their respective MSs and/or via their respective contact information. The communication application may include one or more of a CG monitor communications 234 which may control communication to the monitors, an OU communication 236 which may control communication to the OUs, and an EMS/hospital communication which may control communication to the EMS/hospital 238. The communications application may control communication between the OU and the respective CGs during an OUE and/or ODE. Communication may be established via any suitable network or networks of the system such as a telephony network, a cellular network, the Internet, etc.

It is also envisioned that the communications application may enable communication between one or more portions of the CS such as one or more of the databases under the control of the controller to, for example, store information in and/or to retrieve information from the corresponding database.

The alarm management application may manage alarms of the system such as an OD alarm and may transmit alarms such as alerts and notifications to one or more portions of the system such as one or more of the MSs of the OU and the CGs (e.g., monitor, medical provider/hospital, and/or EMS) under the control of the controller. For example, the alarm management application may provide notifications to the MSs such as the MS of the OU and the MSs of the CGs in accordance with embodiments of the present system and when an ODE is detected or when otherwise requested, the alarm management application may transmit an alarm to one or more of the CGs to alert the corresponding CGs of the ODE and provide information related to the OU such as OU-ID, location, etc., in accordance with the SSI.

The sensor acquisition application may acquire sensor information from one or more sensors of the system, such as sensors of a corresponding MS (e.g., of the OU, etc.) and/or the wearable of a corresponding OU, and may provide the acquired sensor information to the controller and/or the sensor data analysis application 248 for further analysis processing and/or storage in a memory of the system such as the memory 224. In some embodiments, the acquired sensor information may be processed (e.g., preprocessed) by the controller or may be provided directly to the data analysis application for further analysis and processing.

For example, it is envisioned that the controller may process $SpO_2$ sensor information to form PPG sensor information which may then be provided to the data analysis application for further processing. The sensor acquisition application 254 may obtain information related to each OU of the system and/or groups and/or subgroups of OUs and may obtain sensor information related to each (or selected groups or subgroups) OU from their respective MSs and/or wearable(s).

The sensor data analysis application may include a DSP/AI application 250 and may obtain sensor information from one or more sensors of the system such as PPG information, and may process the sensor information using the DSP/AI application to obtain one or more predications in accordance with embodiments of the present system. These predications may then be further processed with sensor information to determine whether the OU is having an OD during an OUE and/or a likelihood of whether the OU is having an OD during an QUE. Results of the determination may then be provided to the controller and/or one or more MS of the system such as MSs of the OU, the CGs, etc. in accordance with embodiments of the present system.

For example, analysis results for an QUE may be returned to the MSs of the OU and/or CGs associated with that OUE. The sensor data analysis application may further generate and/or update one or more AI models, machine learning models, and/or algorithms and store them in a memory of the system such as the memory for later use. The sensor data analysis application may preprocess sensor information to be processed by the DSP/AI application and may acquire AI models and/or algorithms to be applied to DSP/AI analysis by the DSP/AI application when processing sensor information generated by the system. The preprocessing may include, for example, processing pulse-oximetry sensor information such as $SpO_2$ to form corresponding PPGs that may be processed by the DSP/AI application. The sensor data analysis application may obtain algorithms and/or models from one or more memories of the system and may obtain sensor information in real time and/or from one or more memories of the system.

The OD injection management application 252 may manage and injection process of the OU when it is determined that the OU is experiencing an OD. The injection management may further control a shock process that may provide a shock to be applied to the OU such as electric shock, a haptic signal, chemical stimulus, etc., in accordance with system settings as may be set forth in the SSI of the OU, when it is determined that the OU is having an OD. The OD injection management application may calculate a signal waveform to be applied to the OU and may control the wearable of the OU to generate and apply this signal waveform to the OU in an attempt to awaken the OU. The OD injection management application, may interact with a user such as the OU to inform the OU of a pending injection and/or shock, and may provide a selection item for by a user of the system such as the OU and/or CG (e.g., the monitor, etc.) to abort the injection. The OD injection management application may provide a status of an injection administered to the OU to one or more users of the system such as CGs of the OU via their respective MSs and may manage an information exchange between one or more of the OU and the CGs when it is determined that the OU is experiencing an OD.

The monitor database may include information related to one or more of the monitor CGs such as identification (ID), contact address, schedule information (e.g., schedule of availability), current availability (e.g., currently online, offline, currently monitoring OUE, etc.), history (e.g., OUE success), relationship to the OU (e.g., parent, sibling, spouse, etc.), authentication codes (e.g., access codes), authentication settings (access level(s), access database(s), etc.), user reviews (e.g., user ratings such as five stars, etc.), and corresponding setting information SSI. The SSI may be set/reset by the corresponding monitor and/or system and may reflect personalized settings for the corresponding monitor.

The registration application 226 may provide registration services for CGs and/or the OU which registration may thereafter be used to authenticate a user such as the OU and/or CG. Registration may be performed on a one-time basis with no identifiable information related to one or more of the OU and/or CG or may be stored for later use and/or authentication. Authentication may be performed using an ID unique to a user which ID may include email addresses, telephone numbers, social networking addresses, unique IDs, passwords, etc. Once authenticated, the system may be configured to provide access to the system in accordance with access rights for each user.

It is envisioned that the registration application may provide a user interface (UI) with such as a GUI or the like, with which a user may interact with the system and/to perform a registration for the same of another user such as one or more of the OU and CGs. The registration application may include one or more of an OU registration application 228 and a monitor CG registration application 230 each being configured to a corresponding type of user such as the OU and CGs, respectively. In some embodiments, the registration application may be configured to provide an interface for a third party user (e.g., an agency, a hospital, etc.) to register one or more of the OU and/or CGs or may provide an interface for self-registration (e.g., OU, CGs self-register, etc.).

The OU registration application may provide one or more applications configured to register an OU to the system. The registration may be performed at each use or may be performed once and thereafter may be automatic each time the MS of the OU uses an application of the system or certain actions are sensed (e.g., wearable is worn, injector cartridge coupled or removed, etc. as may be set in the SSI). In some embodiments, the OU may use an MS which is not registered to the OU and may perform a registration using authentication information specific to the corresponding OU such as one or more of an account name, ID, email account, biometric-ID information, social networking account, and/or password, etc. pre-registered to the system for the OU. These settings may be stored in a memory of the system and/or in the SSI of the corresponding OU. Once registered, the OU may use one or more functions of the system in accordance with system settings. In some embodiments a guest setting may be provided for use by a guest.

The monitor CG registration application may provide one or more applications which may be configured to register a monitor CG to the system. The registration may be performed at each use or may be performed once and thereafter may be automatic each time the MS of the monitor CG uses an application of the system. In some embodiments, the monitor CG may use an MS which is not registered to the monitor CG and may perform a registration using authentication information specific to the corresponding monitor CG such as one or more of an account name, ID, email account, social networking account, and/or password, etc., which may be pre-registered to the system for the monitor CG. In some embodiments, a schedule of the monitor CG may run determine a schedule of the corresponding CG and the system may transmit information to the MS (or a contact address) of the corresponding CG to remind the monitor of upcoming appointments (e.g., with the OU) that maybe scheduled. These settings may be stored in a memory of the system and/or in the SSI of the corresponding monitor CG. Once registered, the monitor CG may use one or more functions of the system in accordance with system settings.

The opioid user database may include information related to one or more of the opioid users OUs such as identification (ID), contact address, working address, corresponding CGs such as monitor(s), doctor(s), hospital(s), health provider(s), etc., current operational status (e.g., currently online, offline, serving OU, etc.), history (e.g., drug use, ODs, etc.), authentication codes (e.g., access codes), and setting information such as SSI. The SSI may be set/reset by the corresponding OU and/or system to reflect personalized settings for the corresponding OU. Each user may have a different type of SSI associated therewith such that an OU may have a type of SSI that may be different from the SSI of a CG such as a monitor, an MP, and/or an EMS, etc.

The sensor database may include information related to one or more sensors of the system such as settings, accuracy, type (e.g., reflective pulse-oximeter sensor, etc.), identification (ID), calibration settings, parameters, connection preferences (e.g., Bluetooth, etc.), pairing information, etc. The sensor database may further include sensor information generated by one or more sensors of the system during one or more OUEs and/or tests.

Figure 8A:
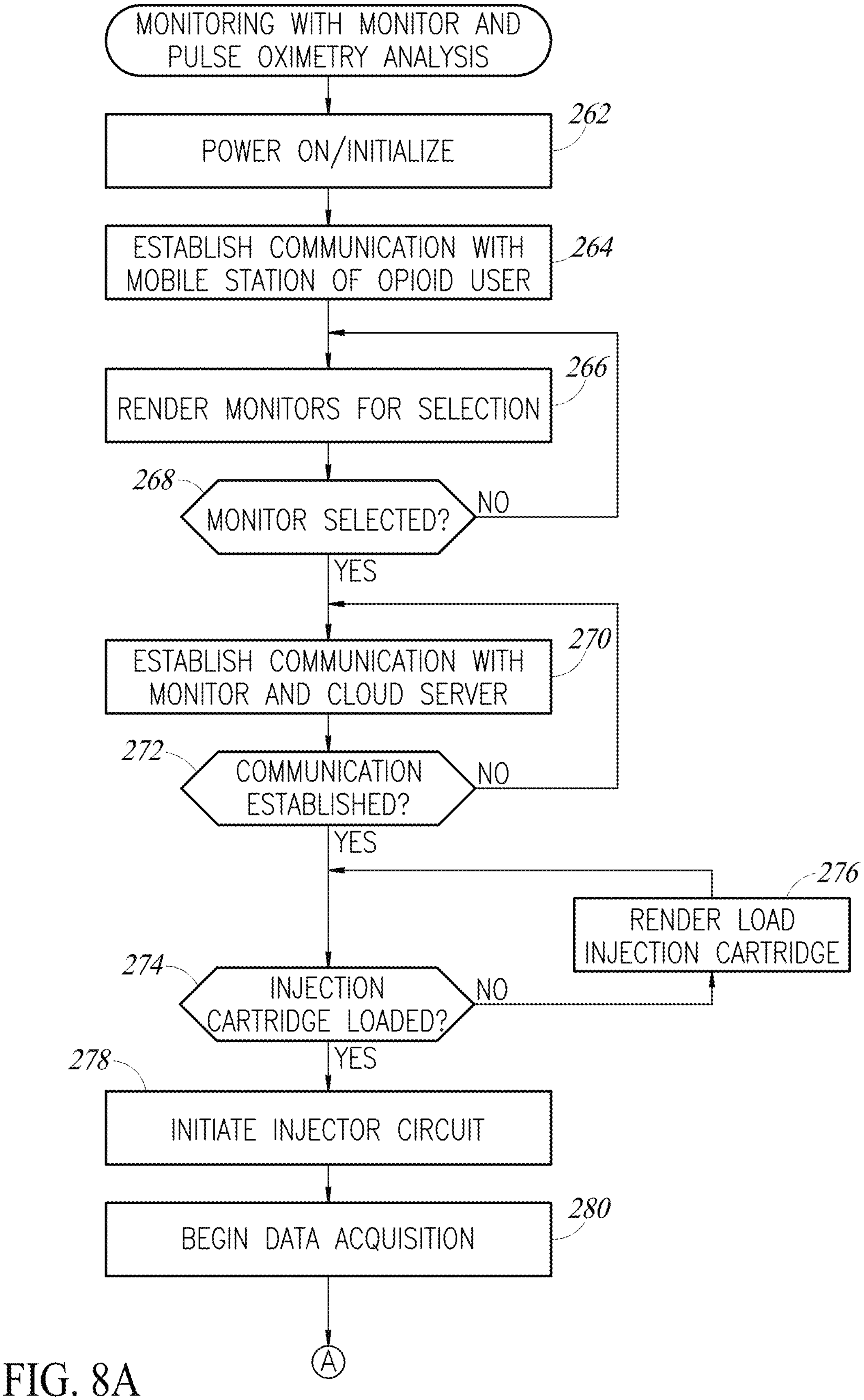
FIGS. 8A, 8B, 8C are a flow diagram illustrating an example method of monitoring an opioid user using a monitor caregiver and pulse oximetry analysis.
Figure 8B:
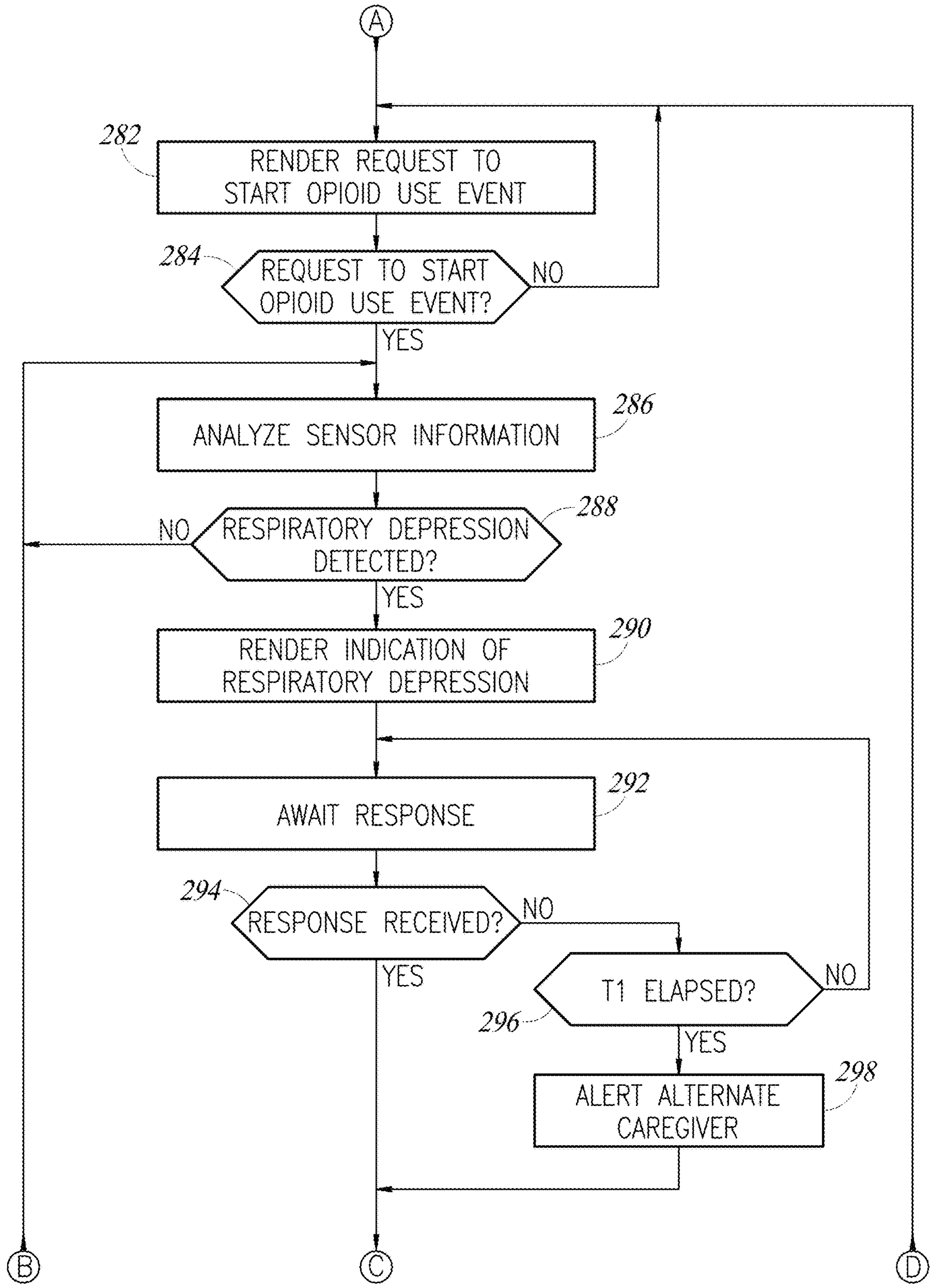
Figure 8C:
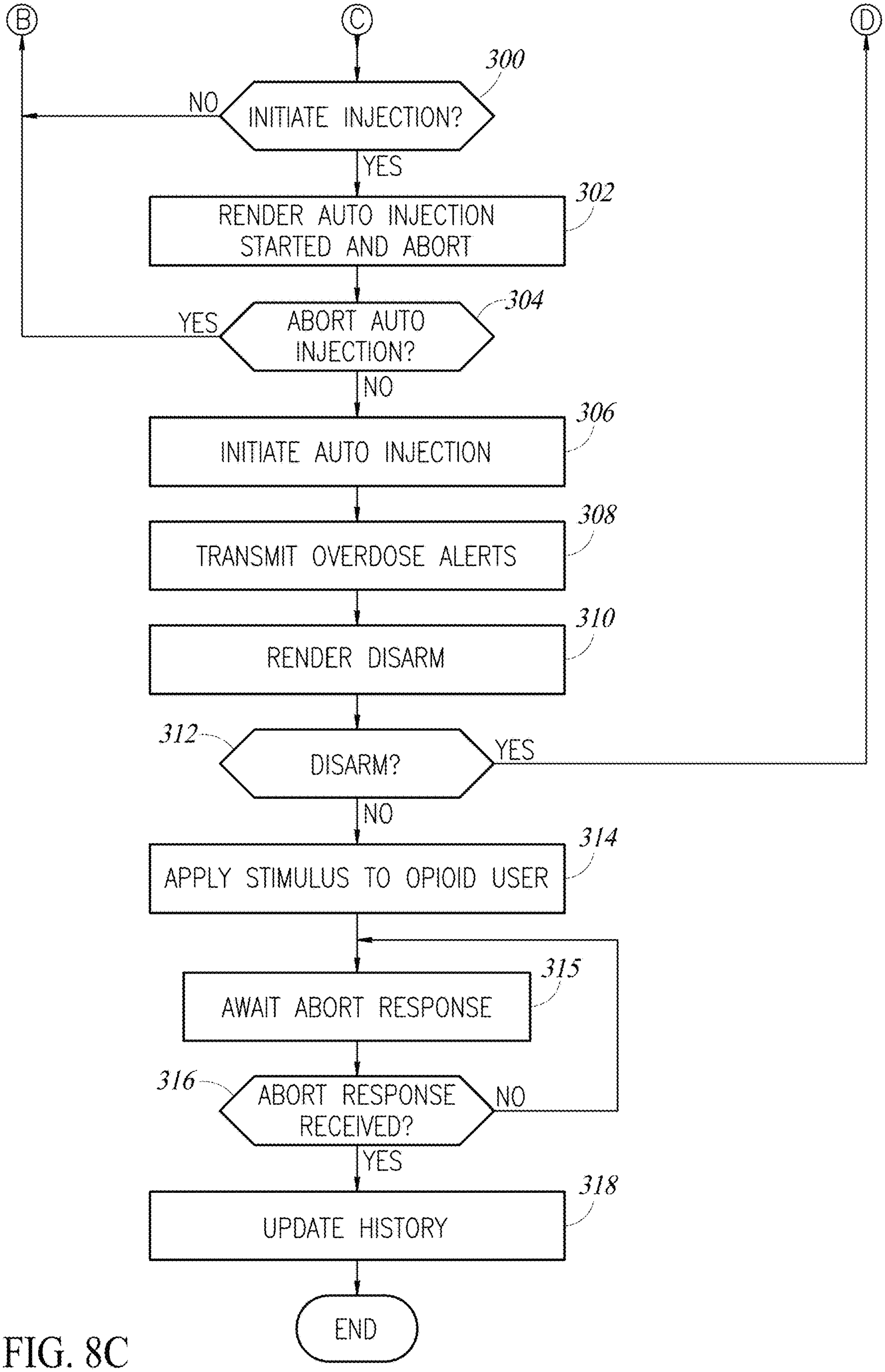
Figure 9A:
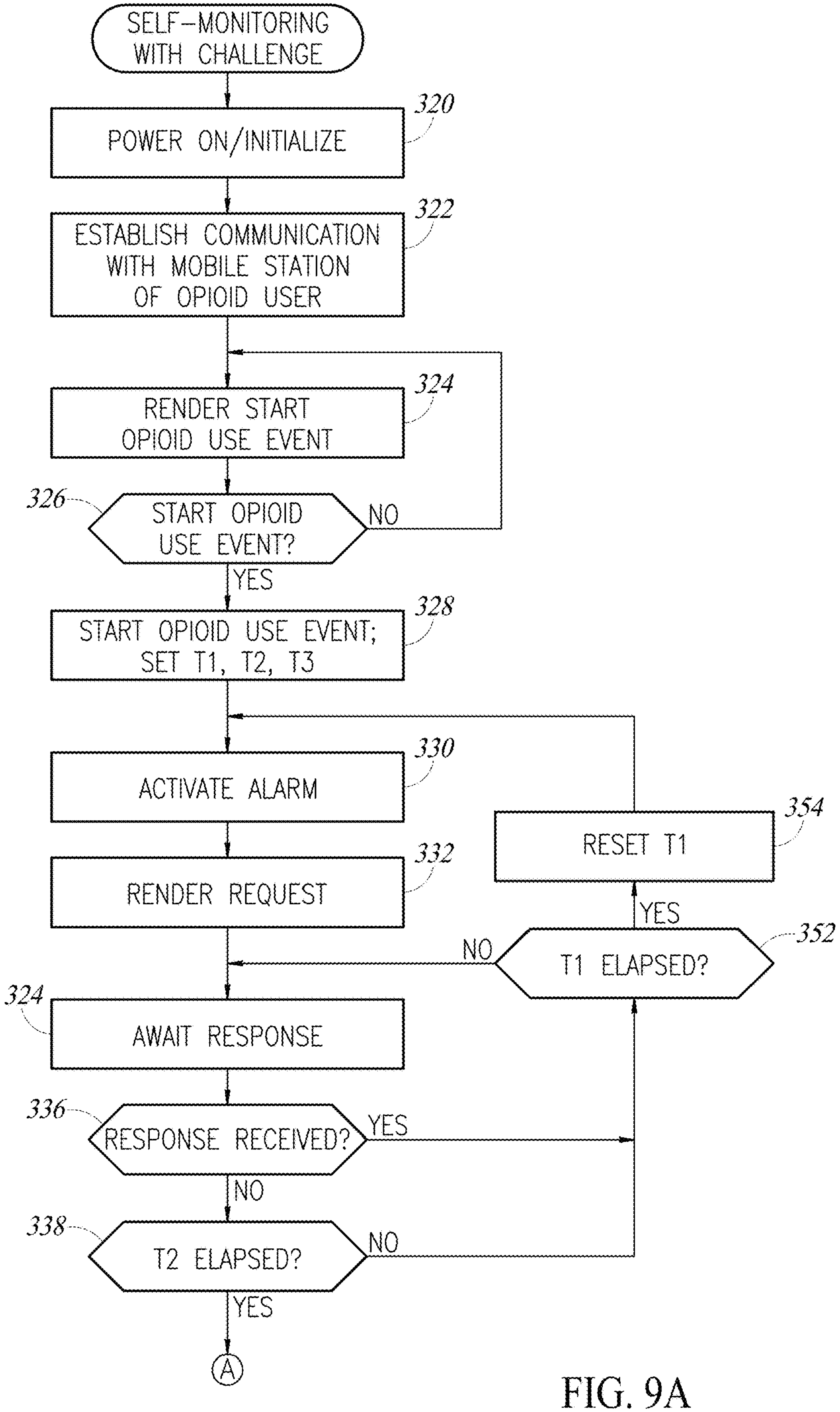
FIGS. 9A and 9B are a flow diagram illustrating an example method of self-monitoring an opioid user that utilizes a challenge to detect an ODE.
Figure 9B:
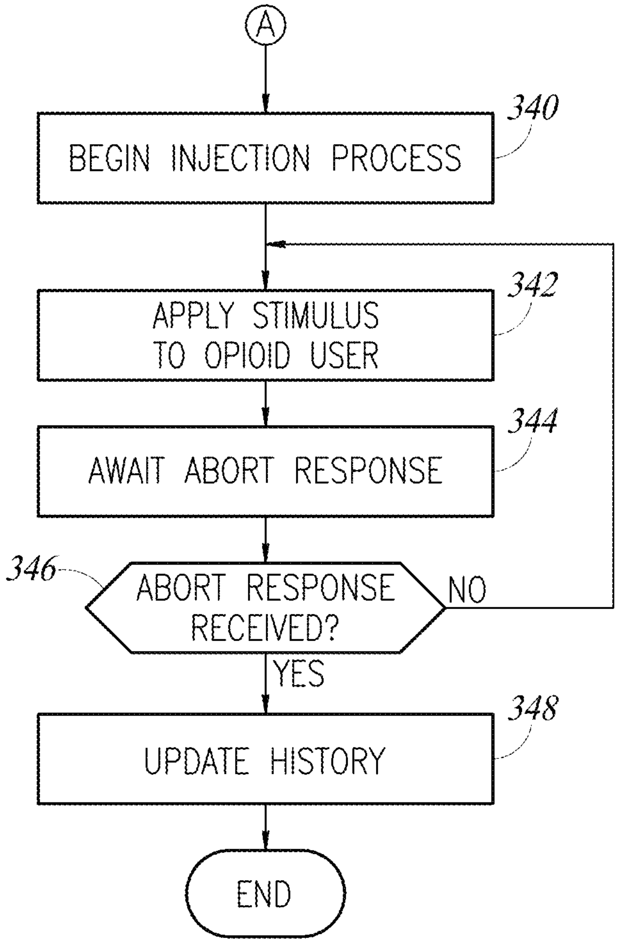
Figure 10A:
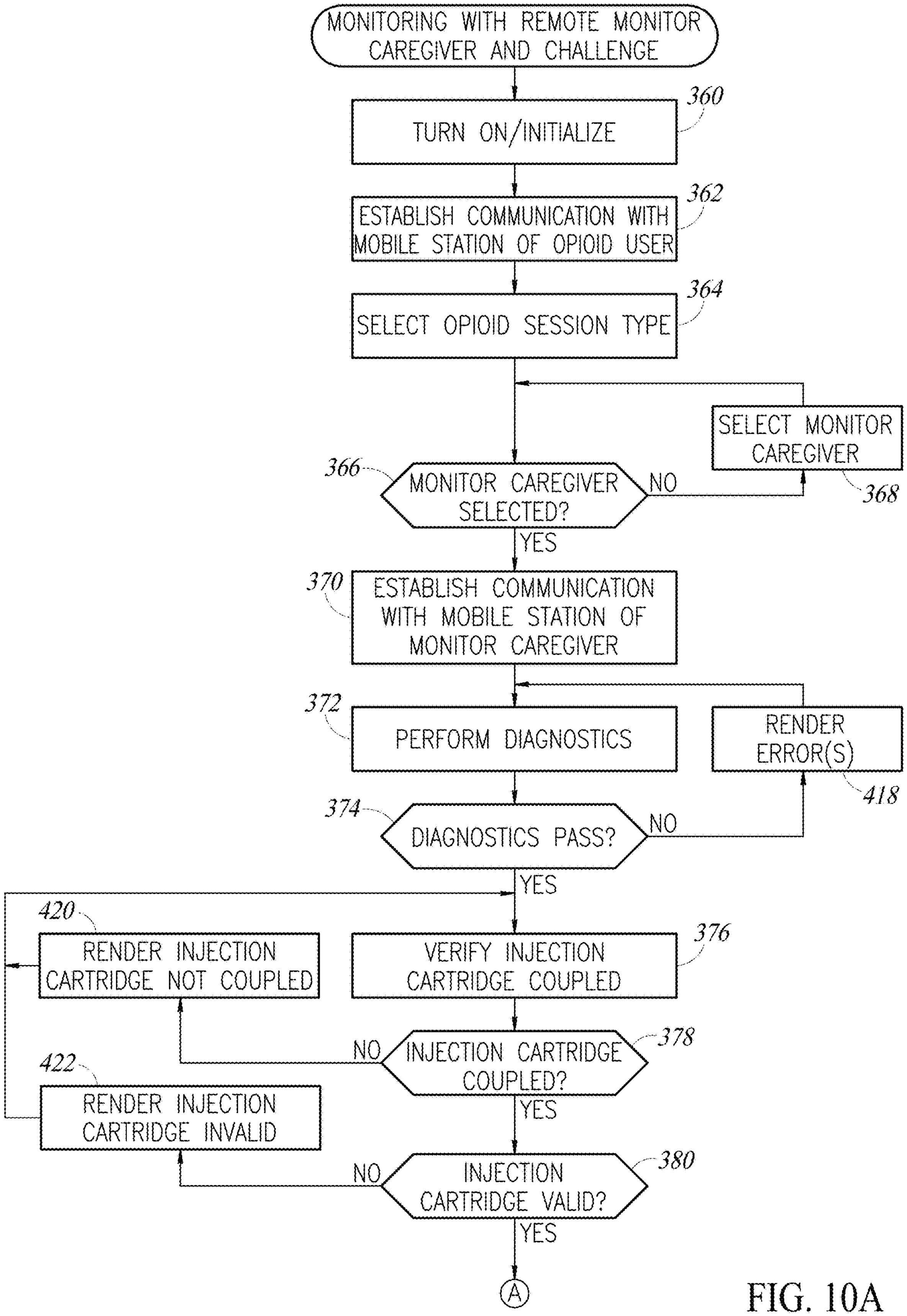
FIGS. 10A, 10B, 10C are a flow diagram illustrating an example method of remote-monitoring an opioid user utilizing a challenge to detect an ODE.
Figure 10B:
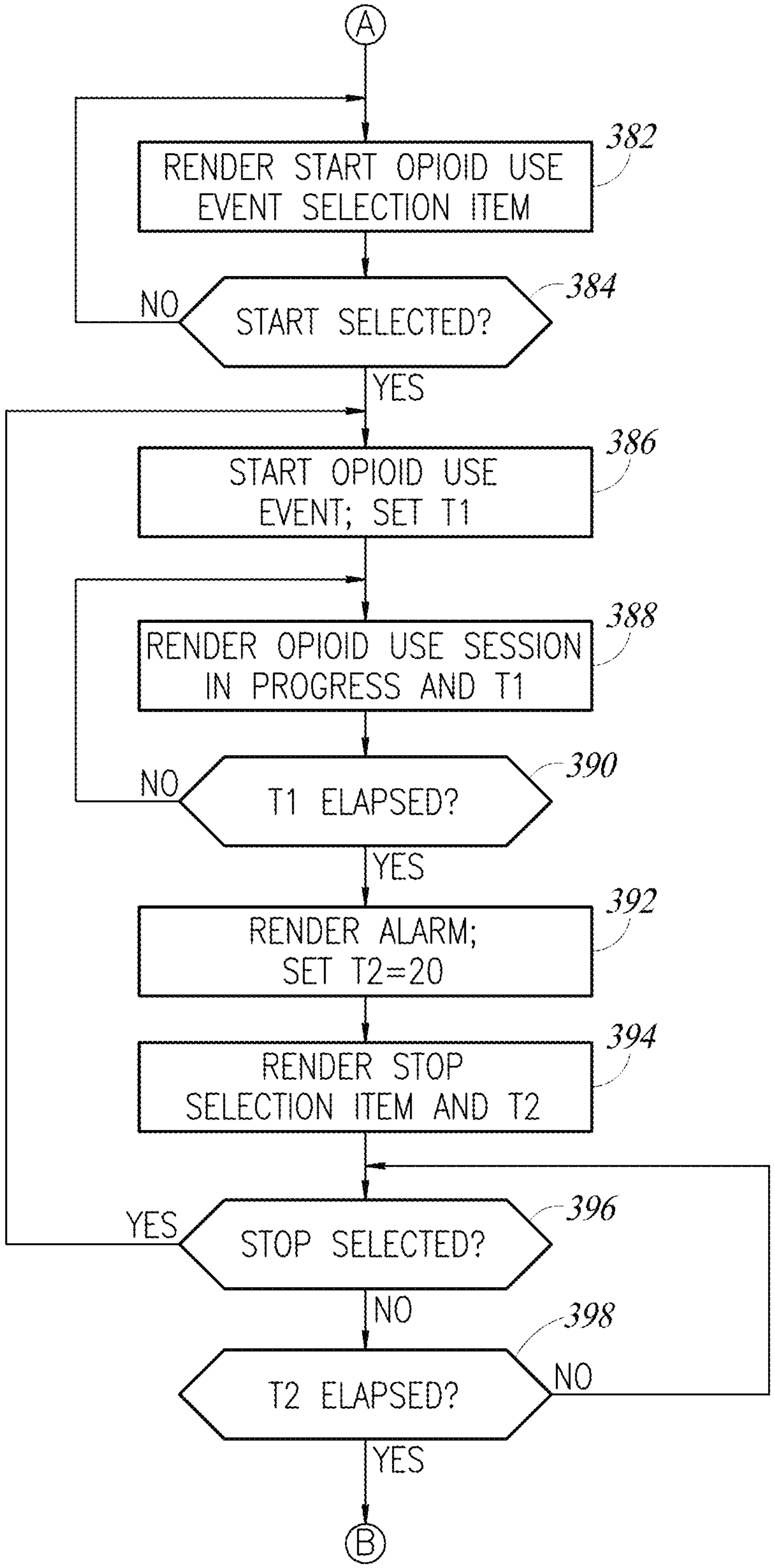
Figure 10C:
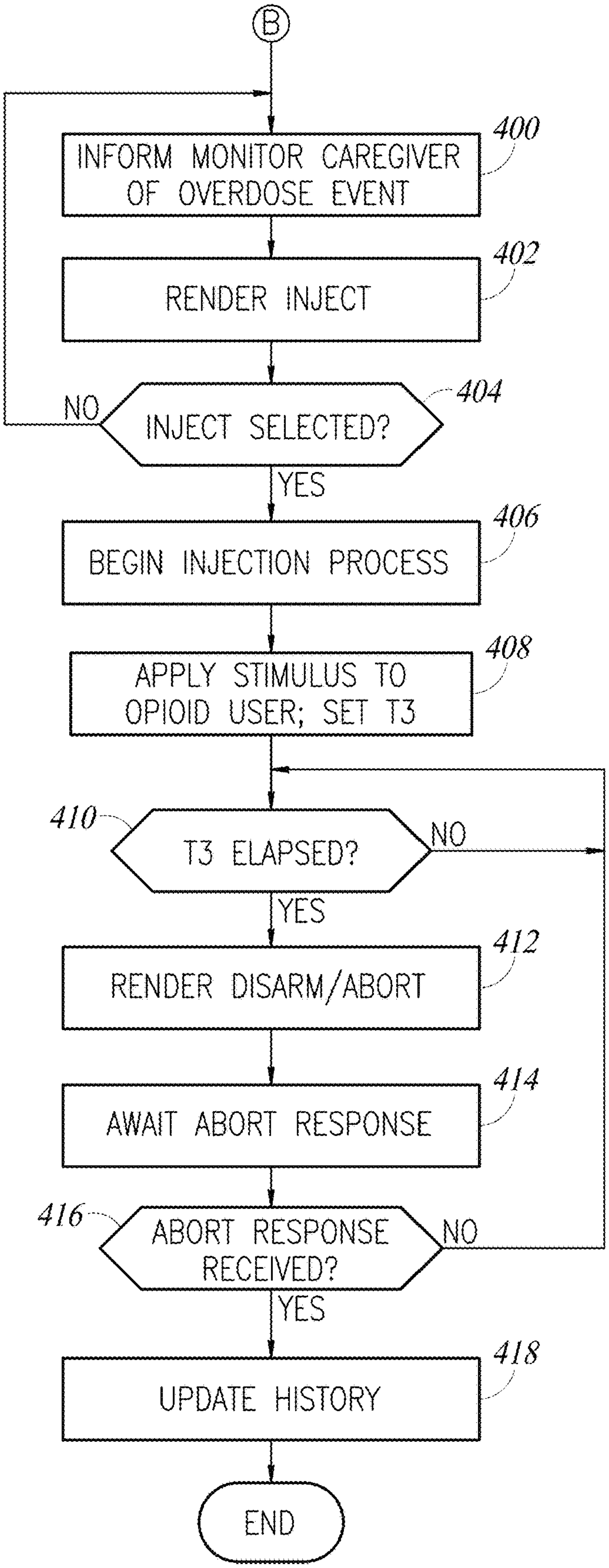
Figure 11A:
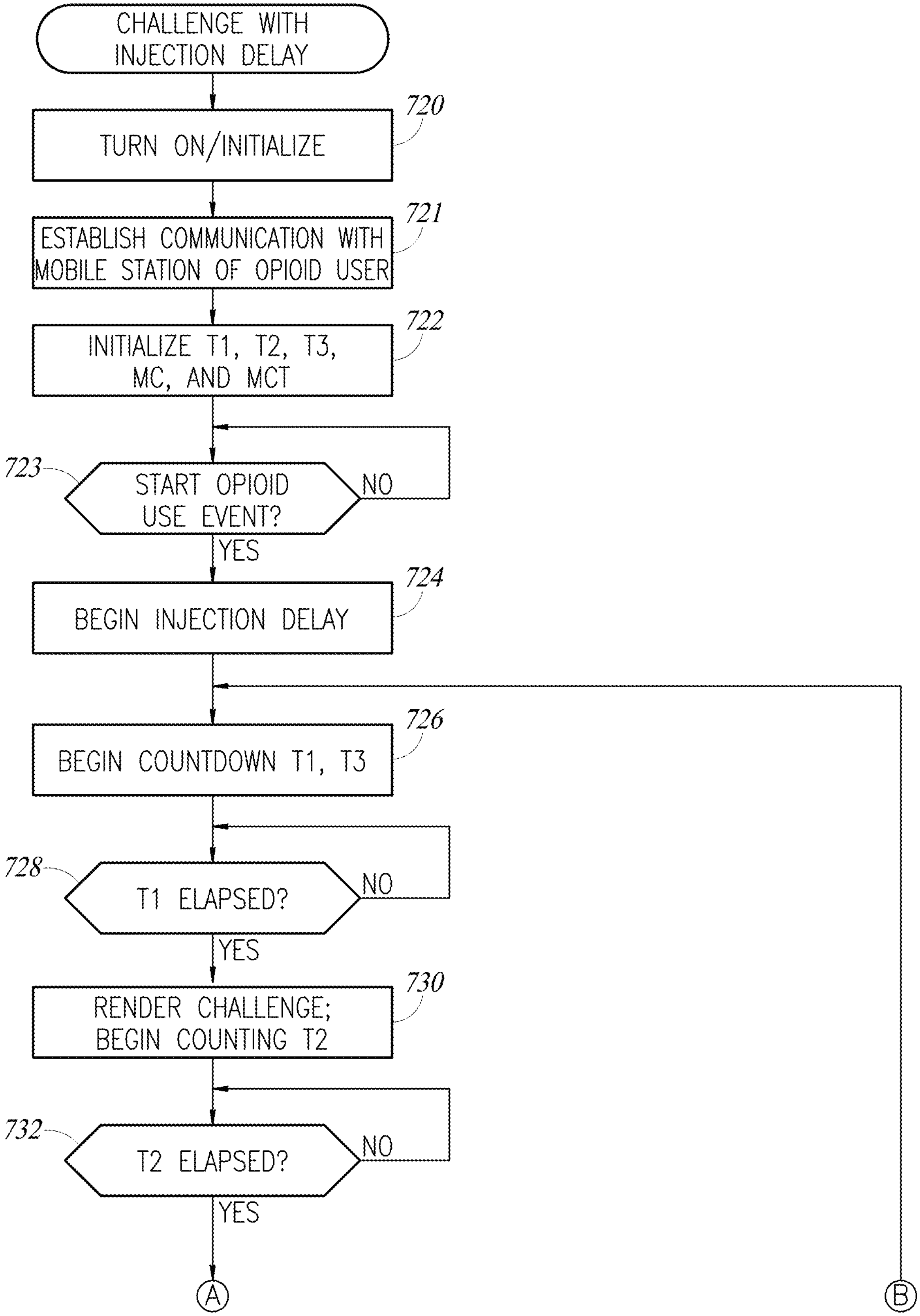
FIGS. 11A and 11B are a flow diagram illustrating an example method of self-monitoring an opioid user with pre-authorized injection and corresponding delay.
Figure 11B:
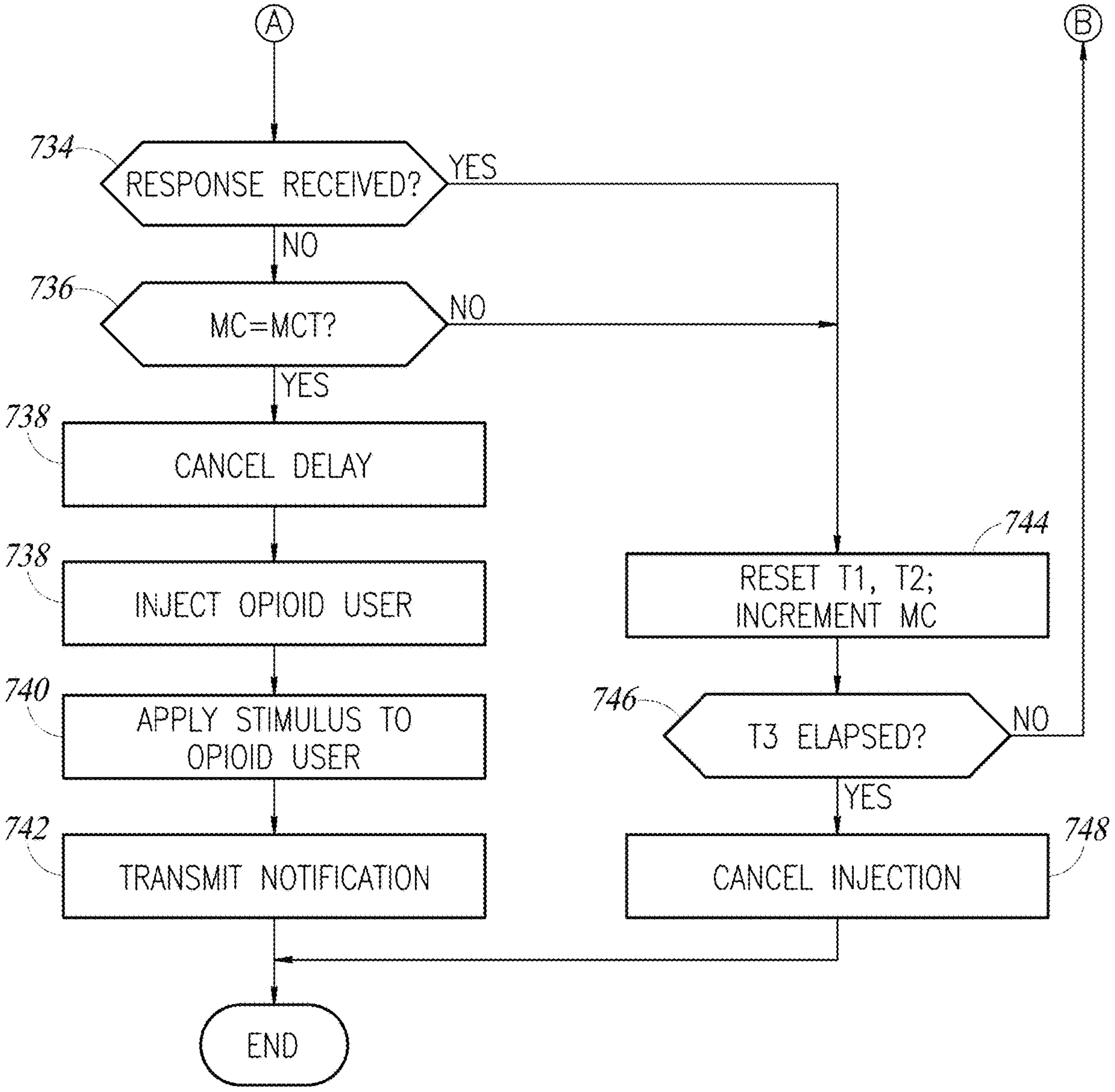
Figure 12:
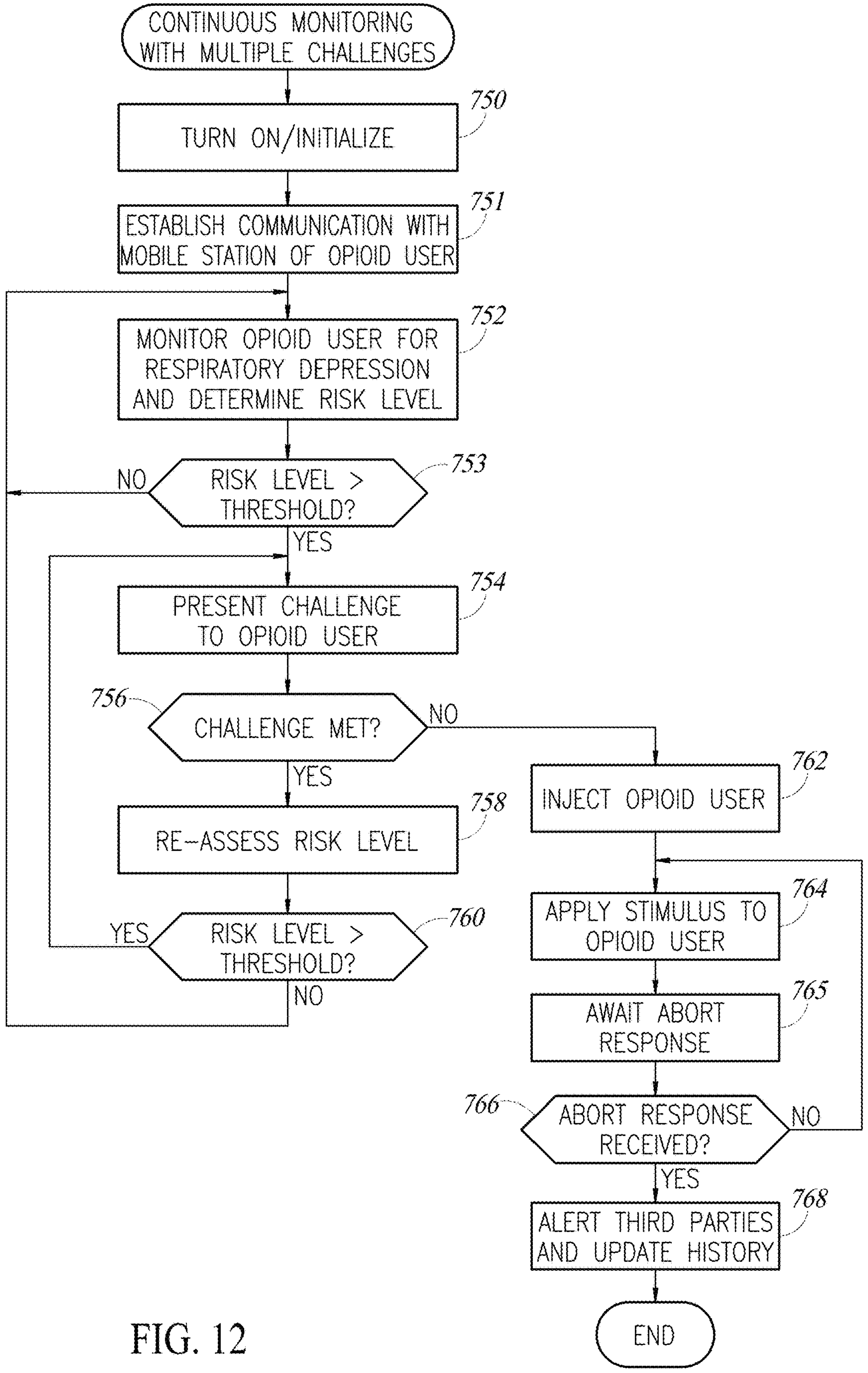
FIG. 12 is a flow diagram illustrating an example method of continuous monitoring with multiple challenges.

Operational processes performed by the system will now be described in more detail with reference to FIGS. 8A, 8B, 8C, 9A, 9B, 10A, 10B, 10C, 11A, 11B, and 12. FIGS. 8A, 8B, 8C are a flow diagram illustrating an example method of monitoring an opioid user using a monitor caregiver and pulse oximetry analysis. FIGS. 9A and 9B are a flow diagram illustrating an example method of self-monitoring an opioid user that utilizes a challenge to detect an ODE. FIGS. 10A, 10B, 10C are a flow diagram illustrating an example method of remote-monitoring an opioid user utilizing a challenge to detect an ODE. FIGS. 11A and 11B are a flow diagram illustrating an example method of self-monitoring an opioid user with pre-authorized injection and corresponding delay. FIG. 12 is a flow diagram illustrating an example method of continuous monitoring with multiple challenges.

It is noted that the methods described herein may be performed using one or more processors, computers, controllers, etc., communicating over a network and may obtain information from, and/or store information to, one or more memories which may be local and/or remote from each other. The methods may include one of more of the following steps and may be performed using a controller operating in accordance with embodiments of the present system. One or more of the steps of the methods may be combined together, skipped, and/or separated into sub-acts, or performed serially or in parallel with each other or other steps in accordance with embodiments of the present system. For the sake of clarity, the process may be described with reference to a single MS of an OU. Without limitation, however, it is noted that the process may employ a plurality of MSs corresponding to each of a plurality of OUs each of which may include a separate workflow such as a sub-workflow if desired.

Monitoring With Monitor CG and Pulse Oximetry Analysis

With reference to FIGS. 8A, 8B, 8C, the method begins by turning on, awakening, and initializing the wearable from an off or low power mode in response to an 'on' signal and may then initialize by performing an initialization routine (step 262). The on signal may be generated by any suitable switch, button, key, and/or sensor of the system, may be analog or digital, and may be included in corresponding SI. Depending upon system settings and/or configuration, the on signal may be generated in response to passive and/or active interaction with the wearable such as an IC being coupled to the wearable, wearable being in contact with the skin of the OU, a band of the wearable being tightened about the OU, and/or a band fastener of the wearable being fastened for use. For example, it is envisioned that the system may include one or more switches (e.g., an on switch), buttons (e.g., an on button), and keys (hard or soft) that may be configured to generate the on signal in response to selection by the OU (e.g., depressing, placing in an on position, etc.). For the sake of clarity, it will be assumed that embodiments of the present system may employ this method.

With regard to the wearable being in contact with the skin of the OU, in some embodiments, suitable sensors may include proximity sensors such as optical sensors (e.g., pulse ox, etc.), capacitive (e.g., electrode type sensors), ultrasonic, and/or mechanical switches (e.g., microswitches, etc.) that may determine when the wearable in contact with the skin of the OU and may generate the on signal in response thereto. In some embodiments, proximity sensors include any suitable type of proximity sensor such as capacitive, inductive, lidar, photoelectric, and/or any other suitable type of proximity sensor(s).

With regard a band of the wearable being tightened about the OU, suitable sensors may include any suitable sensor that may detect tension of the band and/or engagement with the OU, suitable sensors may include (e.g., a capacitive sensor, an elastoresistivity sensor, a piezo-electric sensor, a strain gauge, a spring loaded force-type sensor, a tactile sensor, etc.) that may detect a force caused by tension applied to the band. The sensor may further determine when this force is greater than or equal to a threshold force (as may be define din the SSI), and generate an on signal when it is determined that the force is greater than or equal to the threshold force.

With regard to the band fastener of the wearable being fastened for use, suitable sensors may include a tactile sensor, an elastoresistivity sensor, capacitive sensor, and/or switch (e.g., a microswitch, etc.) may be configured to sense when the band fastener is fastened for use.

In some embodiments, the system may turn on when a plurality of on signals are generated by corresponding sensors such as the hall-effect sensor and the tension sensor depending upon system settings.

With regard to the low power mode, in this mode some sensors may be minimally active to sense when to generate the on signal. For example, one or more of switches, buttons, keys (hard or soft), and/or sensors of the system and associated circuitry may be provided power by the power management of the wearable sufficient for operation and generation of the on signal when conditions permit.

Once the wearable is turned on, it may begin an initialization process which may load SSI and may set system settings and parameters in accordance with the SSI. The SSI may further include information related to the OU such as OU settings, opioid antidote type (e.g., Narcan), opioid antidote dose, syringe type (passive, active, etc.), needle penetration depth, etc., information related to the IC such as (used, not used, medication used, etc.), etc. may be obtained at this point if an IC if coupled to the wearable. The IC may include information indicative of one or more ID, medication, status (e.g., used, new). In the present embodiments, a monitor CG may be employed during an QUE and this OUE may be referred to as a monitor CG type QUE as opposed to a self-monitor type OUE described with reference to the method of FIGS. 9A, 9B, described infra.

The method then establishes communication between the wearable and the MS that is registered thereto using any suitable communication method(s) such as Bluetooth or the like and may attempt to establish communication between the MS and a CS of the system via any suitable network such as the Internet, a cellular network, etc., in accordance with system settings (step 264). The process may obtain information related to at least one monitor CG such as one or more of ID (or the monitor), contact information, and/or availability. This ID may identify the at least one caregiver (e.g., "John Doe", etc.), the contact information (e.g., social networking address, telephone number, etc.) may be employed to establish communication with the at least one caregiver during an QUE, and the availability information may indicate availability (e.g., currently available, available in 30 minutes, etc.) of the at least one caregiver. If communication between one or more of the wearable, MS, and/or CS cannot be initially established, the system may reattempt to establish communication and may render a message indicating such for the convenience of the OU.

The information related the at least one monitor CG is then rendered for selection by the OU to be a selected CG for a current OUE (step 266). The process may render in a list format (or other format as may be desired and set in the SSI) information related to each corresponding monitor CG of the at least one monitor CG such as ID (e.g., name, screen name, etc.), availability, etc., on any suitable rendering device of the system such as on a display of the MS of the OU or the wearable for the convenience and/or selection by the OU. The OU may then select a desired monitor CG from the list of one or more listed monitor CGs and/or may enter the contact address of a desired monitor CG if desired (e.g., “call Jane monitor”). Accordingly, the process may await a selection or other input from the OU and may respond accordingly. In some embodiments, the information related to the at least one monitor CG may be rendered audibly on a speaker of the system as may be set forth in the SSI. In some embodiments, the list may include a monitor CG only if determined to be currently available for an OUE. In some embodiments, this step may be skipped when it is determined that a default monitor CG is set forth in the SSI or automatic selection of a monitor CG is selected as may be set forth in the SSI. In some embodiments, the process may render information to inform the OU to select a monitor CG such as “Please Select A Monitor CG For A Current OUE,” etc.

It is then determined whether a monitor CG has been selected (step 268). If the monitor CG has been selected, the process continues to step 270. Otherwise, if the monitor CG has not been selected, the process repeats step 266.

Communications is then established with one or more other portions of the system such as an MS of the selected monitor CG and the CS if not already established during step 264 (step 270). The MS of the OU may attempt to communicate with the CS of the system and may attempt to establish communication with the selected monitor CG via any suitable network or networks such as a network of the system, e.g., network 26 (FIG. 1). The system may attempt to contact the selected monitor CG at an address set forth by the information related to at least one monitor CG, set forth by the SSI (e.g., a default monitor CG, etc.), and/or input by the OU. In some embodiments, it is envisioned that the system may attempt to contact the selected monitor CG using a default address first and thereafter may attempt other addresses listed for the monitor CG. The process may employ any suitable communication method such as optical, wired, and/or wireless communication methods to establish the communication(s) via any suitable network of the system. Similarly, the process may attempt to establish communication with an OU application of the CS using any suitable communication method(s) via the network of the system. In some embodiments, the MS of the monitor CS may have already established communication with the CS prior to the current step in which case at least a portion of this step may be skipped.

If communications with the selected monitor CG has been established (step 272), it is then determined whether the injection cartridge (IC) is loaded (step 274). If communication with the selected monitor CG has not been established (step 272), the method returns to step 270. By establishing communication between the OU and the selected monitor CG, the OU may be monitored during the OUE. For the sake of clarity, in the present embodiments it will be assumed that communication has been previously established with the CS an OU application operating on the MS of the OU during step 264.

If the IC is not coupled to the wearable (step 274), then the user is prompted to load it (step 276). In some embodiments, if is determined that the cartridge is coupled to the wearable, the process may determine whether the IC is used or expired. If it is determined that the IC is used or expired, the method will prompt the user to load a fresh one.

The system may render on a UI of the MS or the wearable information determined during step 274 such as “Injection Cartridge Not Installed, Please Install Injection Cartridge Before Continuing,” “Injection Cartridge Has Been Previously Used, Please Insert A New Injection Cartridge,” “Injection Cartridge Is Expired, Please Install A New Injection Cartridge,” or the like as may be set forth in the SSI. After completing step 276, the method may repeat step 274. In the present embodiments, it will be assumed that a new and unexpired IC is being used and is coupled to the wearable. In some embodiments, the system may reject ICs having in incorrect ID, are reused or refilled, contain a different medication from that specified for the OU, etc. as may be set forth in the SSI.

Next, the method initializes an injection circuit for dispensing the opioid antidote (e.g., Narcan) (step 278). The initialization may include cycling one or more actuators or electrical circuits coupled to a dispensing cartridge (hereinafter cartridge for the sake of clarity) or syringe to deactivate any safety mechanism(s), to test circuits, and/or to position portions of the actuators and/or cartridge to an location suitable for injection. The safety mechanisms which may prevent accidental dispensing and extension of a hypodermic needle contained within the cartridge during use and/or handling. As the injection circuit may vary based upon cartridge design and/or type (e.g., passive type and/or active type), the injection circuit may be configured to correspond with the cartridge design and/or type. In some embodiments, the safety mechanism may be rearmed after an QUE an injection routine was not preformed and/or if the cartridge is removed from the wearable. The safety mechanism may be of a passive or active type. If any errors are detected, information indicative of such and/or instructions to resolve the error may be rendered on a rendering device of the system for the convenience of the OU. For example, the system may render information such as “injection circuit of dispensing cartridge could not be initialized-please reinsert dispensing cartridge,” on a rendering device of the system such as on the wearable and/or MS of the OU for the convenience of the OU.

Data acquisition is then begun to obtain SI from one or more sensors of the system, such as a pulse oximetry sensor which may be coupled to the wearable or MS, for review, analysis, and/or storage in a memory of the system for later use (step 280). The system may determine whether SI is being acquired and if it is determined that SI is being acquired, the system may render information of such as “system ready.” If data acquisition is not successfully completed, however, the system may render information of such as “data collection error” or “injection cartridge not seated,” etc., on a rendering device of the system such as on a display of the wearable and/or MS of the OU for the convenience of the OU and may provide instructions to resolve the corresponding issue. Data acquisition may be performed in real time using one or more sensors of the system such as the pulse oximetry sensor(s), etc. In some embodiments, the system may require SI from all sensors registered to an QUE, from available sensors, and/or from at least one sensor as may be set forth in the SSI.

The method then renders a request to start the opioid use event (OUE) (start OUE) for selection by the OU (step 282). In some embodiments, this request may be rendered using any suitable rendering device of the system such as a speaker, a display, a hard or soft key, a haptic device, etc., depending upon system settings as may be set forth in the SSI. For example, in the present embodiments the system may render the request by illuminating on one or more buttons or hard or soft keys for selection by the user. In yet other embodiments, the system may render one or more selection items instructing the OU such "press to start opioid use event," "start opioid use session," "start use," "start monitoring," etc., on a UI of the system such as on a display of the wearable and/or MS of the OU and await a response thereto from the OU. In some embodiments, voice commands may be rendered using the speaker depending upon system settings as may be set forth in the SSI and the system may respond to voice inputs from the OU. In some embodiments, the process may await a gesture and/or haptic input that may be registered to start an OUE depending upon system settings as may be set forth in the SSI. In some embodiments, this step may include rendering a request for pre-authorization for the opioid antidote injection from either the opioid user or one or more of CGs depending upon system settings.

The method then determines whether the request to start the QUE has been selected (step 284). If the request to start the OUE has been selected, the process analyzes sensor information (step 286). Otherwise, the method returns to step 282. During step 286, the process analyzes the acquired SI to detect respiratory depression. Accordingly, the process may perform analysis on the acquired sensor information using on or more AI methods operating in accordance with embodiments of the present system to detect signs of respiratory depression.

For example, pulse oximetry sensor information may be converted into PPGs which may then be analyzed by at least one AI engine using one or more AI methods. The output of the AI engine may then be further processed alone or in accordance with other sensor information and/or inputs by the OU, a CG such as the monitor CG, to determine whether the OU is experiencing respiratory depression (e.g. an overdose OD). At this step, it may be assumed that the request for pre-authorization for the opioid antidote injection from either the opioid user or one or more of CGs was granted.

The method then determines whether respiratory depression has been detected (step 288). If respiratory depression is not detected, the process repeats step 286. If respiratory depression is detected, an indication is rendered that respiratory depression has been detected (in the OU) and a first selection item to initiate an injection of the opioid antidote (hereinafter initiate the injection) and a second selection item not to initiate the injection on the UI of the MS of the monitor CG (step 290).

For the sake of clarity, the first and second items may be combined into an injection selection item (ISI) that may include the first and second selection items and may be manipulated a first way (e.g., pressed) select to initiate the injection or may be manipulated a second way (e.g., swiped up, to the side, etc.) to select not to initiate the injection. Accordingly, the system may render on the UI of the MS of the monitor (or other CGs as discussed infra with reference to step 296) the indication that respiratory depression has been detected such as "respiratory depression detected" and may render the ISI which may include a selection item that may be selected to initiate the injection such as "Initiate Injection," and/or "Inject Naloxone," and a second selection item that may be selected not to initiate the injection. The monitor CG may select the ISI and interact with it to select it to initiate the injection or not to initiate the injection. It is also envisioned that the process may further render information relating to the OU such as ID, sensor information (e.g., physiological information such as pulse rate, respiratory rate, $SpO_2$, etc. on the UI of the MS of the monitor CG for review by the monitor CG. In some embodiments, a selection item to not initiate the injection of the opioid antidote may be provided to select not to initiate the injection.

In some embodiments, information rendered on the MS of the monitor CG may also be rendered on MSs of other CGs depending upon system settings as may be set forth in the SSI. For the sake of clarity, it will be assumed that in the present embodiments the monitor CG may initiate the injection. In alternative embodiments, the OU and/or other CGs may initiate the injection in a similar manner as the monitor CG depending upon system settings as may be set forth in the SSI.

In some embodiments, at least one contact selection item (including identification such as "contact MP or contact EMS) may be rendered, and when selected by the monitor CG, the process may contact the selected CG and may initiate a conference call with the selected other CG. This may provide the monitor CG with additional support if necessary and may be beneficial during a training phase.

Depending upon system settings, in some embodiments, it is envisioned that the process may set a response timer (TR) to a time as may be set forth in the SSI (e.g., two minutes in the present embodiments although other times are also envisioned as may be set in the SSI) and may begin to countdown this time.

The method then waits for a response to the ISI from the monitor CG (step 292). If a response to the ISI is received from the monitor CG (step 294), it is then determined whether to initiate an injection (step 300). If no response is received (step 294), it is determined whether the response timer (T1) has elapsed (step 296). If not, the method returns to step 292. If the timer has elapsed, an alert is rendered on a UI of an MS of at least one other CG such as the MP and/or EMS (depending upon system settings as may be set forth in the SSI) that a response to the ISI is overdue (step 298). The method can further render an indication that respiratory depression has been detected in the OU and the ISI the UI of the MS of the at least one at least one other CG. This step may be similar to step 290. The system then waits for a selection from at least one other CG to the ISI. This may provide for monitoring of CGs such as the monitor CG which may be especially useful during a training phase.

If an injection is not to be initiated (step 300), the method returns to step 286. Otherwise, if an injection of the opioid antidote is to be initiated (e.g., initiate auto-injection) an indication that the injection is about to start as well is rendered (step 302). An option to abort the injection is also rendered in this step. For example, the process may be configured to render on one or more UIs of the wearable and/or MS of the OU information indicating status of the process such as auto-injection has started or is about to start and may provide a selection item to abort the auto-injection of the opioid antidote. For example, the process may render on a UI of the wearable and/or the MS of the OU information such as "Auto-Injection Started" and may provide a selection item that may be selected to abort the auto-injection such as "Abort" for the selection of the OU.

In some embodiments, one or more hard keys such as those on the wearable may be illuminated using a flashing light (e.g., red, etc.) and/or the like to indicate the injection (e.g., the auto-injection) has started or is about to start and may be selected (e.g., by depressing, etc.) to abort the injection. In some embodiments, a dedicated abort key may be provided and may selected to abort the injection. The abort selection item may be considered a challenge presented to the OU who may respond to this challenge by selecting the abort selection item or button, key, or entering a haptic action, a voice command, or other input mapped to the abort selection item. Thus, by selecting the abort selection item, it may be considered that the OU has responded to the challenge. In some embodiments, a threshold time may be provided (e.g., 10 seconds, etc. as may be set forth in the SSI) to respond and select to abort the injection.

In some embodiments the indication that injection is about to start may be rendered on the wearable and/or MS of the OU using audio, electrical via the stimulus unit (e.g., high voltage stimulation), and/or a haptic signal (e.g., an audio message, a signal pulse train (e.g., three repeated pulses, etc.) that may be stored in a memory of the system and as may be set forth in the SSI. It is also envisioned that the OU may select to abort the injection using any suitable input such as voice, keypress or touch (e.g., on the touch-screen), and/or a haptic input (e.g., chopping motion, etc.) that may be mapped to the abort selection item in accordance with the SSI (e.g., a three pulse signal train). This may awaken the OU if sleeping and may alert the OU of impending injection.

It is then checked whether the OU has selected to abort the injection (e.g., auto-injection of the opioid antidote) (step 304). If the OU has selected to abort the injection, the method goes to step 286. It is noted that other users such as CGs may select to abort the injection by selecting the abort injection selection item.

If the OU has not aborted the injection of the medication (step 304), an injection (auto-injection) routine is initiated to inject the opioid antidote into the OU (step 306). As the cartridges may be of an active or passive type, methods employed to perform the injection may in be accordance with cartridge type and/or configuration and may be defined in system settings as set forth in the SSI.

In some embodiments, the process may activate one or more actuators (e.g., solenoids, motors, etc.) to either drive or cause a driving force to act upon a hypodermic needle to drive the hypodermic needle into the OU and to drive a plunger in communication with a medication to inject the medication into the OU via the hypodermic needle that was driven into the OU. These actuator(s) may be commonly referred to as injection actuator(s) (IAs).

In some embodiments, the hypodermic needle may be driven directly by the actuator while in others the actuator may release another actuator such as an compressed gas cylinder or preloaded spring to drive the hypodermic needle into the OU and/or to drive the plunger to drive a plunger in communication with a medication to inject the medication into the OU via the hypodermic needle that was driven into the OU. In some embodiments, the process may retract the extended hypodermic needle while in others a sheath may extend to cover the hypodermic needle.

One or more OD alerts are then transmitted to one or more CGs such as an EMS CG, the monitor CG, and the MP CG (in accordance with system settings as may be set forth in the SSI) informing them of the detected OD via their respective registered contact information such their respective contact addresses and/or MSs in accordance with system settings (step 308). The OD alerts transmitted to the EMS CG may include a request for aid (RFA). The registered contact information for EMS CG, this information may be selected based upon a current location (e.g., address, geophysical location, State, etc.) of the OU. Accordingly, the system may determine the location of the OU, select EMSs based upon the determined location, and initiate contact with this selected EMS. The SSI may include information which may associate EMSs CGs and contact information in accordance with location and the process may access this information to select and/or contact the EMS CG corresponding to the determined location of the OU. The OD alert may include information such as one or more of OU ID, location, vitals (if available), type and/or amount of opioid injected if available, and type and/or amount (e.g., dosage) of opioid receptor antagonist (e.g., Naloxone such as Narcan, Naloxone, and/or the like) injected into the OU to counter the effects of the opioid.

The monitor CG may be informed in real time about the status of the OU. In some embodiments, a communication channel or channels (e.g., video calling channels, voice call channels, etc.) may be configured to provide for communication between the monitor CG and one or more of the EMS CG and the EMS CG in real time. The communication channel between the OU and the monitor CG may be maintained at all times if desired. In some embodiments the process may contact a third party registered to be alerted as may be set forth in the SSI.

The method then renders a disarm selection item for selection by the OU and/or a CG to disarm the wearable (step 310). A message is rendered such as "Disarm Device" or the like (e.g., "Abort," etc.) on a UI of the MS of the OU and/or the wearable and/or MS of one or more CGs depending upon system configuration as may be set forth in the SSI. In some embodiments, the system may illuminate a button using a blinking pattern to indicate that it is an abort button which may be depressed to select to disarm the system. The system may render the disarm selection item on a rendering device of the MS of the OU and/or the wearable and, in some embodiments, on the MS of a CG to enable the corresponding CG to disarm.

The system may then await a response from the OU. After rendering the disarm selection, the process may await a response from the OU and/or a CG to the disarm selection item. In some embodiments, the disarm selection item may include mechanical switch or the like that may be configured to disarm or otherwise deactivate the injection actuators of the cartridge. In some embodiments, the system may provide more than one dose of the opioid antidote to the OU via one or more hypodermic needles.

If the disarm (i.e. abort) device selection item has been selected (step 312), the method returns to step 282. Otherwise, if the disarm device selection item has not been selected, a shock is applied to the OU to gain their attention if sleeping, unconscious, or otherwise inattentive (step 314). It is envisioned that in some embodiments the shock may include the application of high voltage alternating current to the OU via one or more electrodes in contact with the skin of the OU. A high voltage coil or generator may be driven by the system to generate and output high voltage alternating current waveform that may be applied to the electrodes. The voltage should be sufficient to awake the OU if sleeping but not otherwise cause injury. The high voltage may be applied with, or in lieu of, other haptic signals (e.g., vibration, etc.) that may be generated by the system.

In some embodiments, the system may be configured to illuminate a flashing strobe light (e.g., for deaf users) with the application of high voltage. The type of shock applied may vary and may be defined in the SSI. It is envisioned that the shock may be applied on a periodic and/or nonperiodic interval for in infinite or defined interval as may be defined in the SSI. The shock may be stopped in response to selection of the disarm device selection (e.g., see steps 310 and 312).

The use history is then updated to reflect one or more of information input, generated, and/or received during the current QUE as well as selected system parameters (step 316). Accordingly, the history may be updated in accordance with information generated by system such as sensor information, user inputs, system parameters, etc., obtained or generated during a current QUE and stored in a memory of the system. In some embodiments, the outcome of the OUE may be stored in association with the QUE (e.g., overdose, no overdose, etc.). The history information may be stored in a suitable memory such as a memory of the MS of the OU, a memory of the cloud server, the EHR database, etc., in association with the OU ID for later use and/or analysis.

Self-Monitoring With Challenge

With reference to FIGS. 9A, 9B, in operation, the wearable is turned on and initialized by performing an initialization routine (step 320). It is envisioned that the wearable may be turned on using active or passive methods and thereafter perform an initialization process in a manner that is similar to that described supra in step 262 of the method of FIGS. 8A, 8B, 8C. Accordingly, the process may be configured to load SSI and may set system settings and parameters in accordance with the SSI. In the present embodiments a self-monitoring method (i.e. a method which does not use a monitor CG) may with a button press challenge be employed during an OUE as may be set as a default setting in the SSI. During this step, the process may perform system diagnostics to determine operational capabilities and/or determine whether the IC is coupled to the body of the wearable and may optionally communicate with the IC to determine its ID and/or status such as one or more of expired, used, new, type of medication, etc. If it is determined that the cartridge is used (e.g., has been previously used) or is expired the system may render information stating such on a UI of the system such as on a speaker and/or display of the wearable and/or MS such as "Injection Cartridge Has Been Previously Used Please Discard And Replace With A New One," "Injection Cartridge Is Expired Please Discard And Replace With A New One Cartridge" or the like depending upon system settings.

In some embodiments, the OU may be presented an option to select a monitoring method such as the self-monitoring method or a monitoring method employing a monitor CG (e.g., CG monitoring) method prior to starting the QUE. For example, the system may render information such as a selection items to select self-monitoring and/or CG monitoring, upon selection of one of these selection items the system may respond accordingly and set a system environment for the selected monitoring methods. In some embodiments, a dedicated button, key (hard of soft), or switch may be selected to select self-monitoring or CG monitoring which may be sensed by the system and the system may respond accordingly and set a system environment for the selected monitoring methods. In yet other embodiments, the self-monitoring method may be selected based upon communications availability.

Communication is then established between the wearable and an optional MS that may be registered thereto such as an MS of the OU using any suitable any suitable communication method(s) such as Bluetooth and/or the like depending upon system settings as may be set forth in the SSI (step 322). By pairing the MS, the UI as well as one or more sensors of this MS may be employed as sensors of the system. If communication with an MS is not established, however, it is appreciated that the wearable may be operative as a standalone unit. After establishing communication with the MS of the OU, information generated during step 320 for rendering on a UI of the system may be rendered on a UI of the MS such as the display, speaker, etc., dependent upon system settings.

The method then renders a request to start the opioid use event (OUE) (start OUE) for selection by the OU (step 324). In some embodiments, this request may be rendered using any suitable rendering device of the system such as a speaker, a display, a hard or soft key, a haptic device, etc., depending upon system settings as may be set forth in the SSI. For example, the system may render the request by illuminating on one or more buttons or hard or soft keys for selection by the user. Alternatively, the system may render one or more selection items instructing the OU such "press to start opioid use event," "start opioid use session," "start use," "start monitoring," etc., on a UI of the system such as on a display of the wearable and/or MS of the OU and await a response thereto from the OU.

In some embodiments, voice commands may be rendered using the speaker depending upon system settings as may be set forth in the SSI and the system may respond to voice inputs from the OU. In some embodiments, the process may await a gesture and/or haptic input that may be registered to start an OUE depending upon system settings as may be set forth in the SSI. During this act the system may render one or more of instructions using any suitable rendering device of the system such as a display of the wearable and/or MS and/or one or more speakers of the wearable and/or MS depending upon system settings as may be set forth in the SSI.

It is then determined whether the request to start the OUE has been selected (step 326). If not, the method returns to step 324. If the request to start is received, the OUE is started and an indication of such is rendered on a UI of the wearable and MS of the OU for the convenience of the OU (step 328). The process may set one or more threshold times such as alarm time threshold (T1) to 30 seconds and a response time threshold (T2) to 20 seconds. Note that other times are envisioned as may be set forth in the SSI. In some embodiments the values of T1 and T2 may be set such that T1>T2. The alarm time threshold (T1) may represent an alarm repeat time and the response time threshold (T2) may represent a response time within which the OU may respond.

The indication that the QUE has started may be rendered using, audio, graphical, textual, and/or haptic methods on corresponding rendering device of the wearable and/or MS (if paired) in accordance with system settings as may be set forth in the SSI. The process may further begin counting down T1 using a countdown timer. The indication of the start of the OUE may correspond with settings of the corresponding challenge.

The alarm is activated by rendering alarm information on a UI of the system using a graphical, textual, haptic, and/or audio methods on one or more corresponding rendering devices of the system in accordance with the current challenge (which is a button press challenge) as may be set forth in the SSI and may begin counting down T2 (step 330). Thus, the alarm information may correspond with the current challenge which is a button press challenge. Accordingly, a button may be rendered by the system on a UI of the system such as the wearable or MS of the OU. In some embodiments, the alarm information may include user defined content such as a game, a cartoon character, etc. in accordance with the selected challenge as may set forth in the SSI. The process may present a challenge by activating the alarm during the current step.

In the present embodiments, the alarm information may be graphically represented as a circle (e.g., red) selection item that may selected (e.g., by the OU) to respond to the challenge. In some embodiments, the alarm may be rendered by lighting an LED that is associated with a key or the like on the wearable using a flashing pattern that may increase a frequency (of flashing) and/or intensity as T2 is counted (e.g., down in the present embodiments) and the OU may respond by pressing the associated key or the like. In some embodiments, the alarm information may be rendered haptically using, for example, a pulse train (e.g., four pulses, etc. as may be defined in the SSI) that may be repeated to cause the wearable and/or MS of the OU to vibrate accordingly, as may be set forth in the SSI. In some embodiments the alarm may sound at nonperiodic intervals which may decrease in time from the start of the QUE. The alarm may correspond with the challenge.

Information requesting a response from the OU is then rendered such as "please respond to alarm, press button," "please press," "please select," "press red button," etc., "please say alarm off," "please say your name," "please say yes," "shake phone in a chopping motion," or any other request as may be set forth in the SSI and may be output via a display (e.g., the touchscreen display, a speaker, a haptic device, etc.) as may be set forth in the SSI (step 332). In some embodiments, the process may render information such as "please respond to challenge, press button" The input may then be received from the OU via any suitable UI of one or more of the wearable and/or MS of the OU. It is envisioned that the request as well as the input may be dependent on a plurality of settings of the system. For example, an input may depend upon how the alarm is rendered, e.g., using one or more of buttons, keys, graphical renderings on a touchscreen, an audio rendering, a haptic rendering, etc.

The process may also set a countdown time to 20 seconds (although other times are also envisioned as may be set forth in the SSI) and begin a countdown. The method then waits for a response from the OU to the alarm (challenge) rendered (step 334). The OU may enter a response by, for example, selecting a response selection item (e.g., a graphic or text) rendered on the display, by entering a gesture (e.g., a two finger swipe," by entering a voice command (e.g., "alarm off"), using haptics such as by rapidly performing a chopping motion using the MS of the OU, etc., as may be set forth in the SSI. In some embodiments, it is envisioned that the user may map a desired response (e.g., a two-finger swipe, etc.) to the alarm and store this setting in the SSI for later use. Thus, the system may map one or more haptic motions to an input, command, etc. An interface may be provided for the OU to select the desired mapping(s) of responses. The alarm may be rendered until the OU responds thereto as requested. In the present embodiments, it will be assumed that the OU responds to the alarm by selecting a selection item on a touchscreen display of wearable and/or the MS of the OU.

Receiving a response to the alarm from the OU (step 336) means that the challenge was successfully completed. Thus, via steps 330, 332, 334, 336, a challenge is presented to the OU and the OU responds to the challenge. In some embodiments, the values of countdown timers T1 and/or T2, can then be adjusted based upon a time in which the OU responded to the challenge in accordance with system settings. For example, T1 may be adjusted inversely to a time between the presentation of the challenge and the response thereto. This may shorten the T1 if the OU took more time to respond to the challenge.

It is then determined whether the countdown timer T1 has elapsed (step 352). If the T1 timer has not elapsed, the method continues with step 334. If the T1 timer has elapsed, the T1 timer is reset to its initial value (step 354). Note that other values for T1 are also envisioned. For example, T1 may be decremented or incremented (e.g., by one second etc.) after each iteration if desired or may be set to other values as may be set forth in the SSI.

If a response to the alarm from the OU is not received (step 336), it is determined whether the countdown timer T2 has elapsed (step 338). If it has not elapsed, the method continues with step 352. If the timer T2 has elapsed, an injection routine is activated to inject an opioid receptor antagonist (e.g., Naloxone and/or the like) into the OU (step 340). This step may be similar to step 306 of FIGS. 8A, 8B, 8C, accordingly reference will be made to that step for a more detailed description.

The OU can then be shocked at periodic times (e.g., every twenty seconds, although other times are also envisioned) to gain the attention of the OU (step 342). This step may be similar to step 314 of FIGS. 8A, 8B, 8C, accordingly reference will be made to that step for a more detailed description.

The method then awaits an abort signal that may be generated in response to a user action passively or actively (step 344). For example, with respect to an active abort, the system may generate the abort signal in response to selection of an abort button or key or via any other suitable user input via a UI of the wearable and/or MS of the OU. In the present embodiments, it will be assumed that a user may select an abort button or key (hard or soft) on a UI of the wearable and the system may generate the abort signal in response thereto. In yet other embodiments, the user may select an abort selection item on a touchscreen display of the wearable and/or MS of the OU and the system may generate the abort signal in response thereto. In yet other embodiments, the abort signal may be generated in response to an audio command input into the system via a microphone of the wearable and/or MS of the OU. In some embodiments, the system may render information including instructions to abort on a UI of the system such as on a display and/or speaker of the system. With regard to passively generating the abort signal, the system may generate the abort signal in response to the IC being removed from the wearable.

If an abort signal has not been generated (step 346), the method continues with step 342. If an abort signal has been generated, use history is updated locally and may thereafter be uploaded to the CS when communication with the CS is established as may be set forth in the SSI (step 348). This step may be similar to step 316 described supra.

Monitoring With Remote Monitor and Challenge

With reference to FIGS. 10A, 10B, 10C, in operation, the wearable may be turned on and may perform an initialization routine and may load SSI and may set system settings and parameters in accordance with the SSI (step 360). It is envisioned that the wearable may be turned on using active or passive methods, and may thereafter perform the initialization routine in a manner that is similar to that described in step 262 described supra. The SSI may include information related to the OU such as OU settings, opioid antidote (e.g., Narcan, etc.), desired dosage, syringe type (e.g., passive, active), penetration depth, etc. For the sake of clarity, it will be assumed that the present embodiments may employ a third party (i.e. remote) monitoring method (i.e. a method which employs a monitor CG) with a button press challenge, although other challenges may be employed depending upon system settings as may be set forth in the SSI during an OUE. This is in contrast to a self-monitoring method as described supra. In some embodiments, it is envisioned that the wearable may be turned on in response to communication pairing (e.g., Bluetooth pairing, etc.).

The wearable then establishes communication with the MS of the OU using any suitable communication method(s) such as by using wireless link such as Bluetooth or the like (step 362). For example, the wearable may perform Bluetooth pairing with the MS of the OU. The MS of the OU may be referred to as the OU-MS. In some embodiments, the wearable and/or the MS may provide the OU with an option to select an MS before establishing a connection with the wearable. Accordingly, the OU may select a desired MS and the system may respond accordingly to establish communication therewith and set this MS as the OU-MS. In some embodiments the SSI may set forth a default MS as the OU-MS. In some embodiments, the process may determine whether the wearable is registered to the MS and if not, it may request a login by the OU. This may provide for mixing MS which may be desirable in circumstances where an MS of the OU may be unavailable for various reasons such as low charge, etc. that may occur in an outdoors environment. In the present embodiments the wearable may include at least one wearable.

An opioid use session type (OST) is then selected (step 364). The OST may be selected in accordance with a default setting, a selection by the system, and/or a selection of the OU as may be set forth by the SSI. With regard to a selection by the system, the SSI may set forth a default OST. With regard to a selection by the system, the system may select an OST that may be determined to have a best fit to a desired OST as may be set forth in the SSI.

Figure 18:
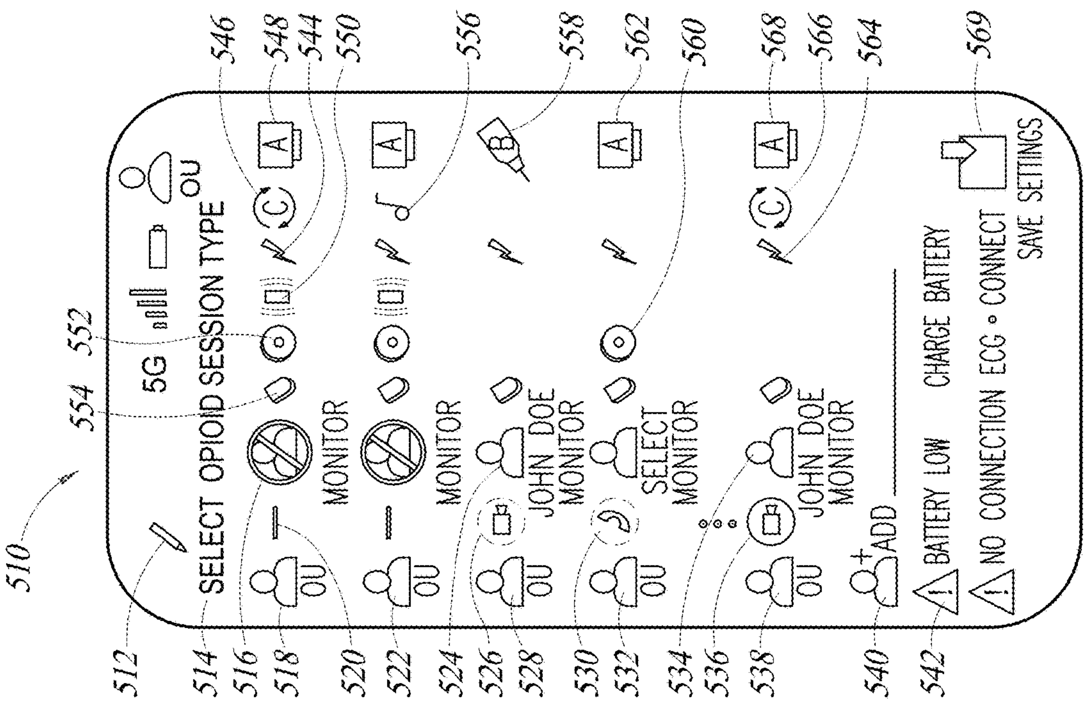
FIG. 18 is a diagram illustrating a sixth screen shot of portion of a display screen that may be rendered on the MS of the OU in accordance with embodiments of the present system.

With regard to the selection of an OST by the OU, it is envisioned that the system may render a UI which may provide options for the OU to select one or more OSTs which may be available currently or in the future for selection such as may be shown in FIG. 18 which illustrates a screen shot 510 illustrating a portion of a display screen that may be rendered on the MS of the OU in accordance with embodiments of the present system. The system may render one or more of instructions 514, OST type selection items 518, 522, 528, 532, 538, an edit selection item 512, a warning area 542, and a save selection item 596.

The instructions may be rendered by the system in accordance with a current window and may render information such as instructions to select an opioid session type (OST) or the like such as "Select An Opioid Session Type," as illustrated. The warning area may provide information related to the operation of one or more portions of the system such as error warnings, low battery power warnings, connection warnings, communication warnings, injection warnings, medication warnings (injector expired, injector used, etc.), coupling warnings (e.g., wearable not coupled correctly, etc.), and/or the like. The warnings may be determined by a self-diagnostic engine of the system and may be obtained from one or more portions of the system such as the wearable, the OU-MS, etc. Embodiments of the present system may include self-diagnostic routines which may diagnose, and provide information including warnings related to operation of one or more portions and/or functions of embodiments of the present system. The system may render information including instructions corresponding to the rendered warnings such as "Plug In Wearable-Low Battery Power," etc. in a selected format such as (instructions/warnings or vice versa) where the instructions may be mapped to each of the warnings and stored in the SSI. In some embodiments, remote diagnostics may be available.

The edit selection item 512 may be selected by the OU and the system may generate and render a UI including an editor (e.g., OST editor) with which the OU may edit a selected OST corresponding to a corresponding one of the OST type selection items. The OST editor may provide a menu including selection items (each representing an option for the OST build) which may be dragged and/or added to build and/or edit an OST. This may form a user defined OST. It is also envisioned that options of the OST being edited may be deleted by dragged them away and depositing in a virtual trash can. The OST may be updated and stored in SSI in a memory of the system in response to the system determining that the OU has selected the save OST selection item 569.

Figure 20:
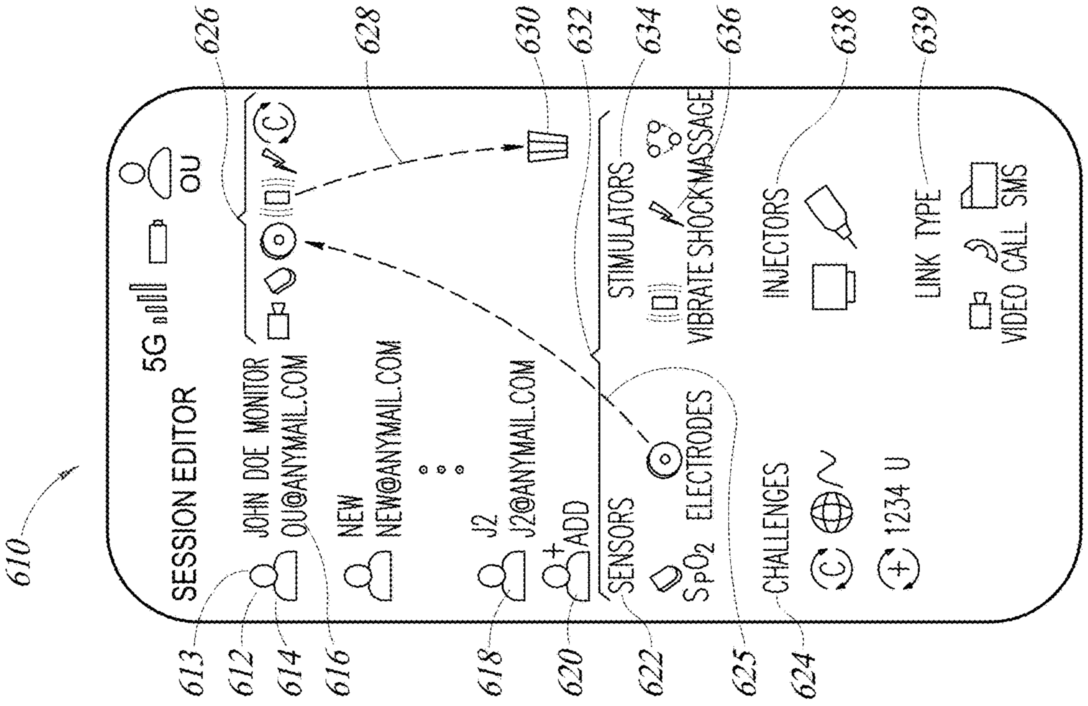
FIG. 20 is a diagram illustrating a screen shot of a portion of a display screen including an OST editor that may be rendered on the MS of the OU in accordance with embodiments of the present system.

For example, FIG. 20 which illustrates a screen shot 610 of a portion of a display screen including an OST editor that may be rendered on the MS of the OU in accordance with embodiments of the present system. The OST session editor may be configured to edit and/or build one or more OSTs 612 through 618. Each of the OSTs may be include a corresponding monitor CG and options 626 that may include one or more of sensor(s), stimulator(s), challenge(s), and injector(s) that may be employed to perform a corresponding OUE. Options may be listed in an options area 632 in which they may be listed in any suitable method such as a list, groups, etc. In the present embodiments, the options may be listed in groups which may include one or more of a sensors group 622, a challenges group 624, a stimulators group 634, an injectors group 638, and a link type group 639 each of which may include one or more available options (which may be graphically depicted for the sake of clarity) of the same type as the group and which may be dragged to a corresponding OST to be added to build the options for that. For example, the sensors group may include an $SpO_2$ sensor and an electrode sensor which may be dragged to build the OST as indicated by dotted line 625. Conversely, to remove options from an OST, an option may be dragged from the OST and dropped into a virtual trash can 630. This may be illustrated with reference to the OST where the vibrate option may be removed and dropped into the virtual trash can as illustrated by arrow 628. A new OST may be generated by selecting the selection item 620. The link types group may include a listing of links for establishing communication between the OU and the monitor CG during an OUE. Each OST such as the OST may include a monitor selection item 614 which may identify a corresponding monitor CG using a graphical depiction 613, an ID such as a name 637, and/or one or more contact email addresses 616 at which the monitor CG may be contacted to perform a corresponding OUE defined by the OSTs. Selecting on the monitor selection item 1 may open a listing of monitors for selection by the OU.

With reference to FIG. 18, each of the one or more OST type selection items may be associated with a corresponding OST and may have associated settings graphically (or textually) depicted therewith. These settings may include one or more settings such as monitor selection items 524, 534, link type item (e.g., telephone 530, video call 526, dash indicates absence of a link, etc.), link status item (e.g., bold circle about the link type indicator item indicates linked, grey circle about the link type indicator item indicates no link, physiological sensor indicator items (e.g., pulse oximetry 554, ECG 552, etc.), injector type indicator items (e.g., type A 562 and type B 558, etc.), a challenge item 566, a stimulus setting item (e.g., an electric shock item 544, 564, a vibration item 550, an audio item 556, etc.), one or more of which may be greyed out to indicate current unavailability and may be selected to view information associated therewith. With regard to the OST selection item, the corresponding OST may include the challenge item 546 indicative that this OST includes the challenge; the electric shock item 544 and the vibration item 550 which respectively indicate that that this OST includes electric shock and vibration as a stimulus; the type A injector item 548 which indicates that this OST uses a type A injector; the pulse oximetry and the ECG sensors which indicate that this OST includes pulse oximetry and ECG sensors as physiological sensors, respectively; and no monitor CG 516 (as illustrated by a crossed out line through the monitor selection item) indicative that no monitor is employed for this OST although one may be selected at a later time if desired.

It is envisioned that the monitor selection item may include a picture associated with a corresponding monitor CG, an avatar, an emoji, a memoji, a graphic, and/or the like as may be selected by a corresponding CG.

Figure 23:
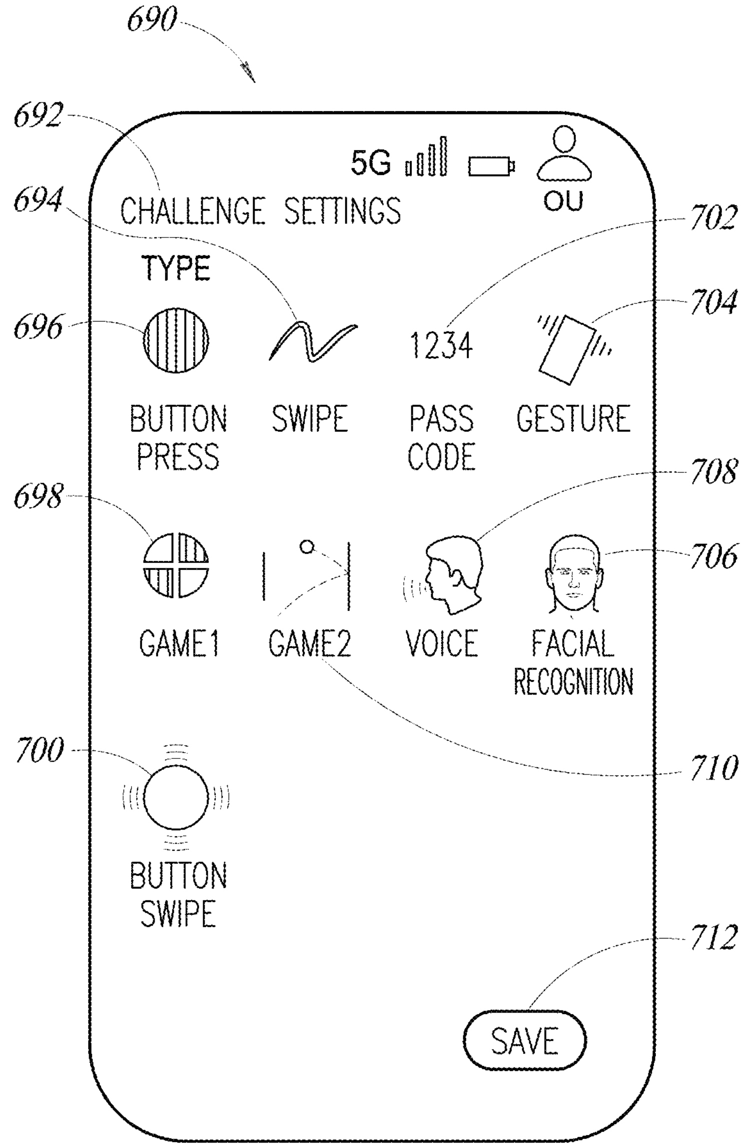
FIG. 23 is a diagram illustrating a screen shot of a portion of a display screen including a challenge settings menu having a plurality of challenge selection items in accordance with embodiments of the present system.

It is envisioned that the audio item may be mapped to audio content such as a musical note, tune, frequency, ringtone, etc., as may be selected by the OU and stored in a memory of the system in the SSI. Similarly, the challenge item may be mapped to challenge content such as a game, a gesture, etc., as may be selected by the OU and stored in a memory of the system in the SSI. Accordingly, a user may select a challenge for rendering during an OUE in real time or may select a challenge that may be associated with a corresponding OST (e.g., by mapping, etc.). Selection of a challenge is illustrated in further detail with respect to FIG. 23 which illustrates a screen shot 690 of a portion of a display screen including a challenge settings menu 692 having a plurality of challenge selection items 694 through 700 in accordance with embodiments of the present system.

A user may select a challenge selection item to select a corresponding challenge and may thereafter select a save selection item 712. In response, the system may save the corresponding selected challenge for use with a corresponding OST and/or OUE. Each challenge selection item may have an associated challenge. For example, the challenge selection item 696 may correspond with a button type challenge in which a button may be rendered, and the OU may depress this button to respond to successfully respond to the presented the challenge, threshold times and/or an alarm may be rendered. The challenge selection item 694 may correspond with a single finger swipe challenge in which the OU may perform a single finger swipe to respond to the challenge (e.g., in an N pattern as shown). The challenge 704 may correspond with a haptic gesture type challenge in which the OU may manipulate the OU-MS to perform the corresponding gesture to respond to the challenge. The challenge selection item 710 may correspond with a game type challenge in which the OU may play a game (e.g., "pong" or the like) to respond to the challenge. The challenge selection item 700 may correspond with a button swipe type challenge in which the OU may swipe a corresponding button to respond to the challenge.

It is envisioned that the challenges may include puzzles (such as solving puzzle, interacting with a puzzle, interacting with an alarm, etc.), playing a game (e.g., pong, Tetris, etc.) pressing a switch or key connected to the wearable, or pressing a virtual button on the wearable and/or on the OU-MS. Each challenge may have associated alarms, graphics, text, instructions, and/or threshold times such as one or more of an alarm time threshold, a response time threshold, and a stimulus threshold time, etc. which may vary in accordance with settings of the each corresponding challenge and/or system settings as may be set forth by the SSI.

With reference to FIG. 18, with regard to the OST selection item, the corresponding OST may include the challenge item 566 indicative that it includes a challenge, the stimulus may include the electric shock item, a type A injector, a video link (e.g., as shown by video camera icon 536) configured to connect the MSs of the OU and the monitor "John Doe" (e.g., 534), and an established link status.

Figure 19:
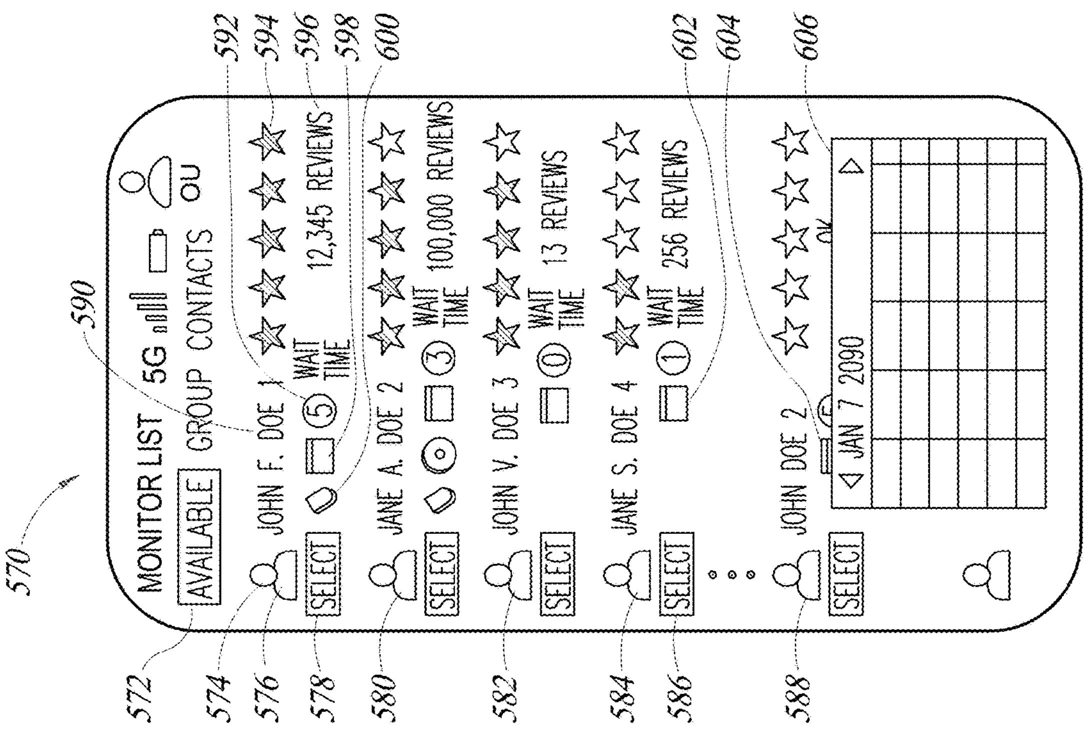
FIG. 19 is a diagram illustrating a screen shot of a portion of a display screen including an available monitor CG listing including a plurality of monitor CG selection items.

In some embodiments, upon detecting that the OU has selected one of the monitor selection items, the system may open a menu which may include an available monitor CG listing. This is illustrated with reference to FIG. 19 which illustrates a screen shot 570 of a portion of a display screen including an available monitor CG listing including a plurality of monitor CG selection items 576, 580, 582, 584. Each of the monitor CG selection items, such as monitor CG selection item 576, may be associated with a corresponding monitor CG and may include information associated with the corresponding monitor CG such as one or more of an avatar picture 574 (e.g., a picture of the monitor CG, a generic image, an emoji, a memoji, etc. as may be selected by the corresponding monitor depending upon system settings), a monitor selection item 578 (e.g., "select", etc.), identification 590 (e.g., a name, an identifier, etc.), sensor(s) employed 600 (e.g., pulse oximeter, etc.), a scheduling selection item 598, a current wait time 592, a rating selection item 594 (e.g., five stars, etc.), and a number of reviews 596 (e.g., 12,345, etc.).

In some embodiments, when the monitor CG may no longer be available for an QUE, the corresponding monitor selection item may be grayed out such as may occur when the corresponding monitor CG is begins an OUE and/or logs out in accordance with embodiments of the present system. The OU-MS may communicate with server of the system to obtain information related to each CG that may be determined to be available (or may be available later) to the OU for an QUE. The identification 590 of the monitor CG may include a name (real, pseudonym, alias, etc. depending upon system settings), organization name, or other identifier of the corresponding monitor CG, and the sensors employed 600 may represent sensors which the monitor CG may require to conduct an OUE as may be set forth in the SSI. The current wait time 592 may represent an expected wait time until the corresponding monitor CG may conduct an QUE. This wait time may be calculated by the system based upon a current schedule and/or OUE timing.

To select a monitor CG for a current or a scheduled QUE, the OU may select the monitor selection item 578 and the system may schedule the corresponding monitor for the corresponding OUE. In some cases, the monitor CG may have an expected (as determined by the system) wait time as may be illustrated by the current wait time 592 (e.g., five minutes, etc.) which may be updated in real time. When a monitor CG with a wait time is selected for an QUE by an OU, the system may determine the wait time and/or schedule of the monitor CG depending upon system configuration and may place the OU in a queue and render information on a UI of the OU-MS informing the OU of such. Then, when this monitor CG is determined to be available (e.g., after the wait time elapses), the system may alert the OU using any suitable method such as an alarm, a social media message, a text message, and/or the like as may be set forth in the SSI. The current wait time 592 may be determined by the system in real time and may be an average or actual time. For example, if the monitor CG has three OUEs on queue at the present time and is halfway through a current OUE, with each OUE averaging about 15 minutes, the system may determine that there is a wait of 15 minutes×(3+½ OUEs) 52.5 minutes for the current monitor CG and may update the current wait time 592 accordingly.

In some embodiments, the OU may schedule a future OUE with a monitor CG by selecting the scheduling selection item 598 and upon determining that scheduling selection item was selected, the system may acquire scheduling information for this monitor CG from a memory of the system such as the monitor database and render the acquired scheduling information on a rendering device of the system such as on the display of the OU-MS for the convenience of the OU. The scheduling information may be rendered in any suitable format such as in a calendar 606, graph, and/or chart formats (or the like) which may illustrate available time slots for the monitor CG. The OU, may then interface with the UI to select one or more time slots for scheduling a further OUE with the monitor CG and the system may save the selected schedule in a memory of the system for later use and/or analysis. For example, the system may update the monitor database. The system may then monitor the scheduling information for the OU and/or monitor CG and may alert both at or slightly before the scheduled OUE using any suitable method such as a call, contacting a social media address, a text message, a popup, etc. as may be set forth in the SSI of the OU and/or the monitor CG.

The rating selection item 594 and number of reviews 596 may represent ratings and number of reviews, respectively, as may be entered by OUs after an OUE is finished. It is envisioned that the system may include a ratings and review editor which may generate and render a UI with which an OU may interact with to enter a rating and/or a review for a monitor CG for a corresponding QUE. Once a rating and/or review is received from the OU, the system may associate the rating and/or review with a corresponding monitor CG and store this information in a memory of the system such as in the monitor database, for later use and/or analysis. In some embodiments, the system may be configured to list the monitor CGs in order of ratings and/or number of reviews depending upon system settings as may be set forth in the SSI. In some embodiments a monitor list may be acquired from a contacts list corresponding to an account of the OU such as from a memory of the OU-MS and/or social media account(s) of the OU. The OU-MS may communicate with (e.g., via a query, etc.) the CS to obtain information related to monitor CGs on this monitor list such as current status which may include availability information (e.g., currently available, unavailable), and scheduling information. In some embodiments, a list of currently available monitor CGs may be determined by the CS may be and provided to the OU-MS when requested such as when the selecting an OST. In some embodiments, information related to monitor CGs may be obtained from a memory of the system such as from the monitor database of the CS which may be updated in real time to reflect whether a monitor CG is currently available for an QUE.

With reference to FIG. 18, it is envisioned that the process may query for one or more of available monitor CGs, sensors, stimulators, and/or injectors and when rendering may illustrate availability with bold colors and/or unavailability by greying out when rendering on a UI of the system in association with a corresponding OST. When available, the process may attempt to establish communication with the sensor and/or injector to determine parameters of the corresponding sensor and/or injector such as current status (e.g. online, etc.), type (passive gas, active with actuator, active without actuator, etc.), parameters (e.g., 5 ml Narcan injector, etc.).

With reference to step 364 of the method of FIGS. 10A, 10B, 10C, the system may await selection of an OST by the OU and/or the system depending upon system settings as may be set forth in the SSI and may then configure system settings in accordance with the selected OST. In the present embodiments, it is assumed that the current OST may employ a monitor CG.

It is then determined whether a monitor CG has been selected for the current OST (step 366). If a monitor CG has not been selected, the OU is provided a UI with which they may select a monitor CG for the current OST (step 368). This may include a list of available monitor CGs for selection by the OU. This list may be rendered in any suitable format such as in a list form and/or in a graphic form depending upon user selections and/or system settings as may be set forth in the SSI and may be rendered similarly to that shown in FIGS. 18, 19, and 21 and described in the corresponding text infra.

Figure 21:
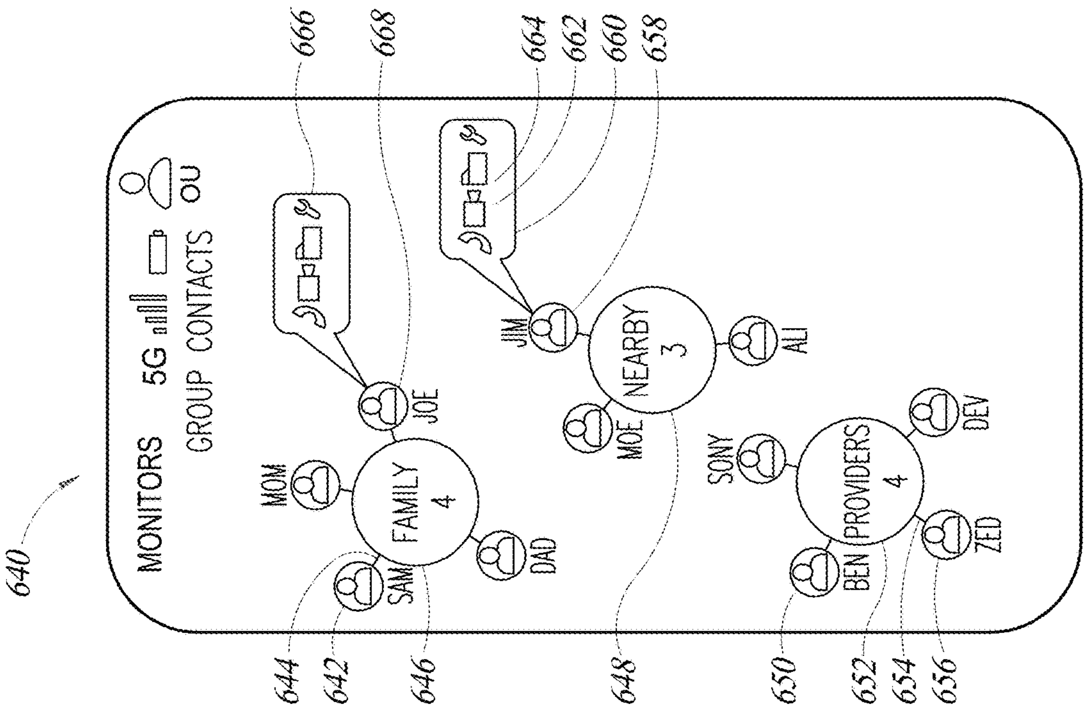
FIG. 21 is a diagram illustrating a screen shot of a portion of a display screen including an available monitor CG listing including monitor groups and subgroups in accordance with embodiments of the present system.

For example, FIG. 21 illustrates a screen shot 640 of a portion of a display screen including an available monitor CG listing including monitor groups and subgroups in accordance with embodiments of the present system. For example, a plurality of monitor CGs may each represented by monitor CG selection items 642 through 668 and may be associated with a corresponding monitor group such as monitor CG groups as represented by monitor CG group selection items as illustrated by corresponding links 644. To view information associated with a monitor CG, a user may hover over a corresponding monitor CG selection item to select it and the system may list information associated with the corresponding monitor CG in a corresponding popup box 660. For example, upon detecting that a user is hovering over the monitor CG selection item 648, the system may render information associated with this monitor CG in corresponding popup box 660. This popup box may include certain information related to the corresponding monitor CC, such as name, availability (e.g., available in 1 minute, etc.), and may include one or more selection items 662 to select to communicate with the monitor CG using an audio call, video call, and/or text message communication with the corresponding monitor CG for an OUE. For example, selecting a video call selection item 664 may be selected to set up a video call between the OU and the corresponding monitor CG for an QUE. In some embodiments, upon detecting that the user has selected a corresponding popup box 660, the system may open a window including further information related to the corresponding monitor CG.

Figure 22:
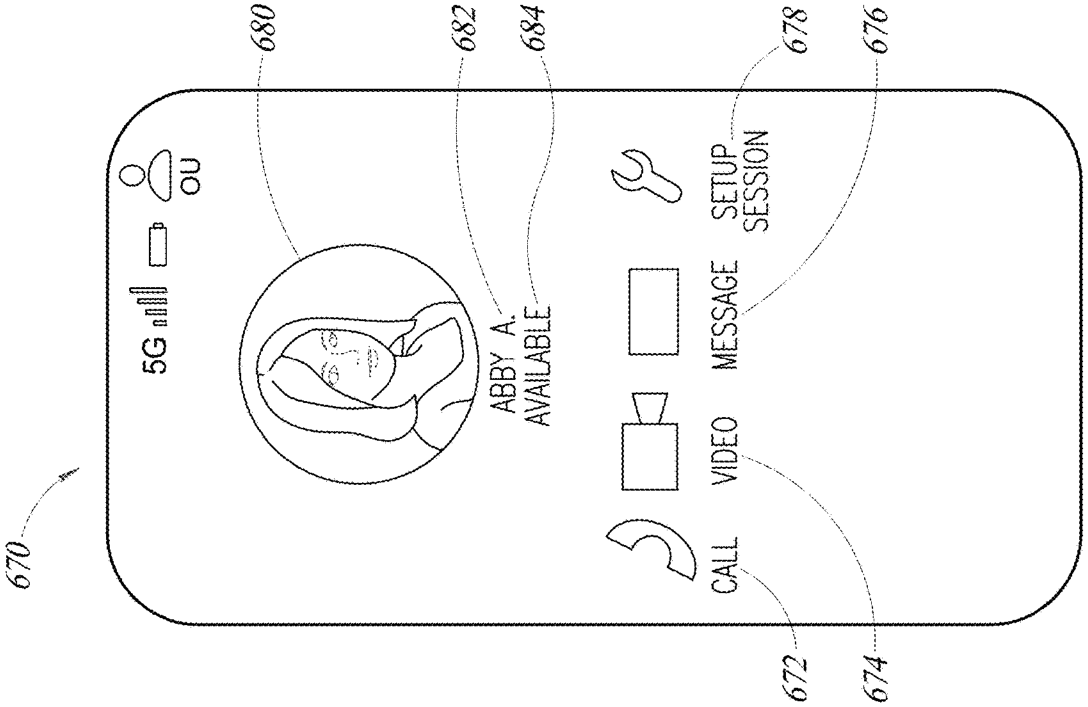
FIG. 22 is a diagram illustrating a screen shot of a portion of a display screen including an available monitor CG listing including information related to a selected monitor in accordance with embodiments of the present system.

This is illustrated in further detail with respect to FIG. 22 which illustrates a screen shot 670 of a portion of a display screen including an available monitor CG listing including information related to a selected monitor in accordance with embodiments of the present system. The process may render information related to the corresponding monitor CGs ID, such as an photograph 680, name 682, and an indication of current availability (e.g., available in one minute, etc.) 684, one or more selection items to select to communicate with this monitor CG for an OUS may include using an audio call selection item 672, a video call selection item 674, and a text message communication selection item 676 selection of which may setup an OUS with this monitor. A setup selection item 678 may be selected to setup an OUS with this monitor at a later time, etc.

With reference to step 368 of FIGS. 10A, 10B, 10C, in some embodiments, a default monitor CG (selected by the system) may be selected by the system automatically or in response to selection by the OU. The list of available monitor CGs may be obtained from the monitor database of the system and may include currently available monitor CGs.

If the monitor CG was selected (step 366), the MS of the OU may establish communication with an MS of the monitor CG via a network of the system using any suitable communication method(s). For example, in the present embodiments, it is envisioned that a video call may be established between the MS of the OU and the MS of the monitor CG. In some embodiments, MS may provide the OU with an option to select from one or more available monitor CGs before establishing a connection with the corresponding CGs MS. During this step, the MS of the OU may establish communication with an MS of a monitor CG via a network of the system using any suitable communication method(s) such as a 5G video call, etc. Communication may be established in accordance with a selected OST. For the sake of clarity, it may be assumed that a default OST has been selected in accordance with embodiments of the present system.

A self-diagnostic routine is then performed to determine if one or more selected portions of the system have failed (step 372). The selected portions of the system may include batteries, actuators, communication channels, and/or other portions of the system as may be defined in the SSI. With regard to the batteries, the system may check their charge and/or capacity and may be deemed to fail if found to have less than a threshold charge or threshold capacity. With regard to communication channels, these may include communication channels required for the current QUE. These channels may be established between one or more of the WU and the MS of the OU, the MS of the OU and a monitor CG or other CG, etc., and may fail (self-diagnostics) if a metric assigned thereto, such as the quality of service (QoS), is determined to be less than a threshold value (e.g., a QoS threshold value in the current example) for that channel. This may prevent unsatisfactory performance during the OUE. The selected portions may be selected to be portions that are essential for operation of the system during the OUE.

If the self-diagnostics did not pass (step 374), the method continues with step 418 in which the results of the self-diagnostic routine are rendered on a UI of the system such as on a display of the MS and/or the wearable (step 418). Note that the results may include information related to the selected portions of the system that were determined to have failed the self-diagnostics and may include instructions for resolving them. For example, if the communication channel(s) between the OU-MS and the MS of the monitor CG failed self-diagnostics then the system may be deemed to have failed self-diagnostics. For example, if one or more of the batteries were determined to have failed self-diagnostics, information related to a reason why the batteries failed self-diagnostics and information to resolve the failure may be rendered such as "Wearable Battery Low-Please Recharge Battery," "MS Battery Low-Please Recharge Before Use." Similarly, if a communication channel was determined to have failed self-diagnostics, information related to a reason why the corresponding channel failed self-diagnostics and information to resolve the failure may be rendered such as "Communication Between MS And Monitor CG Low Quality-Please Change Location And Retry." Selection items may be provided for the OU to obtain further information with regard to an error when selected. The method then continues with step 372.

The wearable passes self-diagnosis (step 374) if one or more selected portions of the system did not fail the self-diagnostics. If self-diagnosis passes, it is then verified whether the IC is coupled to the wearable (step 376). Information is obtained from one or more sensors of the system which may provide corresponding SI which may indicate whether the IC is coupled to the wearable. In some embodiments, one or more sensors may sense when the IC is coupled to the wearable and may generate SI indicating such. The method then analyzes this SI to determine whether the IC is coupled to the wearable. Depending upon embodiments, the process may further determine information related to the IC such as ID, IC type (passive, active, etc.), expiration date, previous use (e.g., used on Jan. 1, 2022, etc.), medication contained within a reservoir (e.g., "Narcan", user inserted, etc.), dosage, previous use, etc. depending upon system configuration. The information related to the IC may be obtained using one or more methods such as through wired, wireless, and/or optical methods.

For example, in some embodiments, a microswitch may sense whether the IC is coupled to the wearable and/or RFID may be employed to read the information related to the IC from a memory of the IC, etc. It is also envisioned that a wired coupling may read information from a memory of the IC. In some embodiments, it is envisioned that optical scanning methods may scan a code on a surface of the IC may be read when the IC is aligned to the wearable in which case the IC may be considered to be properly coupled to the wearable. This code may include information related to the IC. The process may then store the information related to the IC in a memory of the system for later use. The process may also transmit the information related to the IC to the CS for storage and later retrieval such as to determine whether an IC has been previously used elsewhere (e.g., in another wearable). Thus, the process may further communicate with a memory which may include information related to an IC and which may be updated by the system to reflect any possible use.

It is then determine whether the IC is coupled to the wearable (step 378). If the IC is not coupled to the wearable, information indicating that the IC is not coupled to the wearable is rendered on a UI of the OU-MS and/or the wearable (step 420). Content including instructions on properly coupling the IC to the wearable may also be rendered. The method then continues with step 376. It is also envisioned that a help selection item may be rendered and if selected by the OU, may provide and render further assistance such as video content, open a chat box for live help, etc. as may be selected by the OU.

If the IC is properly coupled to the wearable (step 378), it is then determined whether the IC is valid (step 380). An IC may be considered to be valid if not previously used and not expired. Accordingly, the process may analyze the information related to the IC obtained during step 376 to determine whether the IC was previously used or is expired in which case the process may determine that the IC is invalid. In some embodiments, the IC may be considered to be used if the IC performed an injection. The IC may be considered to be expired if its expiration date has passed. In some embodiments, IC validity may vary in accordance with system settings as may be set forth in the SSI.

If the IC is not valid (step 380), a UI During step 9018, the UI of the OU-MS and/or the wearable information indicating that the IC is not valid is rendered (step 422). In addition, an indication is provided about why the IC is not valid such as "Injection Cartridge Has Been Previously Used, Please Discard And Replace With New Injection Cartridge Before Continuing," "Injection Cartridge Expired, Please Discard And Replace With A New Injection Cartridge,"etc., as may be set forth in the SSI. The method then continues to step 376.

If the IC is valid (step 380), one or more selection items that may be selected by the OU to start the current opioid use event (OUE which may also be referred to as an opioid use session (OUS)) is rendered on an UI of the OU-MS and/or the wearable (step 382). The system them waits for a response. For example, the process may render a screen including one or more selection items that may be selected by the OU to start, stop, and/or set one or more settings of the OUE which may be considered a current OUE. The current address of the OU may be rendered for the convenience of the OU and may be selected by the OU for editing as may be necessary. The process may open a window or sub-window in which a live video of the monitor CG may be rendered.

Figure 13:
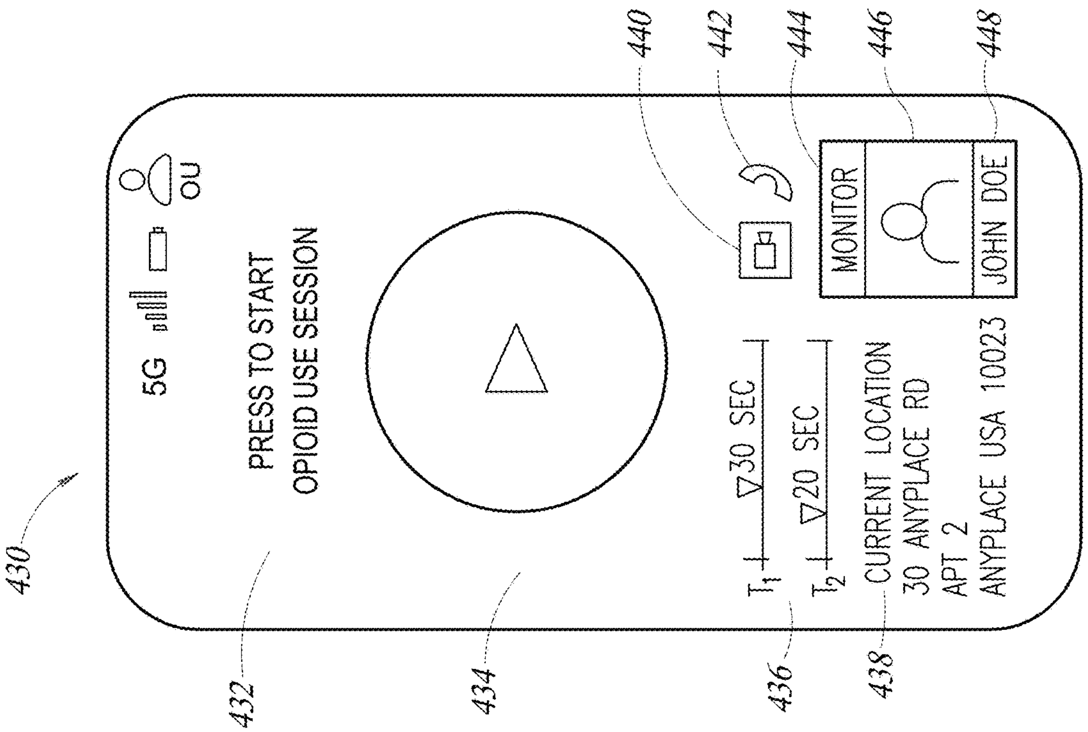
FIG. 13 is a diagram illustrating a first screen shot of a portion of a display screen that may be rendered on the MS of the OU in accordance with embodiments of the present system.

This is illustrated with reference to FIG. 13 which illustrates a screen shot 430 of a portion of a display screen that may be rendered on the MS of the OU in accordance with embodiments of the present system. The system may render a selection item which may be selected to start the QUE (which may also be referred to as a start OUE selection item) such as a start selection item 434 which may be highlighted in a desired color such a green or other color as may be set forth in the SSI. The system may then await selection of this start selection item by the OU.

The system may also render instructions 432 which may provide operational guidance to the OU on starting the current OUE such as "Press To Start Opioid Session," or the like as may be set forth in the SSI. Instructions may be rendered for each screen to seamlessly provide guidance to the OU. The process may also render one or more of an alarm time threshold selection item 436 and a response time threshold selection item 438 which may be manipulated to adjust an alarm time threshold (e.g., T1) and a response time threshold (e.g., T2), respectively, within a range defined by the system as may be set forth in the SSI.

The alarm time threshold selection item and the response time threshold selection item are illustrated as sliders although other type of selection items such as arrows and the like are also envisioned. Initial settings for T1 and T2 may be rendered and/or set in accordance with a default setting as may be set forth in the SSI. In some embodiments, the system may monitor for best settings for T1 and/or T2 for the OU and set times for T1 and T2 accordingly and save these settings in the SSI. The process may also render a video call window 446 which may render a video image of the monitor OU as a participant within the call window. Selection items such as a video call selection item 440 and a telephone call selection item 442, may be provided and may be selected to select between a video call and a telephone call, respectively, during the current OUE.

For example, when the video call (video conference) selection item is selected, the system may activate and/or maintain the video conference between the OU and the monitor CG during the QUE. Similarly, when the telephone call selection item is selected, the system may activate and/or maintain the telephone call between the OU and the monitor CG during the QUE.

Selection of the video call selection item and the telephone call selection item may be mutually exclusive with at least one having to be maintained during portions of the OUE to prevent losing communication between the OU and the monitor CG during the QUE. Identifying information of a participant of the video or audio call may be rendered in association with a screen rendering of the corresponding participant. For example, one or more of name and position of a participant may be rendered for the convenience of users such as the OU and one or more CGs such as the monitor CG. For example, with reference to the call window in which the participant "John Doe" is the monitor CG for the current QUE, a name area 448 may include the name "John Doe" and a title area 444 may identify the title such as "Monitor"

In some embodiments, screens during the OUE may include a background that may be selected to enhance clarity of controls for the convenience of the users. Background(s) may include colors, and/or images and may be stored in the SSI.

With reference to step 382, the method may further acquire SI from one or more sensors of the system such as from the sensors of the wearable, sensors of the OU-MS, etc. These sensors may include physiological sensors. The process may await an input from the OU and may respond accordingly.

It is then determined whether the start OUE selection item (e.g., 434 of FIG. 13) has been selected by the OU. If it has not been selected, the method returns to step 382. If it has been selected by the OU, the OUE starts a countdown of T1 from its initial setting (e.g., 30 seconds in one example embodiment) (step 386). Information indication such is rendered on a rendering device of the system such as the display of the OU (step 388). For example, the process may render information such as operational status of the QUE such as "Opioid Use Session In Progress," "Session Started," and may render a graphical and/or a numerical representation of count of T1 (which may indicate a remaining time for T1) and/or the like.

Figure 14:
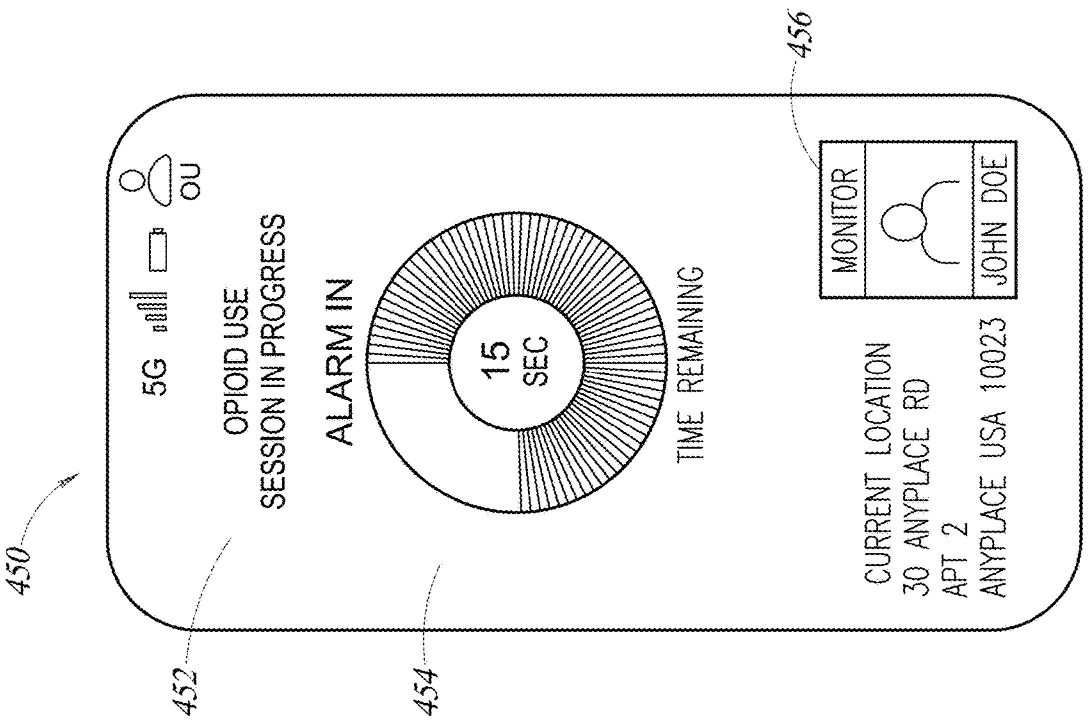
FIG. 14 is a diagram illustrating a second screen shot of a portion of a display screen that may be rendered on the MS of the OU in accordance with embodiments of the present system.

This is illustrated with reference to FIG. 14 which illustrates a screen shot 450 of a portion of a display screen that may be rendered on the MS of the OU in accordance with embodiments of the present system. Current OUE status (e.g., session status) 452 may indicate a current status of the session such as "Opioid Use Session Started," or "Opioid Use Session Ongoing," and/or the like.

A timer representation 454 may indicate a current count of time of T1 may be rendered numerically and/or graphically as shown with a remaining time (e.g., 15 seconds) surrounded by a disappearing circle/arc. A video call window 456 may be rendered as a picture-in-picture window and may include the monitor CG as a participant.

During the current session, the MS of the monitor CG may receive video and/or audio from the video or audio call with the OU and may receive SI from the OU-MS in accordance with system settings as may be set forth in the SSI.

It is then checked whether the alarm time threshold (T1) has elapsed (step 390). If it has not elapsed, the method returns to step 388. If it has elapsed, an alarm is rendered (e.g., which may present a challenge) on one or more rendering devices of the system such as one or more of a speaker, haptic device, and/or display of the system in accordance with system settings as may be set forth in the SSI (step 392). For example, in the present embodiments, the alarm may be rendered on the speaker, haptic device, and/or display of the OU-MS, a haptic device of the wearable to draw the attention of the OU. In some embodiments, the alarm may have a silent mode, which when selected, the process may render the alarm using the display and haptic device of the OU-MS so as to remain relatively silent.

Figure 15:
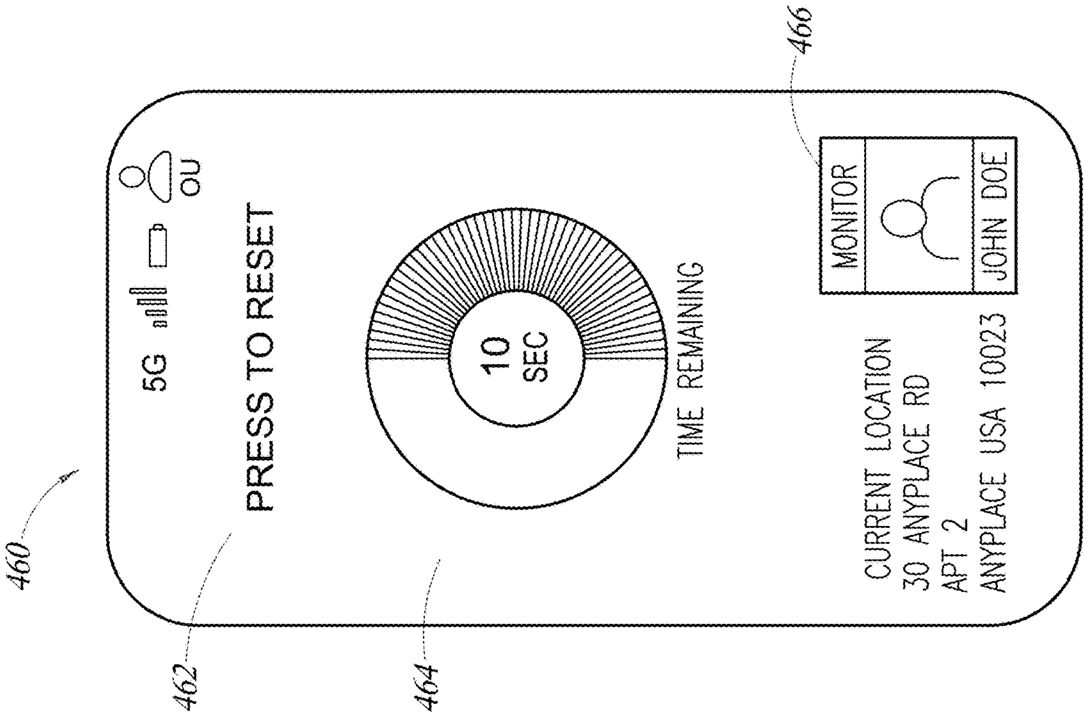
FIG. 15 is a diagram illustrating a third screen shot of portion of a display screen that may be rendered on the MS of the OU in accordance with embodiments of the present system.

The response time threshold (T2) along with a selection item are then rendered to stop the count (e.g., counting down) of the response time threshold (T2) (step 394). This is illustrated with reference to FIG. 15 which illustrates a screen shot 460 of a portion of a display screen that may be rendered on the MS of the OU in accordance with embodiments of the present system. The system may also render instructions 462 which may provide operational guidance to the OU on stopping the count of T2, such as "Press To Stop," or the like as may be set forth in the SSI. A stop selection item 464, illustrated as a timer representation, may indicate a current count of T2 may be rendered numerically and/or graphically as shown with a remaining time (e.g., 10 seconds) surrounded by a disappearing circle/arc. The OU may select the timer representation selection item to stop the timer. A video call window 466 may be rendered as a picture-in-picture window and may include the monitor CG as a participant.

It is then determined whether the OU has selected the stop selection item (step 396). If the user has selected to stop, the method returns to step 386. In the case that the stop selection item was selected, it may be determined that the OU responded to the alarm and that a response to the challenge was successful or successfully received. If it is determined that the stop selection item has not been selected by the OU.

It is then determined whether the response time threshold (T2) has elapsed (step 398). If T2 has not elapsed (step 398), step 398 loops until it does elapse. If it is determined that the response time threshold (T2) has elapsed, an alarm is rendered and may inform the monitor CG of the likelihood of an OD of the OU via a rendering device of the monitor CG such as on the display of the MS of the monitor CG (step 400). The alarm may be rendered on a speaker of the MS of the monitor CG or other device the monitor CG is logged in to and/or is using for conducting the current OUE. The process may obtain SI which may include vitals and/or other physiological sensor information collected from the OU and may transmit this SI to the MS of the monitor CG for further analysis and/or use. The SI transmitted to the monitor CG may correspond with system settings as may be set forth in the SSI.

Figure 17:
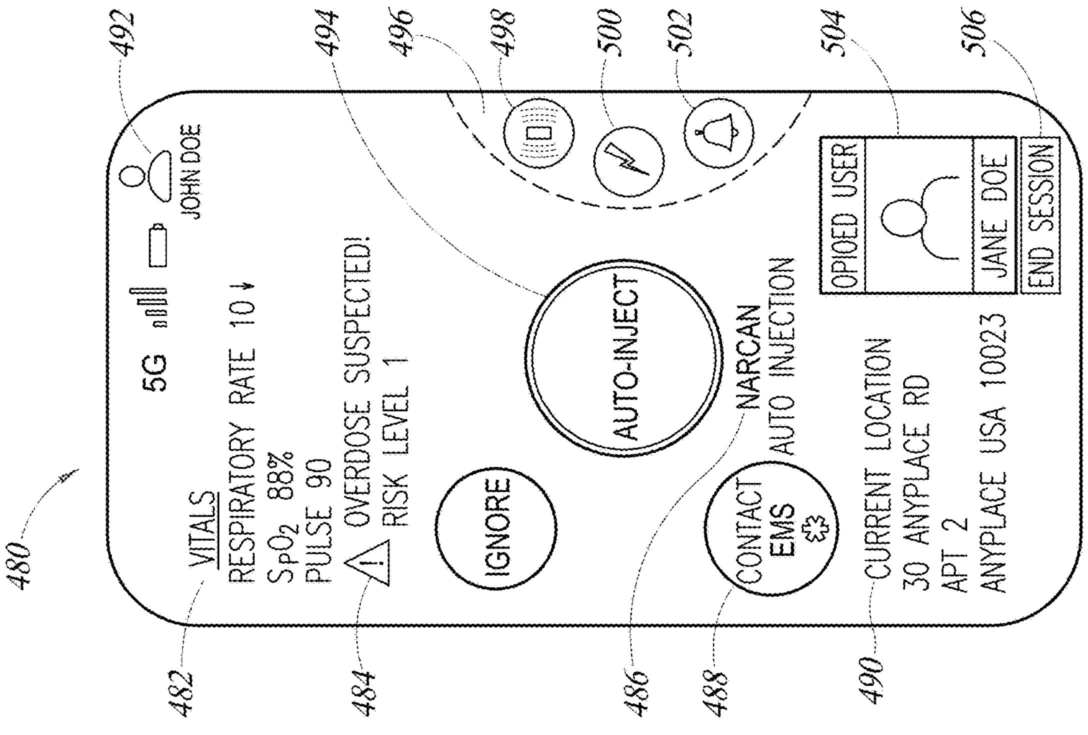
FIG. 17 is a diagram illustrating a fifth screen shot of portion of a display screen that may be rendered on the MS of the OU in accordance with embodiments of the present system.

One or more response items for the monitor CG are rendered to select such as inject and call EMS selection items for selection by the monitor CG (step 402). This is shown with reference to FIG. 17 which illustrates a screen shot 480 illustrating a portion of a display screen that may be rendered on the MS of the OU in accordance with embodiments of the present system. The system may render the current vitals of the OU 482, an auto-inject selection item 494, an end session selection item 506, an OD status 484, instructions 486, an EMS selection item 488, current location of the OU 490, an OU window 504, an account selection item 492, and stimulator selection items 498, 500, 502.

The current vitals of the OU 482 may include sensor information as may be available to the system and/or may be acquired in accordance with those set forth in the SSI such as respiratory rate and/or a trend indicator (e.g., see arrow), $SpO_2$ (e.g., in %), and pulse (e.g., in beats-per-minute), etc.

The auto-inject selection item 494 may be selected by the CG to initiate an auto-injection routine by the system to inject the opioid antidote into the OU and/or to provide a stimulus to the OU. It is also envisioned the auto-injection routine include a challenge that may be presented to the OU (by rendering on the OU-MS and/or the wearable) if desired in accordance with system settings as may be set forth in the SSI prior to the actual injection of the opioid antidote. If the OU responds successfully to this challenge the injection may be delayed. This challenge may be presented one or may be presented repeatedly during the QUE.

In some embodiments, the auto-inject selection item 494 may be selected to begin an auto-injection routine to inject the opioid antidote to counter the effects of the opioid and may be rendered graphically and/or textually such as by rendering a button a graphic or a textual description such as "Auto-Inject," or the like situated within (step 402). This button may change colors and/or brightness in accordance with the OD status 484. For example, when an OD is not suspected this button may be green, when an OD is suspected or imminent, the system may change color of this button to red and when an OD is not suspected, the system may change the color of this button to green. The system may monitor and/or change the colors in real time. The colors selection(s) and/or combinations thereof may be mapped in the SSI. In some embodiments, the colors and/or brightness may be varied based upon a predicted overdose (OD) confidence value ε which may be a normalized to have a value that is between 0 and 1 as generated by the system. In some embodiments, the colors may change from green to yellow and to red as the confidence value ε increases.

The OD status 484 may indicate a status of the OD as may be determined by the system in discrete terms such as OD suspected and/or OD occurring and/or the like as may be set forth in the SSI. In some embodiments, the OD status may be based upon, the predicted overdose (OD) confidence value ε which may be a normalized to have a value that is between 0 and 1. A current value of the confidence value ε may be rendered (e.g., to indicate risk level) as may a directional vector (such as an arrow) to indicate whether the risk level is increasing (upward arrow), remaining stable (horizontal arrow), or decreasing (down arrow).

The end session selection item 506 may be selected to end the current OUE and may include corresponding language and/or graphics. When the system determines that the end session selection item has been selected, the system may end the current opioid use event and update use history to reflect one or more of information input, generated, and/or received during the current QUE as well as selected system parameters and an outcome of the patient (e.g., OD, no OD, etc.). In some embodiments, a training selection item may be provided and, when selected, the system may train one or more artificial intelligence/machine learning algorithms and/or on models in accordance with the current OUE.

The instructions 486 may provide instructions to the CG such as "Press Auto-Injection Button To Administer Narcan," "Press Auto-Injection Button To Administer Opioid Receptor Antagonist," and/or may display a name of the opioid antidote contained in the IC such as "Narcan Auto-Injection" and/or the like as may be set forth in the SSI. In some embodiments, the name of the opioid antidote may be obtained from SI obtained from the IC. In embodiments, the instructions may include reference to a dosage to be provided as may be set in the SSI.

The EMS selection item 488 may be selected by the CG to contact EMS such that EMS may be directed to a location as indicated by the current location of the OU 490. In some embodiments, the RFA may be transmitted to the EMS services corresponding to a geographic location of the OU. The current location of the OU may correspond with a location determined by one or more location systems such as such as a location system of the MS (e.g., GPS, A-GPS, etc.), a location system of the wearable, and/or may be entered and/or edited by the OU such as APT 2A, 30 Anyplace Rd, Anyplace, USA 10029. This may be beneficial where the OU may be located in a building with many apartments and/or rooms in close proximity to each other and may be difficult to find.

The EMS selection item 488 may be rendered using graphic, text, and/or audio. For example, a round button may surround a textual description such as "Contact EMS," or the like. In some embodiments, the EMS selection item may be linked to the auto-inject selection item 494 such that when one of these selection items is selected, the other may be automatically selected as may be set forth in the SSI.

The OU window 504 may include a window for viewing a video of the OU transmitted from an MS of the OU in real time, or substantially real time, of the OU. The video may be captured by a camera of the MS of the OU. In some embodiments, the OU window 504 may include live video of the OU generated in accordance with the established video call between the OU and the monitor CG. In some embodiments, audio only may be established as per a telephone call. In yet other embodiments other forms of communication between the OU and the monitor CG may be established. The video of the OU may be captured by the camera of the OU-MS.

The account selection item 492 may be selected to view settings associated with a current user of the MS such as the monitor CG. Selecting the account selection item may open a window including one or more settings corresponding to the account of the CG. Saving these one or more settings may update the settings in a memory of the system.

The stimulator selection items 496 may be optional and may vary based upon system configuration and/or settings as may be set forth in the SSI. In the present embodiments, the stimulator selection items may include one or more of a vibration selection item, an electric shock selection item, and an alarm selection item, which when selected the system may activate a haptic device (e.g., a vibrator or transducer of the OU-MS and/or the wearable), an electric stimulus unit (e.g., a high voltage coil), and an audible alarm, respectively, of the wearable to gain the OUs attention. The stimulator selection items may be arranged in a radio dial manner wherein any of the stimulator selection items may be rotated by dragging them which may bring other stimulator selection items into view. These other stimulator selection items may include a massager, etc.

It is then determined whether the inject selection item has been selected by the monitor CG (step 404). If the inject item was not selected by the monitor, the method returns to step 400. If the inject selection item was selected by the monitor, an auto-injection routine is initiated (step 406). Accordingly, the process may control one or more injection actuators (IAs) to inject a desired saving medication into the OU. This auto-injection may include a delay timer which may delay auto-injection until information such as that indicated during step 408 may be rendered depending upon settings as may be set in the SSI. For the sake of clarity, this step may be similar to step 306 of FIGS. 8A, 8B, 8C and further description of this step may be found herein.

Information that may indicate the auto-injection routine may have been started is rendered along with an abort selection item which may be selected by the OU to abort, delay, and/or otherwise stop the auto-injection routine and any subsequent alarms that may follow depending upon system settings as may be set forth in the SSI (step 408). For example, the process may render information such as one or more of current status information (e.g., "Injection Started"), instructions (e.g., "Press To Abort"), and an abort selection item (e.g., "Abort") for selection by the OU.

Figure 16:
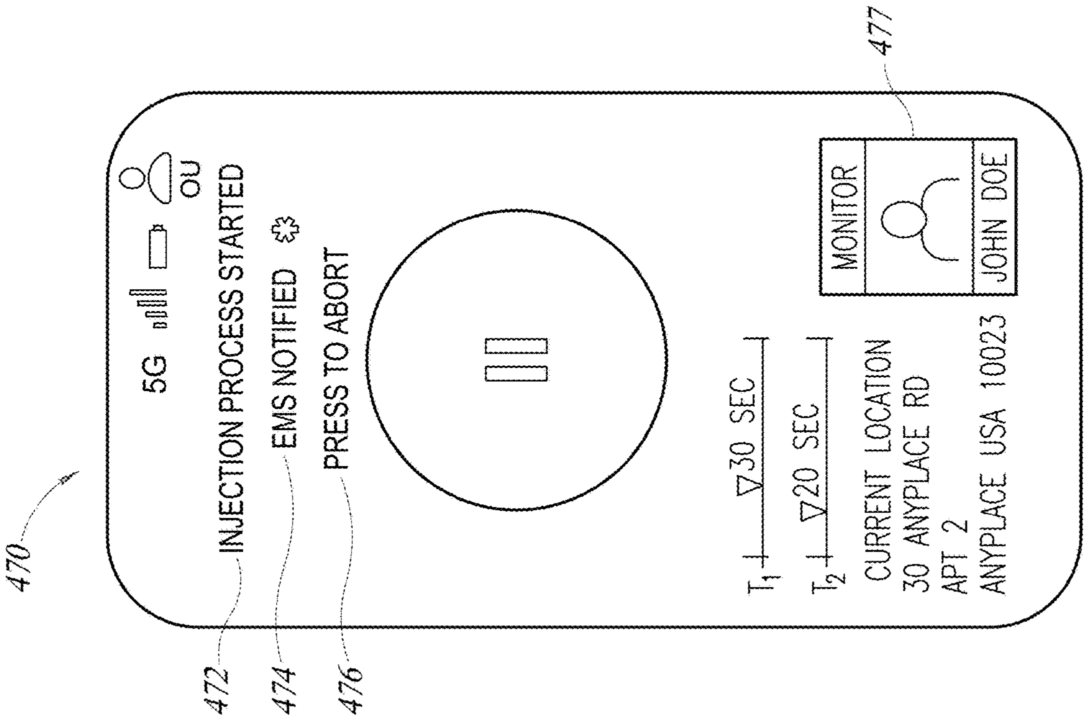
FIG. 16 is a diagram illustrating a fourth screen shot of portion of a display screen that may be rendered on the MS of the OU in accordance with embodiments of the present system.

This is illustrated with reference to FIG. 16 which illustrates a screen shot 470 of a portion of a display screen that may be rendered on the MS of the OU in accordance with embodiments of the present system. For example, the process may render one or more of an injection status item 472, an abort selection item 476, an EMS status item 474, a location status item 478, and a CG window 477, on a rendering device of the system such as the display of the MS of the OU for the convenience and/or selection by the OU. The process may also receive an input from the OU such as selection of the abort selection item, etc.

The injection status item 472 may indicate a current status of the injection routine. The system may query one or more sensors of the system to obtain sensor information that may indicate a current status of the injection routine such as about to start, in process, injection started, injection completed, etc. which may depend upon system configuration and/or may be set in the SSI. In some embodiments current status of the injection routine may be timed in accordance with one or more settings in the SSI. For example, the system may wait a period of time until staring the injection which period may be defined as Tinj0, a time during an injection Tinj1, and a time after injection Tinj3 which times may be set to 5 seconds, 20 seconds, and 1200 seconds (e.g., 20 minutes), respectively, as may defined in the SSI and may be counted down in sequence sequentially after each other. These times may be approximations.

For example, after determining to start an injection routine, the process may set time periods Tinj0, Tinj1, Tinj3 to their respective values as may be set in the SSI and may begin counting down starting with time period Tinj0 until it elapses, after that the system may count down time period Tinj1 until it elapses, and thereafter may count down time period Tinj3 until it elapses. The system may render information corresponding with each time period (e.g., Tinj0, Tinj1, Tinj3) in real time in accordance with system settings as may be set forth in the SSI. For example, during time period Tinj0 (which is a delay time until the injection of the opioid antidote), the system may provide the OU an opportunity to abort the injection routine before an injection, the system may render a notification such as of "Injection About To Start," or the like and may render the remaining time until the injection as may be indicated by a current value of Tinj0 as it is counted down.

During time period Tinj1 the system may render a notice which may inform the OU that the injection has started such as "Injection In Process," or the like. During time period Tinj2 the system may render a notice which may inform the OU that the injection has been completed such as "Injection Completed," or "Injection Completed Seek Emergency Help," In some embodiments, a plurality of injections may be performed and each may be counted and rendered for the convenience of the OU. For example, first injection completed, second injection completed, third injection completed, etc., and may render information indicating which injection has been completed. The system may track injections and/or their corresponding ICs for later use such as to verify ICs at a future time.

The abort selection item may be selected by the OU to abort the injection routine at any time and may be represented textually, audibly, and/or graphically such as by providing a textual description such as "Press To Abort," or the like, rendered in association with a large circle (e.g., a red circle until pressed at which time it may change to grey).

The EMS status item 474 may provide an indication of a current status of an EMS service request such as (e.g., "EMS Alerted," "Contacting EMS," "EMS Arrived," "On Way To Hospital," etc.) which status may correspond with the status of the EMS. The EMS status may be reported by an EMS server to the MS of the OU directly or via one or more other portions of the system such as the CS, etc.

The location status item 478 may correspond to the current location of the OU. In some embodiments, the current location of the OU may change in accordance with the current location of the OU as may be determined in real time.

The CG window 477 may display a live video image of the CG obtained from a camera of the MS of the CG. In the present embodiment the CG window provides a live video of the monitor CG. Although a single CG window is shown, in some embodiments a plurality of CG windows may be rendered simultaneously depending upon system settings.

With reference to step 408, the method may further transmit a RFA to emergency services (EMS) corresponding to the location of the OU. The RFA may include information related to the OU such as OU ID, location, etc.

It is then determined whether the OU has selected to abort (i.e. disarm) by selecting the disarm item (step 410). If the OU wants to abort, the system updates the use history to reflect one or more of information input, generated, and/or received during the current QUE as well as selected system parameters (step 416). This step may be similar to step 316 described supra.

If the OU does not choose to abort, a stimulus configured to gain the attention of the OU is provided and may start countdown of a stimulus threshold time (T3) from a value specified in the SSI (step 412). The stimulus may be configured to wake and/or or attempt to wake the OU who may be unconscious, semiconscious, and/or asleep. In the present embodiments, the stimulus may include an electrical shock of varying intensity and/or duration as may be set forth in the SSI. It is envisioned that in some embodiments the shock may include the application of high voltage alternating current to the OU via one or more electrodes in contact with the skin of the OU. A high voltage coil or generator may be driven by the system to generate and output high voltage waveform that may be applied to the OU via the electrodes. In some embodiments, the voltage may be applied in a stepped or ramp waveform beginning with a base voltage and may increase with each application up to a maximum voltage available depending upon system settings as may be set forth in the SSI.

In accordance with some embodiments, the base voltage may increase each time step 412 is executed (e.g., with each stimulus cycle). The steps of the ramp may increase with each application within a range of voltages as may be set in the SSI. The voltage may be sufficient to awake the OU if sleeping or unconscious but not otherwise cause injury. The high voltage may be applied with, or in lieu of, other haptic signals (e.g., vibration, etc.) that may be generated by the system.

In some embodiments the stimulus may include activating an illumination source (such as a strobe light) at or about the same time as the application of high voltage. The type of stimulus applied may vary and may be defined in the SSI. It is envisioned that the shock may be applied on a periodic and/or nonperiodic interval for in infinite, or defined interval in accordance with system settings as may be set forth in the SSI. The shock may be stopped when it is determined that the abort selection item has been selected. The stimulus threshold time (T3) may set a total time for each stimulus cycle such as 20 seconds in the current embodiments. Note that other values for T3 can also be used as may be set in the SSI.

It is then checked whether stimulus time threshold (T3) has elapsed (step 414). If not, the method loops until it elapses. If it is determined that the stimulus time threshold (T3) has elapsed, the method returns to step 408.

Monitoring With Challenge and Injection Delay

With reference to FIGS. 11A, 11B, in operation, the wearable may be turned on and thereafter initialized by performing an initialization routine (step 720). It is envisioned that the wearable may be turned on using active or passive methods and thereafter perform an initialization process in a manner that is similar to that described in step 262 described supra. The method is configured to load SSI and may set system settings and parameters in accordance with the SSI. The process may set values of an alarm time threshold (T1), response time threshold (T2), challenge time threshold (T3), missed count (MC), and a missed count threshold value (MCT) to threshold values such as 20 seconds, 10 seconds, 15 minutes, 0, and 1, respectively, as may be set forth in the SSI and/or may be set by a user such as the OU (within a set range).

The challenge time threshold may represent an approximate total time of the challenge if successfully performed by the OU. This time may be set such that it is longer than the time expected for respiratory depression (e.g., an OD) to occur after an opioid is inhaled or injected by the OU. In some embodiments, during the initialization the system may request to start an opioid use event with a delayed injection on a UI of the system such as on the OU-MS and/or the wearable depending upon system settings. It is also envisioned that system may render a preauthorization request for injection with the opioid antidote.

It is then determined whether the OU has indicated a request to start the QUE (step 722). Note that by responding to the request to start the OUE, the OU may provide a pre-authorization request to inject the opioid antidote. If no start request was received, the method loops until the OU requests to start the QUE. Once a start indication is received, the QUE is started and an indication of such is rendered on a UI of the wearable and MS of the OU for the convenience of the OU. At this time the process begins an injection delay which may delay an injection until results of the challenge are obtained (step 724).

The timers T1, T3 begin counting down (step 726). If the timer T1 has not yet elapsed (step 728), the method loops until T1 elapses. Once the timer T1 elapses, the method renders a challenge on a UI of the system such as on the UI of the wearable and/or OU-MS and timer T2 begins counting down (step 730). The challenge may include rendering a selection item (e.g., a challenge selection item) that may be selected by swiping in a desired direction(s) and/or pressing in accordance with system settings as may be set forth in the SSI. For example, in some embodiments, the selection item may be swiped up to respond to the challenge. Selection of the challenge selection item may be considered responding to the challenge. During this step, the process may render an alarm on a UI of the system such as on a speaker of the MS of the OU to gain the OUs attention depending upon system settings. A current value of T2 may be rendered until the selection item is selected.

It is then determined whether timer T2 has elapsed (step 732). If not, the method loops until it does. Once the timer T2 elapses, it is determined whether a response to the challenge was received from the OU (step 734). Note that selection of the challenge selection item may be considered as a response to the challenge. If it is determined the response to the challenge was not received from the OU (this may be considered a missed count), the method continues with step 744.

If a response to the challenge was received from the OU (step 734), it is determined whether the value of MC≥MCT (step 736). By comparing the values of MC and MCT this may allow for one or more missed responses to the challenge if desired as may be set in accordance with the SSI. If no (i.e., 0) missed challenges are desired, MCT may be set to one.

If the value of MC≥MCT, the injection delay is canceled (step 738) and a routine to inject the opioid antidote into the OU may be performed where the system initiates an auto-injection of the opioid antidote into the OU via one or more actuators and/or the wearable communicates with an auto-injector to initiate an auto-injection of the opioid antidote (step 739). Stimulation is applied to the OU after being the injection is completed (step 740). The wearable starts stimulating the OU by periodically applying a high volage signal to the OU via electrodes of the system. Thus, the process may provide periodic external stimulus to the opioid user after injection of the opioid antidote. The process may provide a selection item or key that, when selected by the OU may cancel the stimulus.

The wearable then attempts to notify one or more CGs of an OD of the OU such as one or more of the monitor CG, EMS CG, and/or MP CG via their respective registered contact addresses (step 742). In some embodiments, the process may attempt to communicate over any suitable channel to notify the EMS CG if unsuccessful.

If the value of MC≥MCT (step 736), the T1 and T2 timers are reset to their initial values and MC is incremented by one (which is now a current value of MC) (step 744). It is then determined whether the count-down timer T3 has elapsed (step 746). If it has not, the method continues with step 726. Thus, the challenge may be repeated (periodically or non-periodically depending upon system configuration) after the opioid use is started by the OU which may be considered to start concurrent with, or slightly before the start of the QUE. If the timer T3 has elapsed, the pending delayed injection is canceled (step 748).

Continuous Monitoring With Multiple Challenges

With reference to FIG. 12, in operation, after powering/on and initialization (step 750) and attempting to establish communications with the MS (step 751) as described in detail supra in connection with FIGS. 8A, 8B, 8C, 9A, 9B, 10A, 10B, 10C, 11A, 11B, and 12 the wearable begins monitoring the opioid user for respiratory depression and an associated risk level is determined either periodically or continuously (step 752). Sensor information is obtained from one or more sensors of the system such as an optical pulse oximetry sensor which may physiologically monitor an opioid user, form corresponding sensor information such as $SpO_2$ information which may then be analyzed to determine a risk level for the opioid user.

If the risk level is determined to be less than a threshold (step 753), the method continues the step of monitoring (step 753). If the risk level is determined to be greater than a threshold (step 753), a challenge is presented to the OU to interact with a UI of the system (step 754). The wearable renders a challenge on the UI and/or the MS of the OU depending upon system parameters and/or settings and may await a response to the challenge from the OU. In this manner, the challenge is only presented to the OU when the risk level is determined to be sufficiently high to warrant imposing the challenge on the OU. Otherwise, the wearable relies on one or more sensor data and related signal processing to detect a high enough risk of respiratory depression.

If the challenge is successfully completed it means that the OU successfully interacted with the challenge. Similarly, if the challenge is not successfully completed, it is assumed that the task was not completed successfully or simply not completed. If the challenge (i.e. task) was met (step 756), the risk level may be reassessed (step 758). This is achieved by obtaining sensor information from one or more sensors of the system and processing this information to determine a risk level for the opioid user which may be considered a current risk level. This process may be similar to the process described with reference to step 752 described supra.

The reassessed risk level is compared to the threshold (step 760). If the reassessed current risk level is greater than the threshold value, the method returns to step 754 and the challenge is presented to the OU again. If the reassessed current risk level is less than the threshold value, the method returns to monitoring the OU for respiratory depression (step 752).

If the challenge is not met (step 756), the opioid antidote is injected into the OU (step 762). Accordingly, the wearable performs an injection process to administer at least one dose of the opioid antidote into the opioid user. At this point it may be determined that the opioid user is experiencing an OD.

Post injection, the wearable may administer a shock or stimulus to the OU (step 764). Accordingly, the wearable may control an electrical shock generator circuit to generate a high voltage signal that may be applied to the OU via one or more electrodes coupled to opioid user.

The wearable then may alert one or more third parties and notify them of the overdose ODE depending on system settings. Third parties include for example a monitor CG, MP CG, and/or one or more EMS CGs. The alert/notification may include information related to the OU such as name, location, current physiological information such as vitals, etc. depending upon system settings.

In this manner, the OU may be presented with zero or more challenges over time depending on the risk level determined by the wearable. If the OU is presented with multiple challenges, failure of a single challenge will trigger an injection of the antidote. As long as the risk level remains below the threshold (whether statis or dynamic), the wearable does not present a challenge to the OU. If the risk level stays elevated beyond the threshold, the OU will be presented with continuous challenges which must be successfully met to prevent injection of the antidote.

Those skilled in the art will recognize that the boundaries between logic and circuit blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediary components. Likewise, any two components so associated can also be viewed as being "operably connected, "or "operably coupled,"to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the claims, any reference signs placed between parentheses shall not be construed as limiting the claim. The use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first," "second," etc. are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A method of detecting and treating an opioid overdose in an opioid user for use in a wearable, the method comprising:
- receiving and analyzing data from at least one physiological sensor to detect respiratory distress in the opioid user indicating a possible opioid overdose;
- notifying a monitor caregiver of the possible opioid overdose based on the data analysis;
- in response to a command from the monitor caregiver, injecting the opioid user with an opioid antidote via the wearable; and
- providing a periodic external stimulus to the opioid user after injection of the opioid antidote, said stimulus cancellable thereby, wherein said periodic external stimulus includes haptic, audible, and/or electrical stimulus.

2. The method according to claim 1, wherein said at least one sensor comprises at least one of a pulse oximeter sensor, end tidal CO2 sensor, chest wall muscle monitor, capnography, contactless respiratory rate monitor, body temperature monitor, infrared sensor, heart rate monitor, blood pressure monitor, motion sensor, radar based sensor, optical based sensor, acoustic sensor, thermal based sensor, a respiration monitor belt, and a respiratory sensor.

3. The method according to claim 1, wherein the opioid antidote comprises naloxone, Narcan, naltrexone, nalmefene, buprenorphine, or an opioid antagonist or mixtures thereof.

4. The method according to claim 1, further comprising transmitting information related to at least one of use medical history, the overdose status, and/or injection status of the opioid antidote to the monitor caregiver and/or emergency medical services (EMS).

5. The method according to claim 1, further comprising requesting pre-authorization for an injection of an opioid antidote from the opioid user and/or the monitor caregiver before opioid use by the opioid user.

6. A method of detecting and treating an opioid overdose in an opioid user for use in a wearable, the method comprising:
- monitoring the opioid user for respiratory depression utilizing at least one sensor;
- if the level of respiratory depression exceeds a threshold, notifying a monitor caregiver of a possible opioid overdose and periodically presenting the opioid user with a time-limited challenge;
- upon failure of said challenge, notifying the monitor caregiver of an overdose of the opioid user; and
- in response to a command from the monitor caregiver, injecting an opioid antidote into the opioid user.

7. The method according to claim 6, wherein said at least one sensor comprises at least one of a pulse oximeter sensor, end tidal CO2 sensor, chest wall muscle monitor, capnography, contactless respiratory rate monitor, body temperature monitor, infrared sensor, heart rate monitor, blood pressure monitor, motion sensor, radar based sensor, optical based sensor, acoustic sensor, thermal based sensor, a respiration monitor belt, and a respiratory sensor.

8. The method according to claim 6, wherein the opioid antidote comprises naloxone, Narcan, naltrexone, nalmefene, buprenorphine, or an opioid antagonist or mixtures thereof.

9. The method according to claim 6, further comprising providing a periodic external stimulus to the opioid user after injection of the opioid antidote, said stimulus cancellable by the opioid user.

10. The method according to claim 6, further comprising transmitting information related to at least one of the medical history of the opioid user, overdose status, and injection status of the opioid antidote to the monitor caregiver and/or emergency medical services (EMS).

11. The method according to claim 6, further comprising requesting pre-authorization for an injection of an opioid antidote from the opioid user and/or the monitor caregiver before opioid use by the opioid user.

12. The method according to claim 6, wherein the challenge comprises having the opioid user complete a task on the wearable or a mobile station of the opioid user.

13. The method according to claim 12, wherein the task comprises solving a puzzle, playing a game, pressing a hard key connected to the wearable, pressing a switch connected to the wearable, or pressing a virtual button on the wearable or the smartphone.

14. A method of detecting and treating an opioid overdose in an opioid user for use in a wearable, the method comprising:

periodically presenting a time-limited challenge to the opioid user after initiating use of an opioid;

upon failure of said challenge, notifying a monitor caregiver of a possible overdose of the opioid user;

in response to a command from the monitor caregiver, injecting an opioid antidote into the opioid user; and providing a periodic external stimulus to the opioid user after injection of the opioid antidote, said stimulus cancellable thereby, wherein said periodic external stimulus includes haptic, audible, and/or electrical stimulus.

15. The method according to claim 14, wherein the challenge comprises having the opioid user complete a task on the wearable or a mobile station of the opioid user.

16. The method according to claim 15, wherein the task comprises solving a puzzle, playing a game, pressing a hard key connected to the wearable, pressing a switch connected to the wearable, or pressing a virtual button on the wearable or the smartphone.

17. The method according to claim 14, wherein said at least one sensor comprises at least one of a pulse oximeter sensor, end tidal CO2 sensor, chest wall muscle monitor, capnography, contactless respiratory rate monitor, body temperature monitor, infrared sensor, heart rate monitor, blood pressure monitor, motion sensor, radar based sensor, optical based sensor, acoustic sensor, thermal based sensor, a respiration monitor belt, and a respiratory sensor.

18. The method according to claim 14, wherein the opioid antidote comprises naloxone, Narcan, naltrexone, nalmefene, buprenorphine, or an opioid antagonist or mixtures thereof.

19. The method according to claim 14, further comprising transmitting information related to at least one of user medical history, the overdose status, and injection status of the opioid antidote to the monitor caregiver and/or emergency medical services (EMS).

20. The method according to claim 14, further comprising requesting pre-authorization for an injection of an opioid antidote from the opioid user and/or the monitor caregiver before opioid use by the opioid user.

* * * * *